(12) United States Patent
Falwell et al.

(10) Patent No.: US 8,961,509 B2
(45) Date of Patent: Feb. 24, 2015

(54) ELECTROPHYSIOLOGY LOOP CATHETER

(71) Applicant: C.R. Bard, Inc., Murray Hill, NJ (US)

(72) Inventors: Gary S. Falwell, Moultonborough, NH (US); David MacAdam, Millbury, MA (US); Darany Kuong, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/668,618

(22) Filed: Nov. 5, 2012

(65) Prior Publication Data

US 2013/0165922 A1 Jun. 27, 2013

Related U.S. Application Data

(62) Division of application No. 10/533,596, filed as application No. PCT/US03/34828 on Oct. 31, 2003, now abandoned.

(60) Provisional application No. 60/422,707, filed on Oct. 31, 2002.

(51) Int. Cl.
*A61B 18/14* (2006.01)
*A61B 5/042* (2006.01)
(Continued)

(52) U.S. Cl.
CPC ........... *A61B 18/1492* (2013.01); *A61B 5/0422* (2013.01); *A61B 5/6856* (2013.01);
(Continued)

(58) Field of Classification Search
CPC ........... A61B 2018/00351; A61B 2018/00357; A61B 2018/00369; A61B 2018/14; A61B 2018/144

USPC ............. 600/374, 381; 606/32, 41; 604/95.04
See application file for complete search history.

(56) References Cited

U.S. PATENT DOCUMENTS

| 4,998,923 | A | 3/1991 | Samson et al. |
| 5,195,968 | A | 3/1993 | Lundquist et al. |

(Continued)

FOREIGN PATENT DOCUMENTS

| DE | 38 19 372 C | 1/1990 |
| EP | 0 790 066 A2 | 8/1997 |

(Continued)

OTHER PUBLICATIONS

Communication dated Mar. 7, 2012, in Japanese patent Application Serial No. 2004-548623.
(Continued)

*Primary Examiner* — Jaymi Della
(74) *Attorney, Agent, or Firm* — Seager, Tufte & Wickhem, LLC

(57) ABSTRACT

A catheter including control, localization, and/or fluid delivery features, and methods of using the same. One embodiment is directed to an electrophysiology catheter including a superelastic wire and a cable, and a method of controlling the catheter using the cable. Another embodiment is directed to an electrophysiology catheter including an adhesive to bias the orientation of the catheter. A further embodiment is directed to an electrophysiology catheter including adhesive and one or more cables, and a method of controlling the catheter using the one or more cables. Another embodiment is directed to a method including acts of injecting a fluid into the heart of a patient and adjusting the diameter of an arcuate curve of the catheter. Further embodiments are directed to a catheter having multiple position sensors on an arcuate curve of the catheter, or a position sensor associated with a movable electrode of the catheter.

14 Claims, 32 Drawing Sheets

(51) Int. Cl.
  *A61B 5/00* (2006.01)
  *A61B 18/18* (2006.01)
  *A61B 18/00* (2006.01)
  *A61B 18/12* (2006.01)

(52) U.S. Cl.
  CPC ... *A61B18/1815* (2013.01); *A61B 2018/00273* (2013.01); *A61B 2018/00375* (2013.01); *A61B 2018/1286* (2013.01); *A61B 2018/1407* (2013.01); *A61B 2018/1435* (2013.01); *A61B 2018/1467* (2013.01)
  USPC .......................................... 606/41; 604/95.04

(56) References Cited

U.S. PATENT DOCUMENTS

| | | |
|---|---|---|
| 5,242,394 A | 9/1993 | Tremulis |
| 5,322,064 A | 6/1994 | Lundquist |
| 5,327,905 A | 7/1994 | Avitall |
| 5,329,923 A | 7/1994 | Lundquist |
| 5,334,168 A | 8/1994 | Hemmer |
| 5,354,297 A | 10/1994 | Avitall |
| 5,358,478 A | 10/1994 | Thompson et al. |
| 5,383,852 A | 1/1995 | Stevens-Wright et al. |
| 5,437,282 A | 8/1995 | Koger et al. |
| 5,449,343 A | 9/1995 | Samson et al. |
| 5,462,527 A | 10/1995 | Stevens-Wright |
| 5,545,200 A | 8/1996 | West et al. |
| 5,558,643 A | 9/1996 | Samson et al. |
| 5,575,772 A | 11/1996 | Lennox |
| 5,596,996 A | 1/1997 | Johanson et al. |
| 5,611,777 A | 3/1997 | Bowden et al. |
| 5,626,136 A | 5/1997 | Webster, Jr. |
| 5,642,736 A | 7/1997 | Avitall |
| 5,643,231 A | 7/1997 | Lurie et al. |
| 5,680,860 A | 10/1997 | Irman |
| 5,755,760 A | 5/1998 | Maquire et al. |
| 5,782,900 A * | 7/1998 | de la Rama et al. .......... 607/122 |
| 5,810,887 A | 9/1998 | Accorti et al. |
| 5,820,591 A | 10/1998 | Thompson et al. |
| 5,830,214 A | 11/1998 | Flom et al. |
| 5,836,947 A * | 11/1998 | Fleischman et al. ............ 606/47 |
| 5,843,076 A | 12/1998 | Webster et al. |
| 5,865,800 A | 2/1999 | Mirarchi et al. |
| 5,916,178 A | 6/1999 | Noone et al. |
| 5,931,811 A | 8/1999 | Haissaguerre et al. |
| 5,938,588 A | 8/1999 | Grabover et al. |
| 5,938,694 A | 8/1999 | Jaraczewski et al. |
| 5,957,961 A | 9/1999 | Maguire et al. |
| 6,074,351 A | 6/2000 | Houser et al. |
| 6,096,036 A | 8/2000 | Bowe et al. |
| 6,099,524 A | 8/2000 | Lipson et al. |
| 6,126,654 A | 10/2000 | Horzewski et al. |
| 6,178,354 B1 | 1/2001 | Gibson |
| 6,217,567 B1 | 4/2001 | Zadno-Azizi et al. |
| 6,241,727 B1 | 6/2001 | Tu et al. |
| 6,245,066 B1 | 6/2001 | Morgan et al. |
| 6,254,568 B1 | 7/2001 | Ponzi |
| 6,278,563 B1 | 8/2001 | Hewlett |
| 6,308,090 B1 | 10/2001 | Tu et al. |
| 6,315,778 B1 | 11/2001 | Gambale et al. |
| 6,325,797 B1 | 12/2001 | Stewart et al. |
| 6,375,628 B1 | 4/2002 | Zadno-Azizi et al. |
| 6,447,506 B1 | 9/2002 | Swanson et al. |
| 6,607,520 B2 | 8/2003 | Keane |
| 6,616,628 B2 | 9/2003 | Hayzelden |
| 6,728,563 B2 | 4/2004 | Rashidi |
| 6,771,996 B2 | 8/2004 | Bowe et al. |
| 7,300,438 B2 | 11/2007 | Falwell et al. |
| 8,206,384 B2 | 6/2012 | Falwell et al. |
| 2001/0025134 A1 | 9/2001 | Bon et al. |
| 2001/0039413 A1 | 11/2001 | Bowe |
| 2002/0065514 A1 | 5/2002 | Rashidi |
| 2002/0072663 A1 | 6/2002 | Fuimaono et al. |
| 2002/0165441 A1 | 11/2002 | Coleman et al. |
| 2003/0097128 A1 | 5/2003 | Hayzelden |
| 2003/0125663 A1 | 7/2003 | Coleman et al. |

FOREIGN PATENT DOCUMENTS

| | | |
|---|---|---|
| EP | 1 199 082 A1 | 4/2002 |
| JP | 05265684 | 4/1995 |
| JP | 10189489 | 1/2000 |
| JP | 2003-230630 | 8/2003 |
| WO | WO 97/07848 | 3/1997 |
| WO | WO 97/42996 | 11/1997 |
| WO | WO 01/01877 A1 | 1/2001 |
| WO | WO 01 37723 A | 5/2001 |
| WO | WO 02 094334 A | 11/2002 |

OTHER PUBLICATIONS

Communication dated Jul. 18, 2011 in European Patent Application Serial No. 03781676.6.
Communication dated Feb. 29, 2012 in European Patent Application Serial No. 03781676.6.
Official Action dated Oct. 5, 2009 in Japanese Patent Application Serial No. 2004-548623.
Official Action dated Aug. 13, 2010 in Japanese Patent Application Serial No. 2004-548623.
Pretrial Reexamination Report dated Oct. 25, 2011 in Japanese Patent Application Serial No. 2004-548623.
Decision of Rejection dated May 17, 2011 in Japanese Patent Application Serial No. 2004-548623.
International Preliminary Report, Jul. 18, 2005.
International Search Report, Aug. 2, 2004.

* cited by examiner

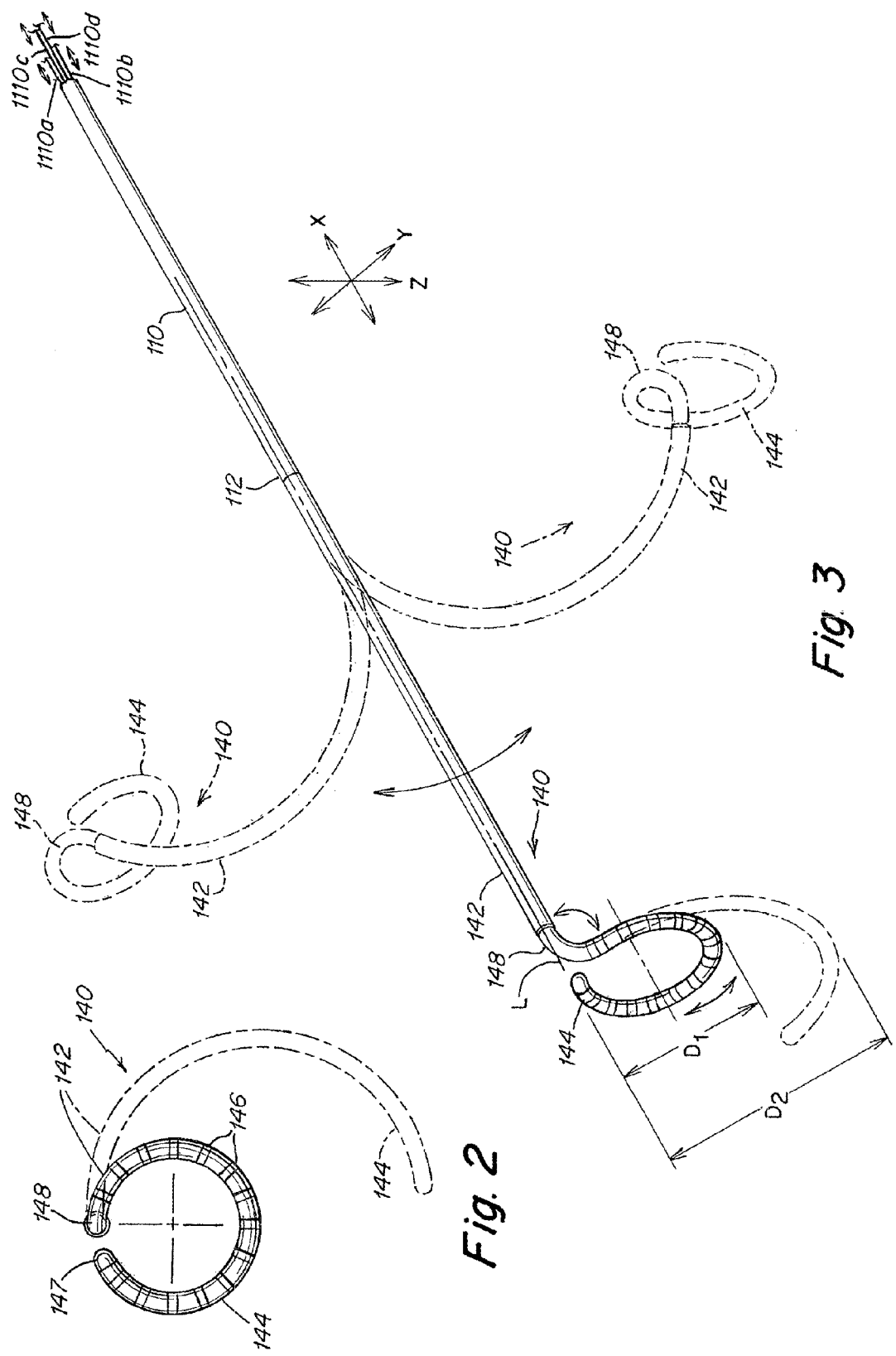

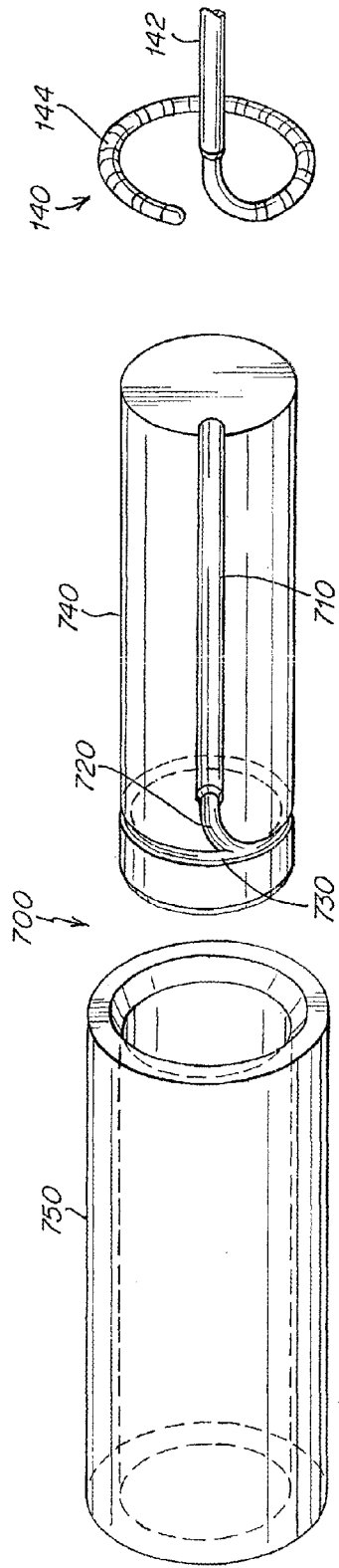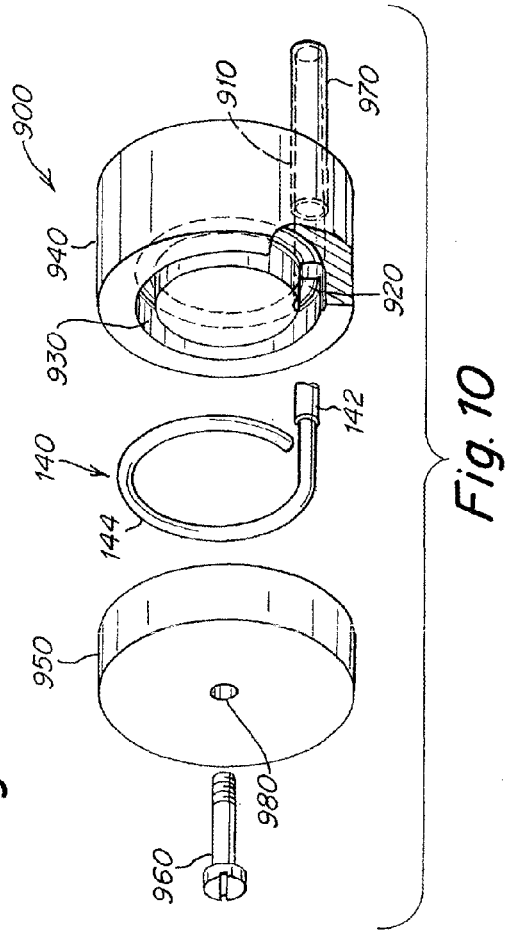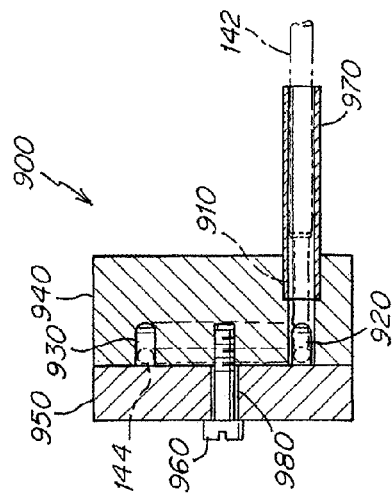

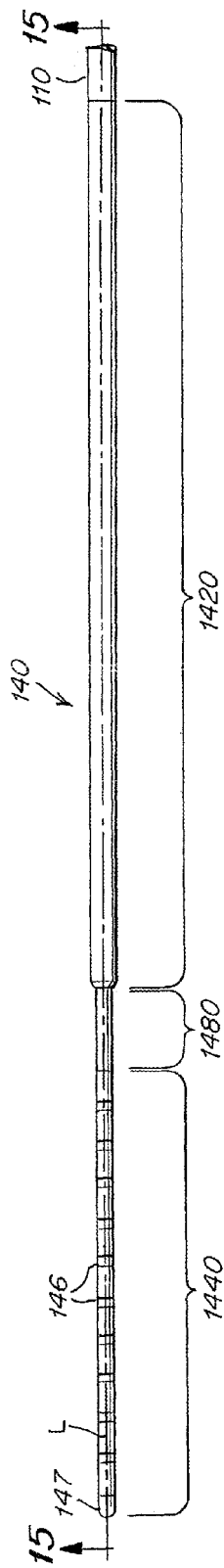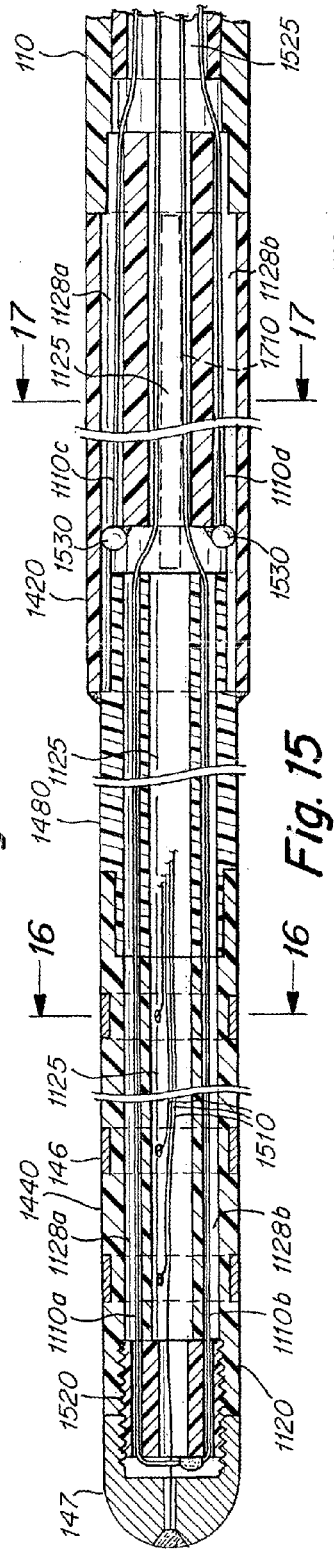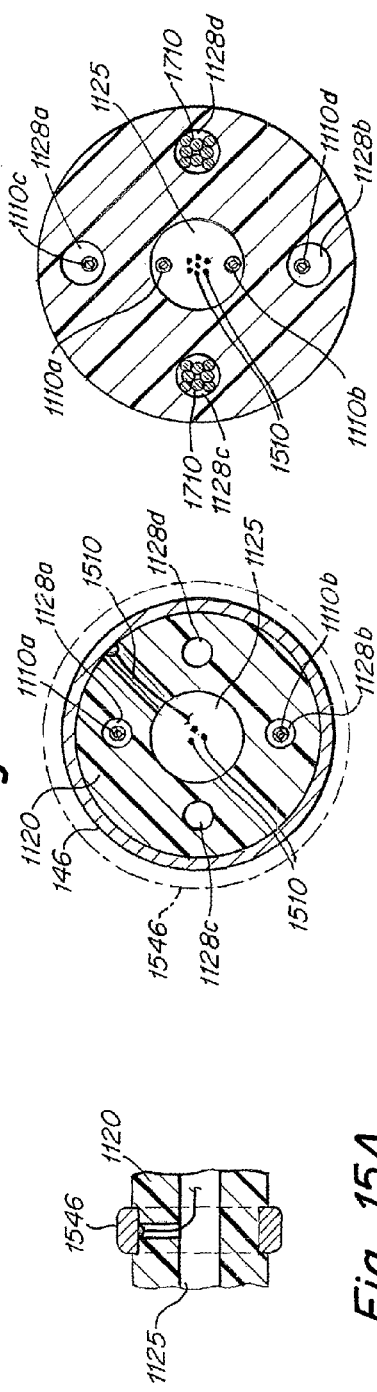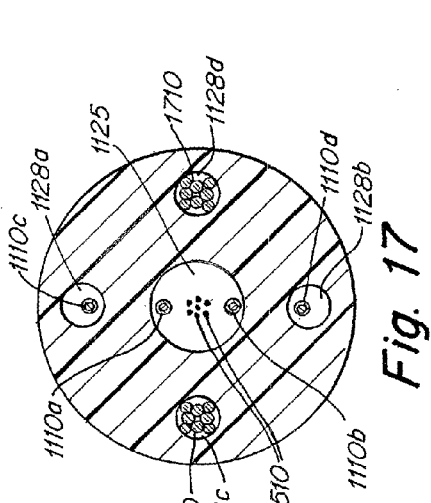
Fig. 14　Fig. 15　Fig. 15A　Fig. 16　Fig. 17

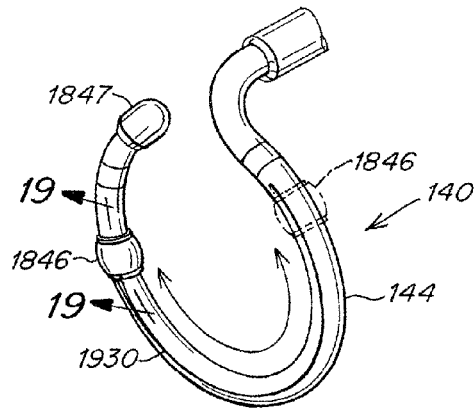
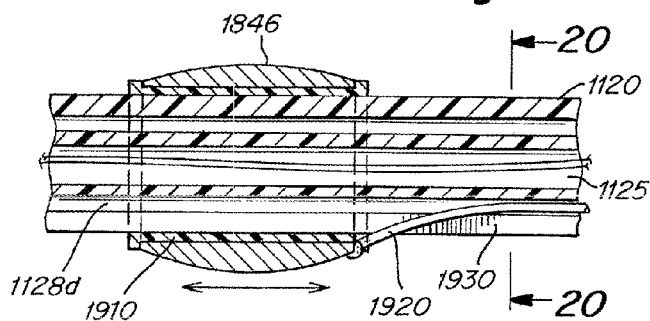
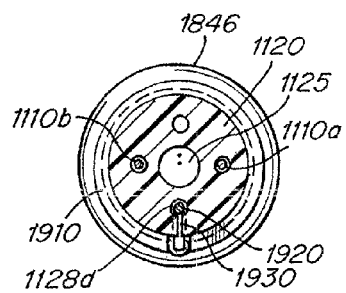
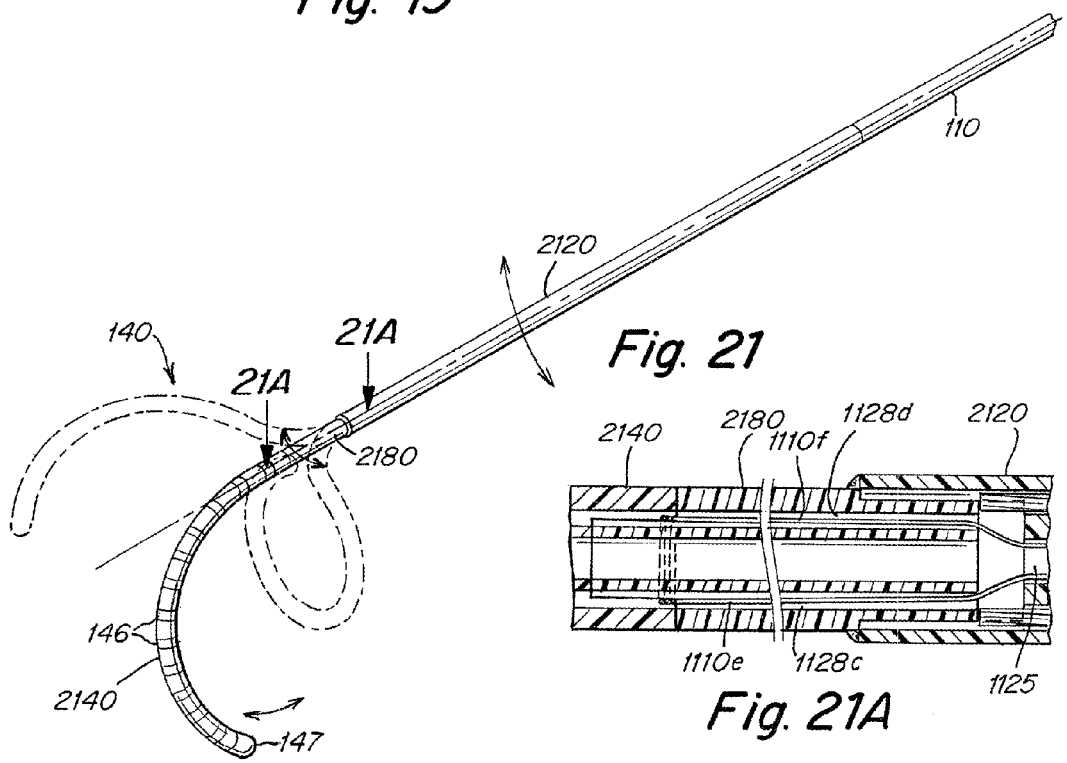

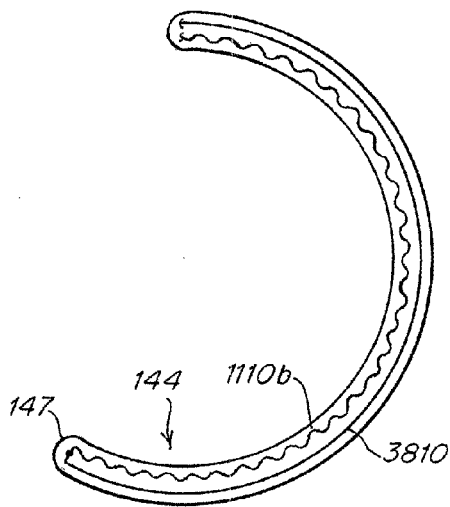
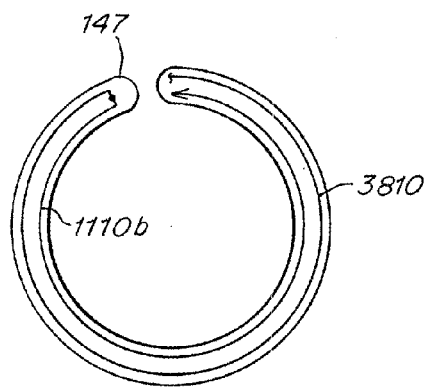
Fig. 41A
Fig. 41B
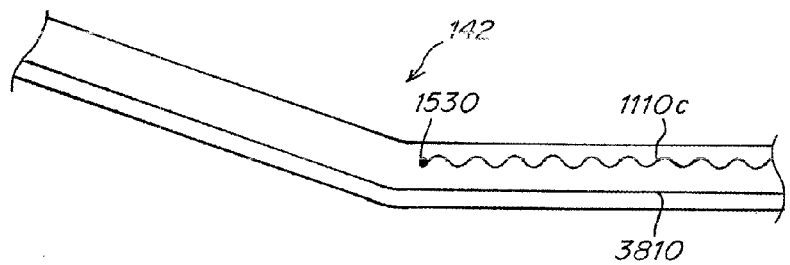
Fig. 42A
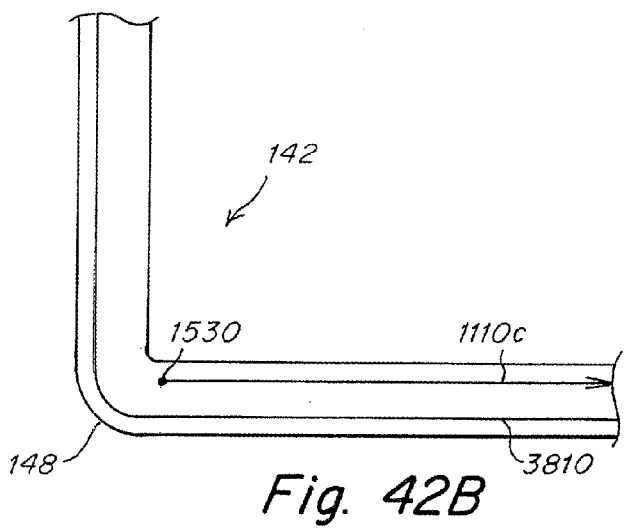
Fig. 42B

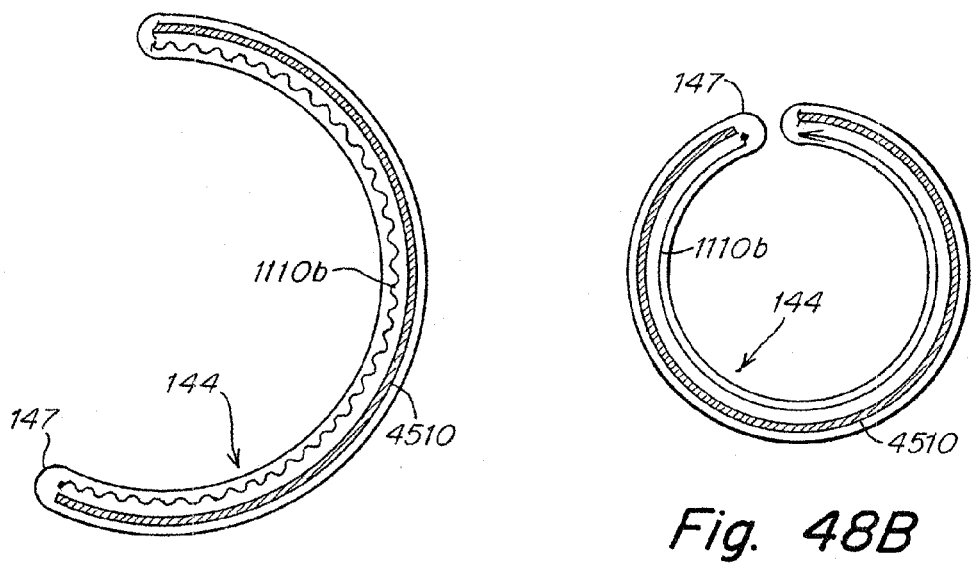
Fig. 48A
Fig. 48B
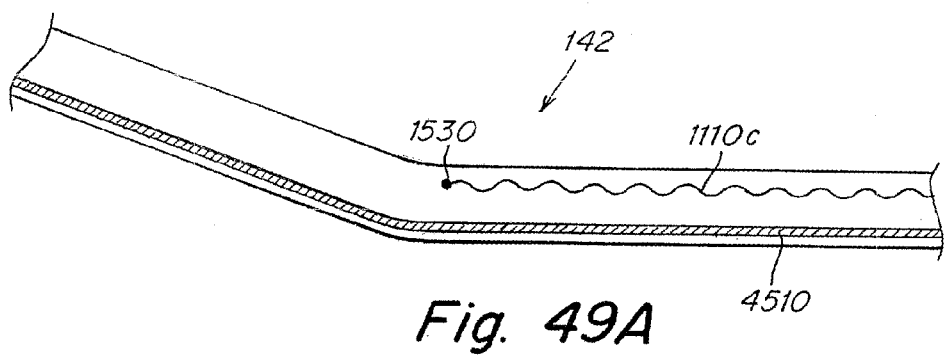
Fig. 49A
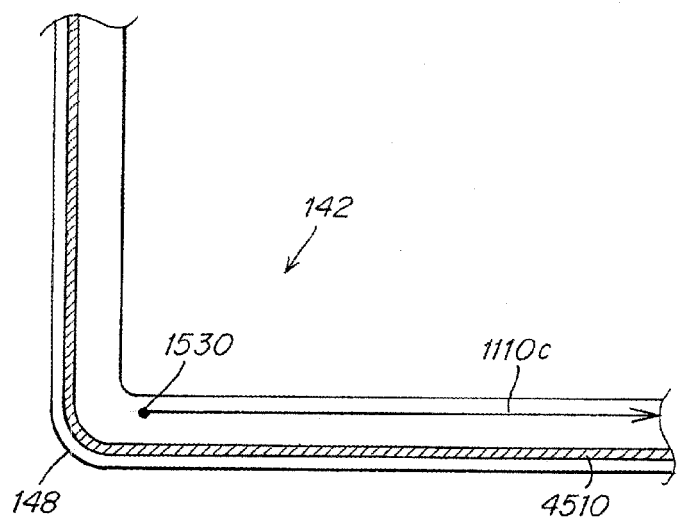
Fig. 49B

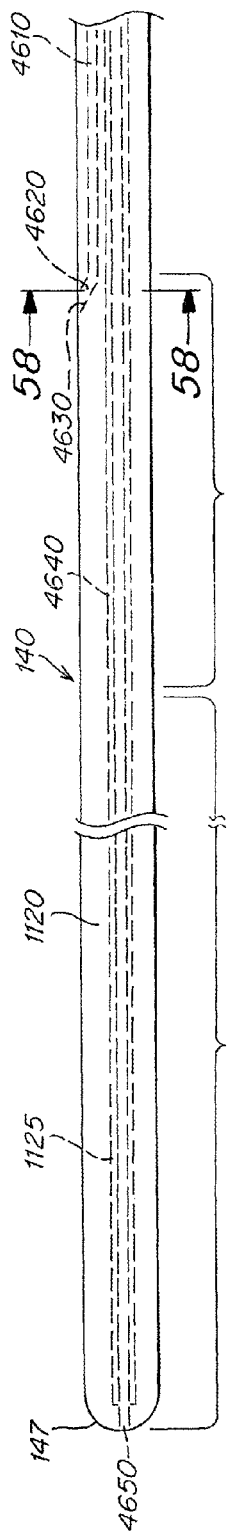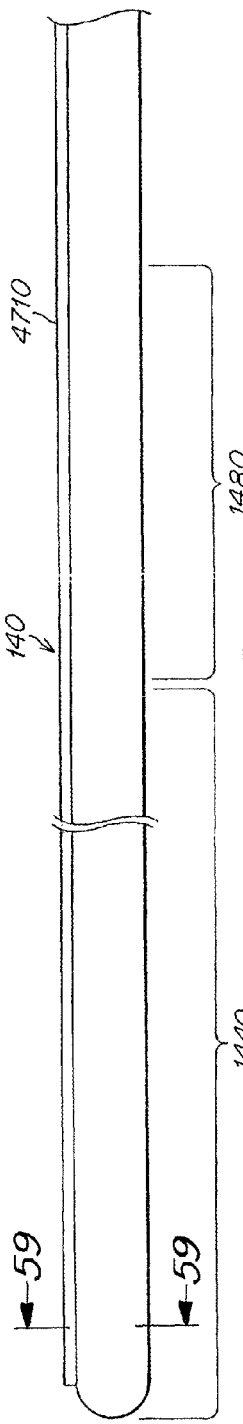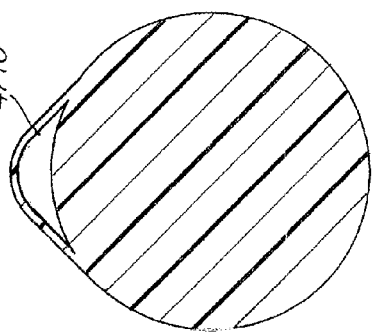
Fig. 59
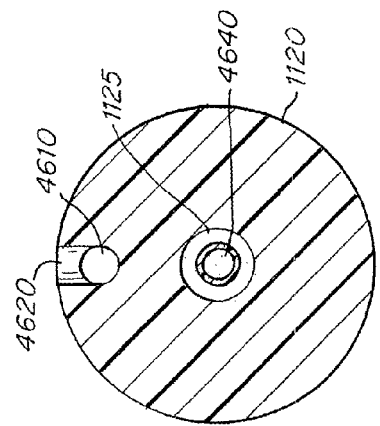
Fig. 58

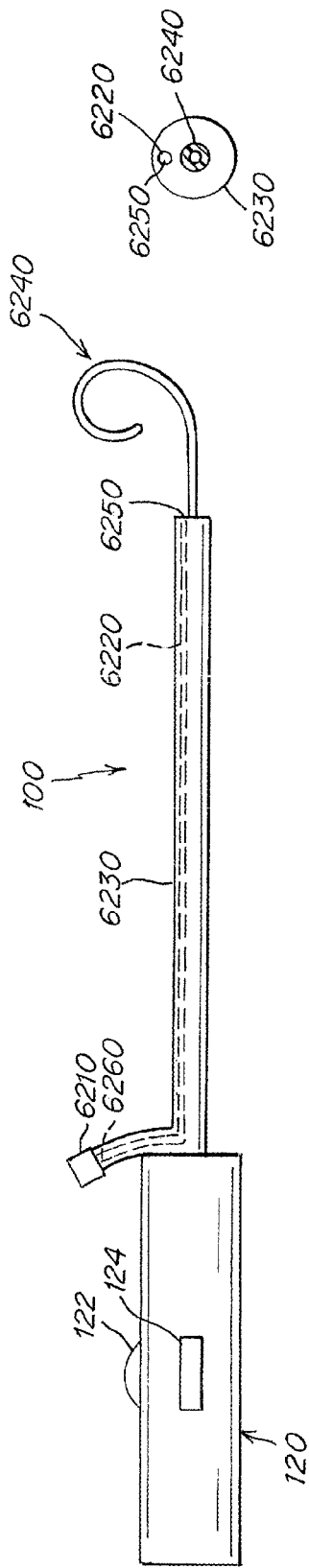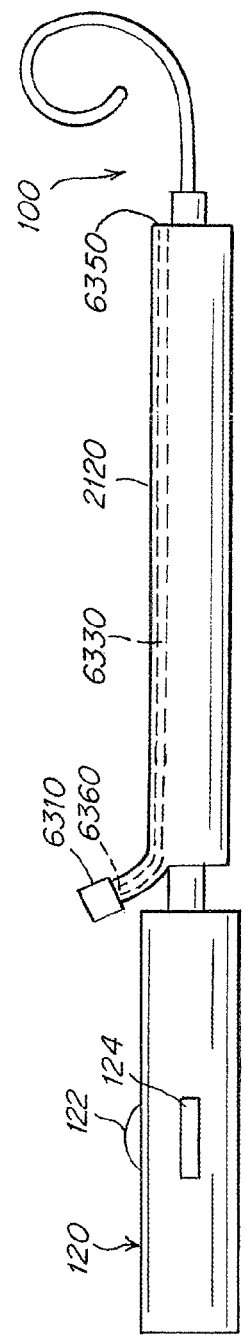

ELECTROPHYSIOLOGY LOOP CATHETER

RELATED APPLICATIONS

This application claims the benefit under 35 U.S.C. §120 as a divisional application of U.S. application Ser. No. 10/533,596, entitled "ELECTROPHYSIOLOGY LOOP CATHETER," filed on Jun. 26, 2006, which is a national stage application claiming the benefit under 35 U.S.C. §371 of International Application Serial No. PCT/US2003/34828, entitled "IMPROVED ELECTROPHYSIOLOGY LOOP CATHETER," filed on Oct. 21, 2003, which claims the benefit under 35 U.S.C. §119(e) of U.S. Provisional Application Ser. No. 60/422,707, entitled "ELECTROPHYSIOLOGY LOOP CATHETER," filed on Oct. 31, 2002, each of which is hereby incorporated by reference in its entirety.

BACKGROUND

1. Field of the Invention

This application describes electrophysiology catheters, and more particularly to electrophysiology catheters for performing endocardial mapping and/or ablation procedures.

2. Discussion of Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel and into an endocardial site, and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice.

Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

SUMMARY

One embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft, and the tip assembly including a wire formed of a superelastic material and shaped to bias the tip assembly in a first orientation, and a cable, attached to the actuator and the tip assembly, that extends through the shaft, the cable being adapted to change an orientation of the tip assembly from the first orientation in response to movement of the actuator.

Another embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, and a tip assembly having a proximal end and a distal end, the proximal end of the tip assembly being attached to the distal end of the shaft and the tip assembly including an adhesive cured in a configuration to bias the tip assembly in a first orientation.

A further embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft and the tip assembly including an adhesive cured in a configuration to support the tip assembly in a first orientation including an arcuately curved shape at the distal end of the tip assembly having a first radius of curvature, a first cable, attached to the actuator and the tip assembly, that extends through the shaft, the first cable being adapted to change an orientation of the tip assembly from the first orientation to a second orientation including an arcuately curved shape at the distal end of the tip assembly having a second radius of curvature larger than the first radius of curvature in response to movement of the actuator, and a second cable, attached to the actuator and the tip assembly, that extends through the shaft, the second cable being adapted to change the orientation of the tip assembly from the second orientation to the first orientation in response to movement of the actuator.

Another embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft and the tip assembly including an adhesive cured in a configuration to support the tip assembly in a first orientation including a bend at the proximal end of the tip assembly having a first angle of approximately ninety degrees relative to the longitudinal axis of the shaft, a first cable, attached to the actuator and the tip assembly, that extends through the shaft, the first cable being adapted to change an orientation of the tip assembly from the first orientation to a second orientation including a bend at the proximal end of the tip assembly having a second angle relative to the longitudinal axis that is smaller than the first angle in response to movement of the actuator, and a second cable, attached to the actuator and the tip assembly, that extends through the shaft, the second cable being adapted to change the orientation of the tip assembly from the second orientation to the first orientation in response to movement of the actuator.

A further embodiment described herein is directed to a method of shaping a tip assembly of a catheter. The method comprises acts of injecting an adhesive into a lumen of the catheter that extends along the tip assembly of the catheter, and curing the adhesive by maintaining a portion of the tip assembly of the catheter in a fixed position for a time sufficient to allow the adhesive to bias the tip assembly in a particular orientation.

Another embodiment described herein is directed to a method of using a catheter having a handle, a flexible shaft having a longitudinal axis, and a tip assembly, the shaft being connected between the handle and the tip assembly, a distal end of the tip assembly including an arcuate curve having a diameter. The method comprises acts of placing the tip assembly inside a heart of a patient, injecting a fluid from the tip assembly into the heart of the patient, and remotely, from outside the patient, adjusting the diameter of the arcuate curve.

A further embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft and the distal end of the tip assembly being biased in an arcuately curved shape having a radius of curvature, a cable, attached to the actuator and the distal end of the tip assembly, that extends through the shaft, the cable being adapted to change the radius of curvature of the distal end of the tip assembly in response to movement of the actuator, and means for conducting a fluid along a length of the shaft and releasing the fluid from the tip assembly.

Another embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft and the distal end of the tip assembly being biased in an arcuately curved shape having a radius of curvature, a cable, attached to the actuator and the distal end of the tip assembly, that extends through the shaft, the cable being adapted to change the radius of curvature of the distal end of the tip assembly in response to movement of the actuator, at least one lumen coupled to the shaft to conduct a fluid along a length of the shaft, and at least one opening in the lumen to release the fluid, the opening being disposed at a portion of the lumen coupled to the shaft at the tip assembly.

A further embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft and the distal end of the tip assembly being biased in an arcuately curved shape having a radius of curvature, and a cable, attached to the actuator and the distal end of the tip assembly, that extends through the shaft, the cable being adapted to change the radius of curvature of the distal end of the tip assembly in response to movement of the actuator, wherein the distal end of the tip assembly includes a plurality of position sensors disposed in the distal end of the tip assembly.

Another embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft, the proximal end of the tip assembly including a fixed bend of approximately ninety degrees relative to the longitudinal axis of the shaft, and the distal end of the tip assembly including an arcuate curve having a diameter, the arcuate curve being oriented in a plane that is approximately perpendicular to the longitudinal axis of the shaft, and a cable, attached to the actuator and the distal end of the tip assembly, that extends through the shaft, the cable being adapted to change the diameter of the arcuate curve in response to movement of the actuator, wherein the distal end of the tip assembly includes a plurality of position sensors disposed in the distal end of the tip assembly.

A further embodiment described herein is directed to a method of using a catheter having a handle, a flexible shaft having a longitudinal axis, and a tip assembly, the shaft being connected between the handle and the tip assembly, a distal end of the tip assembly including an arcuate curve having a diameter. The method comprises acts of placing the tip assembly inside a heart of a patient, sensing the location of at least one two points on the tip assembly, and remotely, from outside the patient, adjusting the diameter of the arcuate curve.

Another embodiment described herein is directed to a method of using a catheter having a handle, a flexible shaft having a longitudinal axis, and a tip assembly, the shaft being connected between the handle and the tip assembly, a distal end of the tip assembly including an arcuate curve having a diameter. The method comprises acts of placing the tip assembly inside a heart of a patient, sensing the location of a movable electrode disposed on the tip assembly, and remotely, from outside the patient, adjusting the diameter of the arcuate curve.

A further embodiment described herein is directed to an electrophysiology catheter comprising a handle having a distal end and a proximal end, the handle including a first actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft and the distal end of the tip assembly being biased in an arcuately curved shape having a radius of curvature, wherein the distal end of the tip assembly includes a movable electrode assembly comprising an electrode, a position sensor, and means for moving the electrode and position sensor longitudinally along a portion of the length of the shaft, and a first cable, attached to the first actuator and the distal end of the tip assembly, that extends through the shaft, the cable being adapted to change the radius of curvature of the distal end of the tip assembly in response to movement of the actuator in a first direction.

Another embodiment described herein is directed to a flexible shaft of a catheter device. The shaft comprises a catheter body having a proximal end and a distal end and a longitudinal axis that extends along a length of the catheter body, and a channel formed of a superelastic material and shaped to bias a portion of the catheter body in a first orientation.

A further embodiment described herein is directed to an electrophysiology catheter comprising a handle having a distal end and a proximal end, the handle including an actuator, a flexible shaft having a proximal end and a distal end and a longitudinal axis that extends along a length of the shaft, the proximal end of the shaft being attached to the distal end of the handle, a tip assembly having a proximal end and a distal end, the proximal end of the tip assembly being attached to the distal end of the shaft, and the tip assembly including a channel formed of a superelastic material and shaped to bias the tip assembly in a first orientation, and a cable, attached to the actuator and the tip assembly and extending through the channel, the cable being adapted to change an orientation of the tip assembly from the first orientation in response to movement of the actuator.

BRIEF DESCRIPTION OF THE DRAWINGS

Illustrative, non-limiting embodiments are described by way of example with reference to the accompanying drawings, in which:

FIG. 2 is an end elevational view of a distal end tip assembly, taken along line 2-2 in FIG. 1, that may be used with the catheter system of FIG. 1 according to one embodiment of the present invention;

FIG. 3 is a perspective view of the distal end tip assembly of FIG. 2;

FIG. 8 is an exploded perspective view of the jig of FIG. 7;

FIG. 9 is a cross sectional side view of a third jig that may be used to impart a fixed shape to the distal end of the tip assembly according to another embodiment of the present invention;

FIG. 10 is an exploded perspective view of the jig of FIG. 9;

FIG. 14 is a side elevational view of the distal end of a finished catheter prior to shaping with any one of the jigs of FIGS. 5-10;

FIG. 15 is a cross sectional view of the distal end of the catheter of FIG. 14 taken along line 15-15 in FIG. 14;

FIG. 15A is a fragmentary cross sectional view of the distal end of the catheter of FIG. 15 showing an alternative raised profile electrode;

FIG. 16 is a cross sectional view of the distal end of the catheter of FIG. 15 taken along line 16-16 in FIG. 15;

FIG. 17 is a cross sectional view of the distal end of the catheter of FIG. 15 taken along line 17-17 in FIG. 15;

FIG. 18 is a perspective view of a distal end tip assembly according to another embodiment that may be used with the catheter system of FIG. 1, and which includes a sliding electrode;

FIG. 19 is a cross sectional side view of the distal end tip assembly of FIG. 18 taken along line 19-19 in FIG. 18;

FIG. 20 is a cross sectional end view of the distal end of tip assembly of FIG. 19 taken along line 20-20 in FIG. 19;

FIG. 21 is a perspective view of a distal end tip assembly according to another embodiment that may be used with the catheter system of FIG. 1;

FIG. 21A is a cross sectional view of the distal end tip assembly of FIG. 21 taken along line 21A-21A in FIG. 21;

FIGS. 41A and 41B are schematic views illustrating a second configuration for controlling the distal end of the tip assembly with a superelastic wire and a pull wire;

FIGS. 42A and 42B are schematic views illustrating a second configuration for controlling the proximal end of the tip assembly with a superelastic wire and a pull wire;

FIGS. 48A and 48B are schematic views illustrating a second configuration for controlling the distal end of the tip assembly with a cured adhesive and a pull wire;

FIGS. 49A and 49B are schematic views illustrating a second configuration for controlling the proximal end of the tip assembly with a cured adhesive and a pull wire;

FIG. 56 is a side view of a tip assembly including a fluid delivery structure in accordance with another embodiment of the present invention;

FIG. 57 is a side view of a tip assembly including a fluid delivery structure in accordance with further embodiment of the present invention;

FIG. 58 is a cross sectional view of the tip assembly of FIG. 56 taken along line 58-58 in FIG. 56;

FIG. 59 is a cross sectional view of the tip assembly of FIG. 57 taken along line 59-59 in FIG. 57;

FIGS. 62A and 62B illustrate a catheter including a fluid delivery structure in accordance with another embodiment of the present invention;

FIG. 63 illustrates a sheath including a fluid delivery structure in accordance with an embodiment of the present invention;

DETAILED DESCRIPTION

In this description, various aspects and features of the present invention will be described. One skilled in the art will appreciate that the features may be selectively combined in a device depending on the particular application. Furthermore, any of the various features may be incorporated in a catheter and associated method of use for mapping and/or ablation procedures.

Catheter Overview

Figure 1:
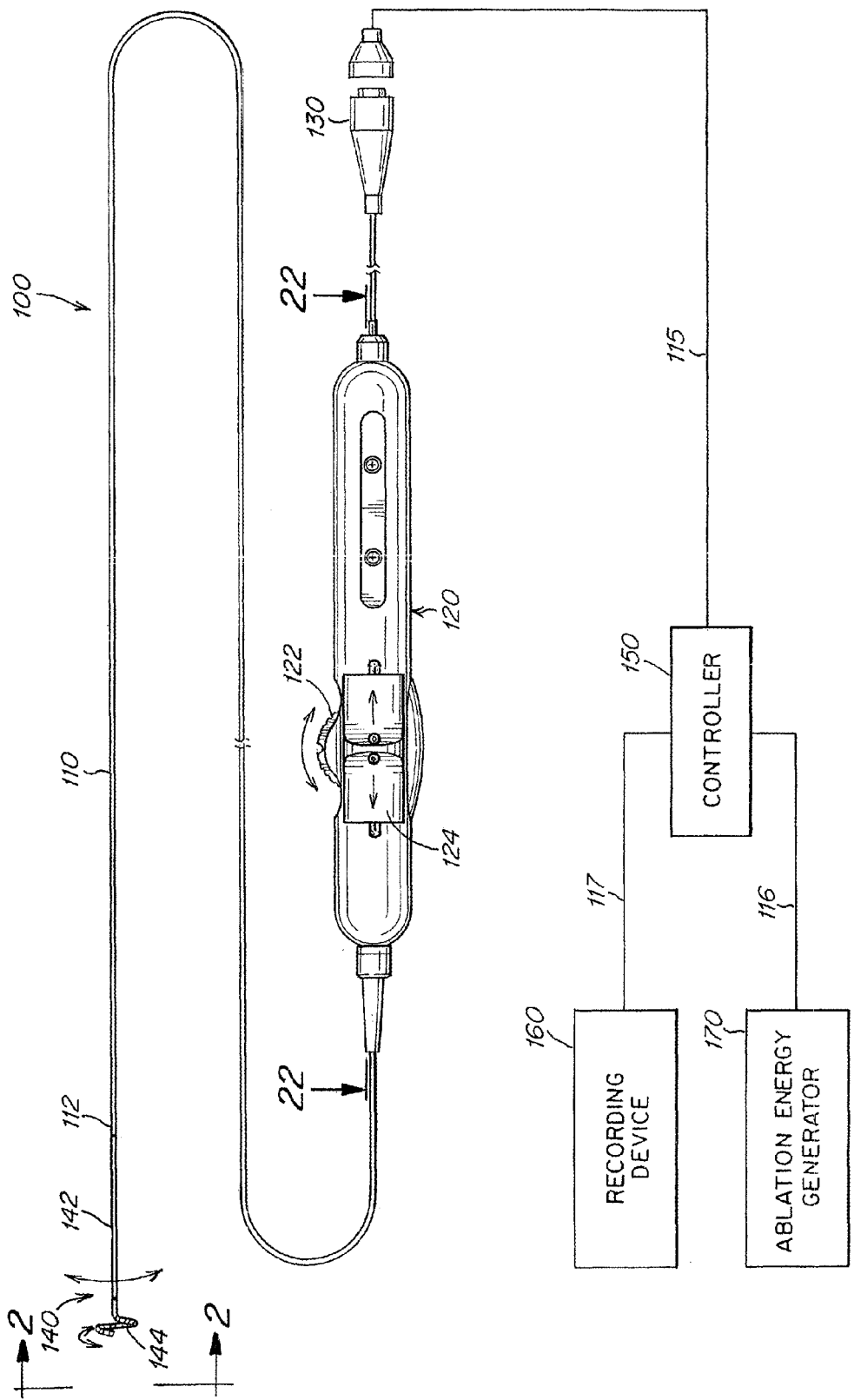
FIG. 1 illustrates a schematic view of a mapping and/or ablation catheter system in accordance with the present invention.

Reference is now made to FIG. 1, which illustrates an overview of a mapping and/or ablation catheter system for use in electrophysiology procedures, in accordance with the present invention. The system includes a catheter 100 having a flexible shaft 110, a control handle 120, and a connector 130. When used in mapping applications, the connector 130 is used to allow signal wires running from mapping electrodes at a distal end of the catheter 100 to be connected to a device for recording signals, such as a recording device 160. When used in ablation applications, connector 130 is used to allow signal wires running from ablation electrodes at the distal end of the catheter 100 to be connected to a device for generating ablation energy, such as ablation energy generator 170. As will be described further in detail below, the distal end of the catheter 100 may include separate mapping and/or ablation electrodes, or may alternatively include electrodes that are adapted for both mapping and ablation.

A controller 150 is electrically connected to connector 130 via cable 115. In one embodiment, controller 150 may be a QUADRAPULSE RF CONTROLLER™ device available from C.R. Bard, Inc., Murray Hill, N.J. Ablation energy generator 170 may be connected to controller 150 via cable 116. Recording device 160 may be connected to controller 150 via cable 117. When used in an ablation application, controller 150 is used to control ablation energy, provided by ablation energy generator 170, to catheter 100. When used in a mapping application, controller 150 is used to process signals from catheter 100 and provide these signals to recording device 160. Although illustrated as separate devices, recording device 160, ablation energy generator 170, and controller 150 may be incorporated into a single device. It should further be appreciated that although both ablation energy generator 170 and recording device 160 are illustrated in FIG. 1, either or both of these devices may be incorporated in the catheter system in accordance with the present invention.

The shaft 110 of the catheter 100 is, in one embodiment, approximately six French in diameter, although it should be appreciated that many diameters are possible, and the diameter of shaft 110 may be smaller or larger depending on the particular application and/or combination of features incorporated into the catheter 100. Attached to a distal end 112 of the shaft 110 is a distal end tip assembly 140 having a proximal end 142 that is attached to the distal end 112 of the shaft 110, and a distal end 144 having one or more electrodes 146 (See FIG. 2). The length of the tip assembly 140 may be approximately 7 to 8 cm in length, although other lengths may be suitably employed, as the present invention is not limited to any particular length. Further, and as will be subsequently described, the number and placement of electrodes along the distal end 144 of the tip assembly 140 may vary depending upon the application. For example, for mapping applications, a plurality of low profile electrodes may be preferred, whereas for ablations applications a lesser number of higher profile electrodes may be preferred. Embodiments may include as few as one electrode, which may be movably attached to the distal end 144 of the tip assembly 140, or may alternatively include a plurality of fixed electrodes, for example 20 or more, spaced apart along the distal end 142 of the tip assembly 140. Further, the construction of the electrode or electrodes 146 may vary, as known to those skilled in the art.

According to one aspect of the present invention, and as shown in detail in FIG. 3, the proximal end 142 of the tip assembly 140 includes an approximately ninety degree bend 148 relative to a longitudinal axis (L) of the shaft 110, which may be active, or fixed, and the distal end 144 of the tip assembly 140 includes an arcuate curve that is oriented orthogonally to the longitudinal axis of the shaft 110. As used in association with the approximately ninety degree bend 148, the term "active" is herein defined to mean that the portion of the proximal end 142 of the tip assembly 140 where the bend 148 is formed is capable of movement, relative to the longitudinal axis (L) of the shaft 110 between approximately zero degrees and approximately ninety degrees via manipulation of a remotely controlled actuator (e.g., actuators 122, 124 disposed on the handle 120). The term "fixed," as used in association with the approximately ninety degree bend 148, is herein defined to mean that the approximately ninety degree bend 148 is permanently formed in the proximal end 142 of the tip assembly 140, such that the approximately ninety degree bend retains its shape at body temperatures.

According to a further aspect of the present invention, the radius (or alternatively, the diameter) of curvature of the arcuately curved distal end 144 may be adjustable by operation of an actuator (e.g., actuators 122, 124) disposed on the handle 120. The combination of the approximate ninety degree bend followed by an arcuate curve that is adjustable in diameter permits the catheter 100 to be uniquely suited for mapping and/or ablation procedures in difficult endocardial sites, such as, for example, within a blood vessel, such as a pulmonary vein, or an ostium of a blood vessel, such as the ostium of a pulmonary vein. For example, in both mapping and ablation procedures, the approximately ninety degree bend permits pressure, applied to the handle 120, to be translated to the distal end 144 of the tip assembly 142, to thereby urge the distal end 144 of the tip assembly 140 tight against the endocardial site. The adjustable radius of curvature of the arcuate curve can be used to apply an outwardly radial pressure to further force the distal end 144 of the tip assembly 140 tight against the endocardial site, or to adjust to endocardial sites of different diameters (e.g. that of an adult or large animal, or a small child or small animal), or both. This ability to urge the distal end 144 of the tip assembly tight against an endocardial site is advantageous in mapping procedures to better localize the source of the cardiac arrhythmia, and may be used in ablation procedures to focus the ablation energy on the selected endocardial site. Further, because the radius of curvature of the distal end 144 of the tip assembly can be adjusted to different diameters, the catheter may be used with either an adult (or large animal) or a child (or small animal), as "one size fits all." This ability to accommodate a range of sizes can reduce the number of distinctly sized catheters that need to be stocked by the manufacturer or the care provider.

Disposed on the handle 120 are one or more actuators 122, 124 that may be used for a variety of purposes. Each of the actuators 122, 124 is mechanically coupled to at least one cable that extends to the tip assembly 140 and which may be used to change the shape, orientation, or both the shape and orientation of the tip assembly. In the embodiment depicted in FIG. 1, the handle 120 includes two different actuators, a thumbwheel actuator 122 and a slide actuator 124. In one embodiment, the thumbwheel actuator 122 may be used to change the orientation of the tip assembly 140 in two opposing directions, and the slide actuator 124 may be used to enlarge and decrease the radius of curvature of the arcuately curved distal end 144 of the tip assembly 140. As will be described in detail further below, the operation of the actuators 122, 124 may be reversed, such that the thumbwheel actuator 122 is used to control the radius of curvature, and the slide actuator 124 is used to control the orientation of the tip assembly 140 relative to the shaft 110 (e.g., to provide steering). Moreover, as described further in detail below, the present invention is not limited to two distinct control actuators, as embodiments may include only a single actuator that controls only one degree of movement (for example, increasing the radius of curvature of the arcuately curved distal end 144), or may include several actuators, each capable of controlling two degrees of movement.

The Tip Assembly

Figure 4:
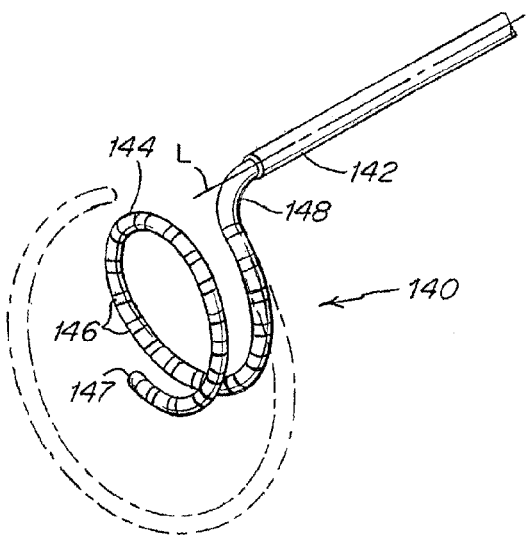
FIG. 4 is an alternative perspective view of the distal end tip assembly of FIG. 2 illustrating the manner in which the radius of curvature of the distal end may be changed.

FIGS. 2-4 illustrate a distal end tip assembly according to one embodiment of the present invention. According to this embodiment, the proximal end 142 of the tip assembly 140 includes an approximately ninety degree bend 148 relative to the longitudinal axis of the shaft 110, followed by an arcuately curved distal end 144. In the embodiment depicted in FIGS. 2-4, the approximately ninety degree bend 148 is fixed, that is, permanently formed in the proximal end 142 of the tip assembly 140, such that the approximately ninety degree bend 148 retains its shape at body temperatures. In other embodiments, the approximately ninety degree bend 148 may be active, that is, movable between approximately zero and approximately ninety degrees relative to the longitudinal axis (L) of the shaft 110 via a pull or push cable attached to one of the actuators 122, 124 on the handle 120, as described further below with respect to FIG. 21.

In each embodiment, the region of the tip assembly 140 that includes the approximately ninety degree bend 148 is preferably biased in a curved position relative to the longitudinal axis (L) of the shaft 110, although the degree of bias may vary. Specifically, in embodiments featuring a fixed bend, the bend 148 is permanently formed in the proximal end 142 of the tip assembly 140 at an angle of approximately ninety degrees, such that while capable of being straightened for introduction into a vessel, such as for example, through the use of a sheath/dilator, the distal end 144 of the tip assembly 140 springs back in its unrestrained state to rest in a plane that is approximately perpendicular to the longitudinal axis (L) of the shaft 110. In embodiments featuring an active bend, only a slight amount of bend, for example, a few degrees, is permanently formed in the proximal end 142 of the tip assembly 140. This slight amount of bend in the proximal end 142 of the tip assembly 140 is sufficient to ensure that the distal end 144 of the tip assembly 140 bends in a predetermined direction relative to the longitudinal axis (L) of the shaft 110, as described more fully below. However, in all embodiments, the distal end 144 of the tip assembly 140 is permanently biased in an arcuate shape to facilitate increases and/or decreases in the radius of curvature of the distal end 144 of the tip assembly 140 in a known and controlled manner.

Disposed on the arcuately curved distal end 144 of the tip assembly 140 are a plurality of ring-shaped electrodes 146 spaced uniformly apart along the distal end 144 and a distal end tip electrode 147. Although illustrated as being uniformly spaced apart on the distal end 144 of the tip assembly 140, the electrodes 146 may alternatively be grouped in pairs, with the distance between each electrode of a pair being closer than the distance between electrodes of adjacent pairs. For example, each ring electrode may be approximately 1 mm in length, with pairs of electrodes being spaced approximately 2 mm apart on center, and with electrodes of adjacent pairs being spaced apart by approximately 8 mm. Furthermore, although the electrodes 146 illustrated in FIG. 2 are shown as being low profile ring electrodes that conform to the surface of the distal end 144 of the tip assembly 140, they may also be raised in profile. Indeed, as described further in detail below, embodiments may be used with any type of electrode that is suitable for use in endocardial or epicardial mapping and/or ablation procedures, as the present invention is not limited to the number, the construction, or placement of electrodes on the distal end 144 of the tip assembly 140.

According to an embodiment of the present invention, the tip assembly 140 may be made from an elastomeric or polymeric thermodynamic bio-compatible material, such as PEBAX, that is bonded onto the distal end 112 of the flexible shaft 110, which may also be made from an elastomeric or polymeric thermodynamic bio-compatible material. Examples of materials that may be used to form the flexible shaft 110 and the tip assembly 140 are well known in the art, and are described, for example, in commonly assigned U.S. Pat. Nos. 5,383,852, 5,462,527, and 5,611,777, which are hereby incorporated by reference in their entirety.

According to one embodiment, the flexible shaft 110 may be made from a material that is stiffer than the material used to form the proximal end 142 of the tip assembly 140, and the tip assembly 140 may be formed from a variety of bio-compatible materials that have different degrees of stiffness. For example, in one embodiment, the flexible shaft 110 is made from a material having a hardness of approximately 60 Shore D, the proximal end 142 of the tip assembly is made from a material having a hardness of approximately 45-50 Shore D, and the arcuately curved distal end 144 is made from a material having a hardness of approximately 40 Shore D. The increased stiffness of the shaft 110 permits pressure applied to the handle 120 to be more directly translated to the tip assembly 140. Further, the intermediate stiffness of the proximal end 142 of the tip assembly 140 permits movement (i.e., steering) of the tip assembly 140 (described further below) while ensuring that pressure applied to the handle 120 is translated via the shaft 110 to the distal end 144 of the tip assembly 140 to urge the distal end 144 of the tip assembly 140 tight against an endocardial site. Such enhanced contact is advantageous in both mapping and ablation procedures. Further, the relative flexibility of the material from which the distal end 144 of the tip assembly 140 is formed permits the diameter of the arcuately curved distal end 144 of the tip assembly 140 to be changed (increased, decreased, or both) via manipulation of one of the actuators 122, 124 on the handle 120. In another embodiment, the flexible shaft 110 is made from a material having the same degree of hardness as the proximal end 142 of the tip assembly, for example, 45050 Shore D, but the flexible shaft 110 has a larger diameter, and is thus stiffer than the proximal end 142.

To further enhance contact with the endocardial site, the proximal end 142 of the tip assembly 140 may be stiffened, for example with an outer stiffening tube (not shown), just ahead (i.e., proximally) of the approximately ninety degree bend 148. For example, where the tip assembly 140 includes a fixed bend of approximately ninety degrees, the material forming the approximately ninety degree bend 148 may be sufficiently stiffer than that from which the distal end 144 is formed, to further enhance contact with an endocardial or epicardial site.

Although embodiments are not limited to any particular length, in one embodiment of the present invention, the length of the flexible shaft is approximately one meter, the length of the proximal end 140 of the tip assembly is approximately 4.5 cm, the length of the distal end 144 of the tip assembly is approximately 6.5 cm, and the length of the approximately ninety degree bend portion is approximately 0.7 cm. It should of course be appreciated that lengths of the different portions of the catheter may be varied, dependent upon the endocardial or epicardial site of interest.

As shown in FIG. 3, the tip assembly 140 may be movable (i.e., steerable) in one or more directions perpendicular to the longitudinal axis of the shaft 110. For example, as illustrated in the embodiment of FIG. 3, the tip assembly 140 is capable of movement in two opposite directions (shown as the Z axis) relative to the longitudinal axis of the shaft via manipulation of one of the actuators 122, 124 on the handle 120 (FIG. 1). In other embodiments, the tip assembly may be moved in only a single direction (e.g., in the positive Z direction), or in a number of different directions (e.g., in the positive and negative Z directions, and the positive and negative Y directions).

As also shown in FIG. 3, and according to one aspect of the present invention, the radius (or alternatively, the diameter) of curvature of the arcuately curved distal end 144 of the tip assembly 140 may be changed from a first diameter D1 to a second diameter D2. Preferably, the radius of curvature of the arcuately curved distal end 144 of the tip assembly 140 may be increased and decreased via manipulation of one of the actuators 122, 124 disposed on the handle 120. This ability to both increase and decrease the radius of curvature of the distal end 144 of the tip assembly 140 permits a single tip assembly 140 to be used in a wide variety of applications and with a wide variety of patients (from adults or large animals to children or small animals), as it can be adjusted to different diameters to suit the requirements of the patient and the particular medical procedure. It also permits a radially outward force, or alternatively, a radially inward force, to be applied to an endocardial or epicardial site.

According to one embodiment of the present invention, the diameter of the arcuately curved distal end of the tip assembly is approximately 20 mm in a resting state (corresponding to a neutral position of the actuator 122, 124 that controls the radius of curvature of the distal end 144 of the tip assembly 140), but may be decreased to a diameter of approximately 5 mm and increased to a diameter of approximately 50 mm via manipulation of one of the actuators 122, 124. According to this embodiment, the diameter of approximately 20 mm corresponds to an approximately closed circle shown in FIGS. 2 and 3. The diameter of approximately 50 mm corresponds approximately to a semicircle, shown in phantom in FIG. 3, and the diameter of approximately 5 mm corresponds to more than one complete circle (i.e., a spiraling of the distal end) as shown in FIG. 4. Although the present invention is not limited to any particular diameter for the distal end 144 of the tip assembly 140, these dimensions permit the catheter 100 to be well suited for use in mapping and/or ablation procedures relating to blood vessels where focal triggers may be present, such as a pulmonary vein. For example, a diameter of approximately 5 to 50 mm permits the tip assembly to be used for mapping and/or ablation procedures relating to the ostium of a pulmonary vein where focal triggers for cardiac arrythmias may frequently be encountered. These dimensions also permit a single tip assembly 140 to be used in either large or small humans or animals, and for a wide variety of different procedures. It should be appreciated that the above-described dimensions for the diameter of the arcuately curved distal end of the tip assembly correspond to a radius of curvature that is one half that of the indicated diameter (i.e., a diameter of 50 mm corresponds to a radius of curvature of 25 mm, etc.).

Although the radius of curvature of the distal end 144 of the tip assembly 140 described with respect to FIG. 3 is preferably capable of being increased or decreased, the present invention is not so limited. For example, in certain embodiments, the radius of curvature may be changed in only first direction (e.g., increased), while in other embodiments, the radius of curvature may only be changed in a second direction (e.g., decreased). However, in each of the above described embodiments, the distal end 144 of the tip assembly 140 is preferably permanently biased into an arcuate shape in its resting state so that the increase and/or decrease in the radius of curvature is achieved in a known and controlled manner.

Steering and Control of the Tip Assembly

Figure 11:
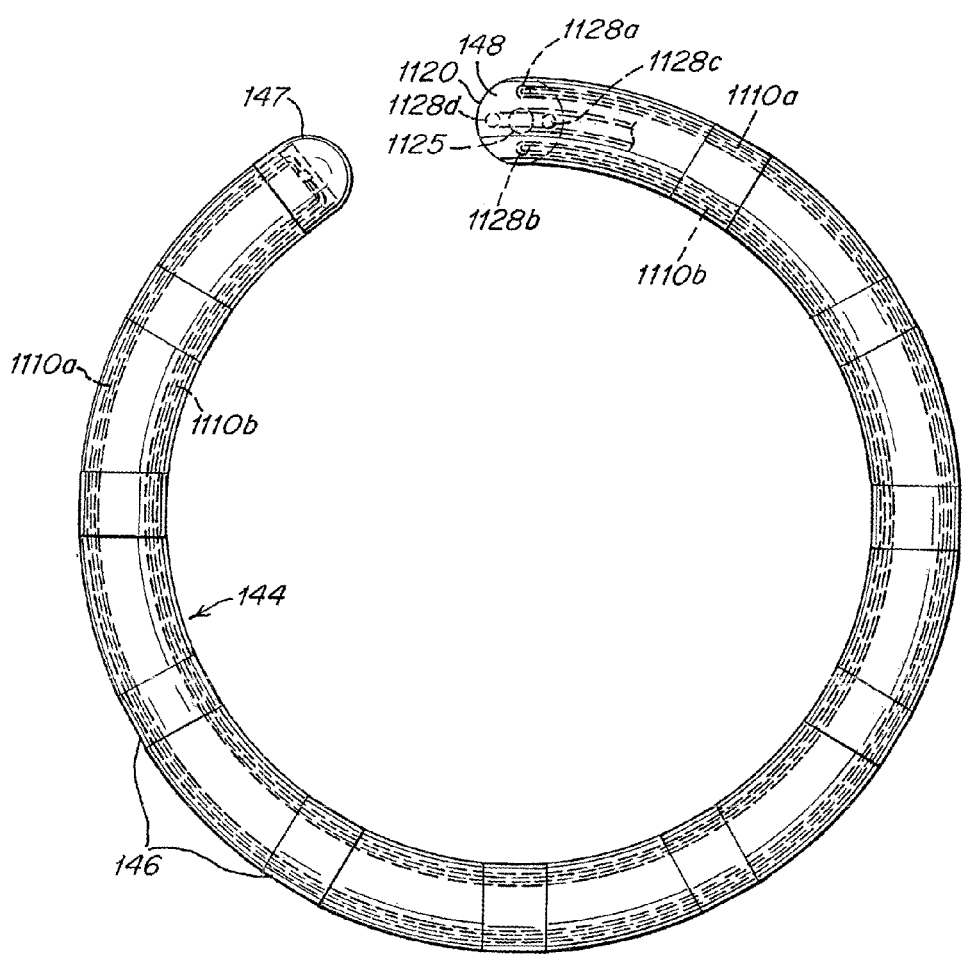
FIG. 11 is an enlarged end elevational view of the distal end tip assembly of FIG. 2.

FIG. 11 is an enlarged end elevational view of the distal end tip assembly 140 of FIG. 2. As shown in FIG. 11, in one embodiment of the present invention, the distal end 144 of the tip assembly 140 includes a pair of cables 1110a, 1110b that may be used to change the radius (or alternatively, the diameter) of curvature of the distal end 144 of the tip assembly from a first diameter to a second diameter. In the embodiment illustrated in FIG. 11, the tip assembly includes a core 1120 that includes a plurality of lumens, including a central lumen 1125, and four coaxial lumens 1128a-d disposed about the central lumen 1125. The central lumen 1125 is used to hold one or more electrically conductive wires (not shown in FIG. 11) that are attached to respective electrodes 146, 147 disposed along the distal end 144 of the tip assembly 140. The four coaxial lumens 1128a-d may be used to hold cables that control the orientation of the tip assembly 140 relative to the shaft 110, and that control the radius of curvature of the distal end 144 of the tip assembly 140. As illustrated in FIG. 11, two cables 1110a and 1110b extend along the length of the distal end 144 of the tip assembly 140, while the two other cables (not shown) terminate prior to the distal end 144. In the embodiment depicted in FIG. 11, the ends of the two cables 1110a and 1110b are tied together and potted with an epoxy adjacent the most distal end of the tip assembly 140. In this embodiment, the cables 1110a and 1110b are used to control the radius of curvature of the distal end 144 of the tip assembly 140.

Although the tip assembly is described as including a core 1120 that includes a plurality of lumens 1125 and 1128a-d, it should be appreciated that the tip assembly may be constructed in other ways. For example, U.S. Pat. Nos. 5,383, 852, 5,462,527, and 5,611,777 describe alternative constructions for the distal end of a catheter, some of which include a central lumen that holds both the electrode wires and the pull cables. This alternative construction of the distal end tip assembly may also be used with embodiments of the present invention, as the present invention is not limited to any particular construction.

Figure 12:
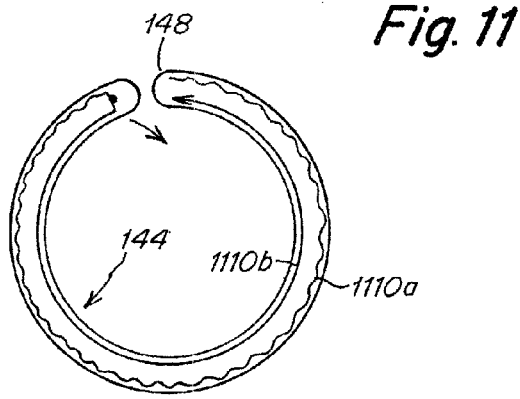
FIG. 12 is a schematic view of the distal end tip assembly of FIG. 11 in a tightly coiled position.
Figure 13:
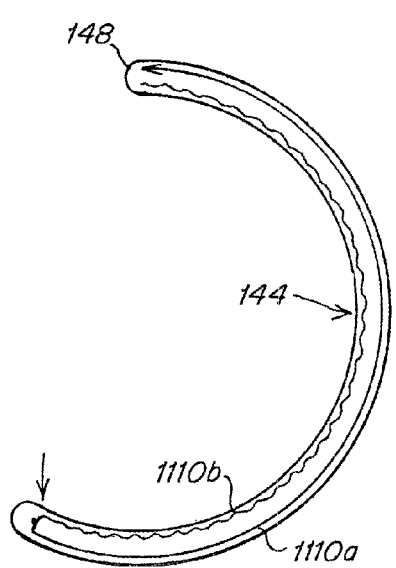
FIG. 13 is a schematic view of the distal end tip assembly of FIG. 11 in a loosely coiled position.

FIGS. 12 and 13 illustrate how the radius of curvature of the distal end 144 of the tip assembly 140 may be changed via manipulation of the cables 1110a, 1110b that are attached to one or more of the actuators 122, 124 on the handle 120 (FIG. 1). In the embodiment illustrated, cables 1110a and 1110d are pull cables that may be formed, for example, from stainless steel wire or any other suitable material. Where the catheter 100 is to be used in an environment where large magnetic fields may be present, for example, in an MRI chamber, each of the cables (and indeed, the electrodes 146, 147) may be made from non-ferromagnetic materials. For example, the electrodes may be made from electrically conductive non-ferromagnetic materials such as platinum, silver, or gold, while the cables may be made from composite materials, such as carbon fiber, or KEVLAR™, or a multiplicity of ultra-high molecular weight polyethelene filaments. It should be appreciated that the cables 1110a and 1110b may alternatively be used as push cables, although the use of push cables generally requires a more rigid and oftentimes larger diameter cable than that required for a pull cable, which is operative under tension, rather than compression. As an example, the diameter of the pull cables may be in the range of 0.003 to 0.004 inches.

As shown in FIGS. 12 and 13, tension applied to cable 1110b results in a decrease in the diameter of curvature of the distal end 144 of the tip assembly 140 (and a corresponding slack in the cable 1110a), while tension applied to cable 1110a results in an increase in the diameter of curvature of the distal end 144 of the tip assembly 140.

FIG. 14 is a side elevational view of the distal end of a finished catheter 100 prior to shaping with any one of the jigs described with respect to FIGS. 5-10 below. According to one embodiment of the present invention, the tip assembly 140 may be formed from several different sections that are bonded together and to the shaft 110. The formation of the tip assembly in sections permits greater control of the diameter and stiffness of various sections. As illustrated in FIG. 14, these sections may include a proximal section 1420 that is bonded to the flexible shaft 110, an intermediate section 1480 which may be shaped to bend approximately ninety degrees relative to the shaft 110 and which is bonded to the proximal section 1420, and a distal section 1440 that is bonded to the intermediate section 1480 and which includes a plurality of electrodes and a distal end tip or cap electrode 147.

FIG. 15 is a cross sectional view of the distal end tip assembly 140 of FIG. 14 taken along line 15-15 in FIG. 14. According to one embodiment of the present invention, the tip assembly 140 comprises a tubular proximal section 1420 and a tubular distal section 1440 aligned coaxially with the shaft 110. Between the proximal section 1420 and the distal section 1440 is an intermediate section 1480 that may be shaped to bend approximately ninety degrees relative to the shaft 110. As illustrated, in one embodiment, the proximal section 1420 may be of approximately the same outer diameter as the shaft 110, and the distal section 144 and the intermediate section 1480 can also be of approximately the same outer diameter, but a slightly smaller diameter than the proximal section 1420 and the shaft 110. In other embodiments, the various sections forming the tip assembly 140 may be of the same outer diameter as the shaft 110.

In the illustrated embodiment, the distal section 1440 of the tip assembly 140 terminates in a distal end or cap electrode 147 which is also coaxially aligned with the shaft 110 and sections 1420, 1440, and 1480. A threaded collar 1520 is secured to the distal end of distal section 1440 to retain the electrode cap 147. It should be appreciated that other embodiments need not include the threaded collar 1520 and the distal end or cap electrode 147, and may for example, instead utilize a non-conductive cap.

Shaft 110 may include a single lumen 1525 which extends the length of the shaft 110 from the distal end of the handle 120. The single-lumen 1525 may be used to house the pull cables 1128a-d and the electrode wires 1510. Each pull cable and each electrode wire preferably includes a sheath.

The electrical portion of the tip assembly 140 may include a plurality spaced ring-type electrodes 146 along with a distal end or cap electrode 147. The electrodes provide signal information on heart potentials to the remote recording device 160 (FIG. 1) used by the electrophysiologist. The ring-type electrodes 146 and the cap electrode 147 are electrically connected to respective signal wires 1510. The signal wires 1510 are routed through the length of the core 1120 through a central lumen 1125 in each of the proximal 1420, intermediate 1480, and distal 1440 sections, as illustrated in FIGS. 15, 16, and 17 and attached to a respective electrode 146, 147. The signal wires 1510 are preferably electrically insulated from each other and therefore may all share a single lumen as shown. The signal wires 1510 extend proximally through the handle 120 to the connector 130 which enables the electrodes 146 and 147 to be easily coupled electrically to the recording device 160. In the illustrated embodiment, the two pull cables 1110a and 1110b that extend nearly the length of the tip assembly 140 are used to control the radius of curvature of the distal section 1440. The other two pull cables 1110c and 1110d are used to control bending of the tip assembly 140 in a plane that is perpendicular to the longitudinal axis (L) of the shaft 110 (See FIG. 14). As shown in FIGS. 15, 16, and 17, the pull cables 1110c and 1110d terminate proximally of the intermediate section 1480. In one embodiment, each of the pull cables 1110c and 1110d terminates in a ball 1530 which may be made from any suitable material, and which is larger in diameter than the lumens 1128c and 1128d in which the pull cables are housed. For example, each of the pull cables 1110c and 1110d may be passed through a hole in the ball (not shown) and the end tied to prevent the cable from coming loose. Other methods of terminating the cables 1110c and 1110d are described in the aforementioned patents, for example, by tying the ends of the cables 1110c and 1110d together at a distal end of proximal section 1420.

It should be appreciated that an additional pair of pull cables may also be provided to control bending of the tip assembly 140 in a plane that is perpendicular to the longitudinal axis of the shaft 110 and perpendicular to the other plane of motion provided by pull cables 1110c and 1110d. Thus, depending upon the number of pull cables and the number of actuators disposed on the handle 120, the radius of curvature of the distal end of the tip assembly 140 may be increased or decreased, and the orientation of the tip assembly 140 may be changed in two different directions in each of two orthogonal planes (e.g., a Y plane and a Z plane) that are perpendicular to the longitudinal axis of the shaft.

The proximal section 1420 includes a central lumen 1125 for passing all of the electrode wires 1510 to the intermediate 1480 and distal 1440 sections, and for passing two of the pull cables 1110a and 1110b. The proximal section 1440 also includes two proximal cable lumens 1128c and 1128d which pass pull cables 1110c and 1110d from the lumen 1525 in the shaft 110 through the length of the proximal section 1420. Proximal cable lumens 1128c and 1128d may contain respective stiffening wires 1710 (FIG. 17) to reduce axial twisting of proximal section 1420. The proximal section 1420 includes a reduced diameter proximal end so that the proximal section 144 may be mated to the distal end of the shaft, within the distal end of the shaft 110.

The intermediate section 1480 is thermally bonded to the distal end of the proximal section 1420 and the proximal end of the distal section 1440. The intermediate section 1480 includes two reduced diameter ends so that it may snugly nest inside the proximal and distal sections. The intermediate section 1480 includes two cable lumens 1128*a* and 1128*b* and a central lumen 1125. Additional lumens may also be included, as described further below. Pull cables 1110*a* and 1110*b* from the central proximal section lumen 1125 are routed to the outwardly disposed cable lumens 1128*a* and 1128*b*, respectively, at a point just past the distal end of the central lumen 1125 of the proximal section 1420. A small transition space is provided between the lumens of the intermediate and proximal sections to permit the pull cables 1110*a*, 1110*b* to be radially displaced.

The distal section 1440 is thermally bonded to the distal end of the intermediate section 1480 and has approximately the same outer diameter as the intermediate section 1480. The distal end of the intermediate section 1480 is recessed within the distal section 1440 to provide a smooth transition between the two sections. The distal section 1440 also includes two cable lumens 1128*a* and 1128*b* and a central lumen 1125. The distal section 1440 may also include additional lumens (shown in FIG. 16), that may be used, for example, to house a control wire for a sliding electrode, to house an irrigation line, to house a wire for a localization sensor, etc. The ends of the pull cables 1110*a* and 1110*b* emanating from the outwardly disposed cable lumens 1128*a* and 1128*b*, respectively, may be tied together and/or potted with an epoxy. The electrode wires 1510 from the central lumen 1125 are fed through radial apertures in the core 1120 and soldered or welded (or bonded with a conductive epoxy) onto an undersurface of the ring electrodes 146, as illustrated in FIGS. 15A and 16. The wire for the distal end or cap electrode may be fed through the central lumen 1125 and soldered, welded, or epoxied onto the cap electrode 147.

In the embodiment illustrated in FIG. 15, each of the plurality of ring electrodes 146 are recessed within the outer circumferential surface of the distal section to provide a low profile. However, for certain procedures, such as ablation, it may be preferable to have the outer surface of one or more of the electrodes 1546 protrude above the outer circumferential surface of the distal section, such as illustrated in FIG. 15A, and illustrated in phantom in FIG. 16. It should be appreciated that a variety of different types of electrodes may be used with the tip assembly depicted in FIG. 15, as the present invention is not limited to any particular type, or construction of electrode.

Various configurations can be used to locate and anchor the pull cables within the shaft and the proximal, intermediate and distal sections of the tip assembly. In general, it is preferable to conduct the pull cables as close as possible to the outer circumference of the section controlled by the cables in order to increase the bending moment. For this reason, the controlling cables for both the proximal and distal sections are directed to outer lumens, i.e., lumens 1128*c* and 1128*d* and lumens 1128*a*, 1128*b*. However, prior to reaching the section that is controlled by the cables, the cables are preferably centrally routed, for example in central lumen 1125, so that manipulation of cables controlling movement of more distal sections of the catheter do not affect the orientation of more proximal sections of the catheter. The illustrated construction has been found to be an optimal arrangement from the points of view of manufacturing ease and function. Other arrangements, however, can also be used. For example, the pull cables can be conducted through the proximal, intermediate, and distal sections exclusively through outer lumens. Examples of other arrangements for the pull cables within the tip assembly 140 are described in the aforementioned U.S. Pat. Nos. 5,383,852, 5,462,527, and 5,611,777.

According to one embodiment of the invention, control of the distal end 144 of the tip assembly 140 may be provided using an individual pull cable together with a superelastic material. A superelastic material may be any material that exhibits a "springback effect" such that it will to return to its original position after undergoing a substantial deformation. The superelastic material may be formed of a metal alloy or a compound containing metals and, in one example, may have an elasticity that is approximately ten times greater than that of stainless steel. While it should be appreciated that any superelastic material may be used in accordance with this embodiment, in one example a superelastic wire is used.

One exemplary superelastic material that may be used is a compound comprising nickel and titanium. In particular, a Nitinol material may be used. Nitinol is a family of intermetallic materials that contain a nearly equal mixture of nickel and titanium and exhibit the properties of shape memory and superelasticity. Nitinol may be set in a particular shape, and will return or "spring back" to that shape after deformation. To set the desired undeformed shape of the superelastic wire, the wire may be constrained in the desired shape and an appropriate heat treatment may be applied. For example, the distal end 144 of the tip assembly 140 of the catheter 100 may be placed in a jig, such as the jigs described in connection with FIGS. 5-10, and heated until the shape of the superelastic wire is set. A temperature of 400-500 degrees Celsius over a period of 1-5 minutes may be sufficient to set the shape.

Nitinol exhibits its optimum superelastic behavior at body temperature, and thus is well-suited for use in a catheter inserted into a body. Nitinol is also well-suited for use within a catheter because it is non-ferromagnetic, and thus will not interfere with MRI imaging, and produces a fluoroscopic image comparable to stainless steel.

Figure 38:
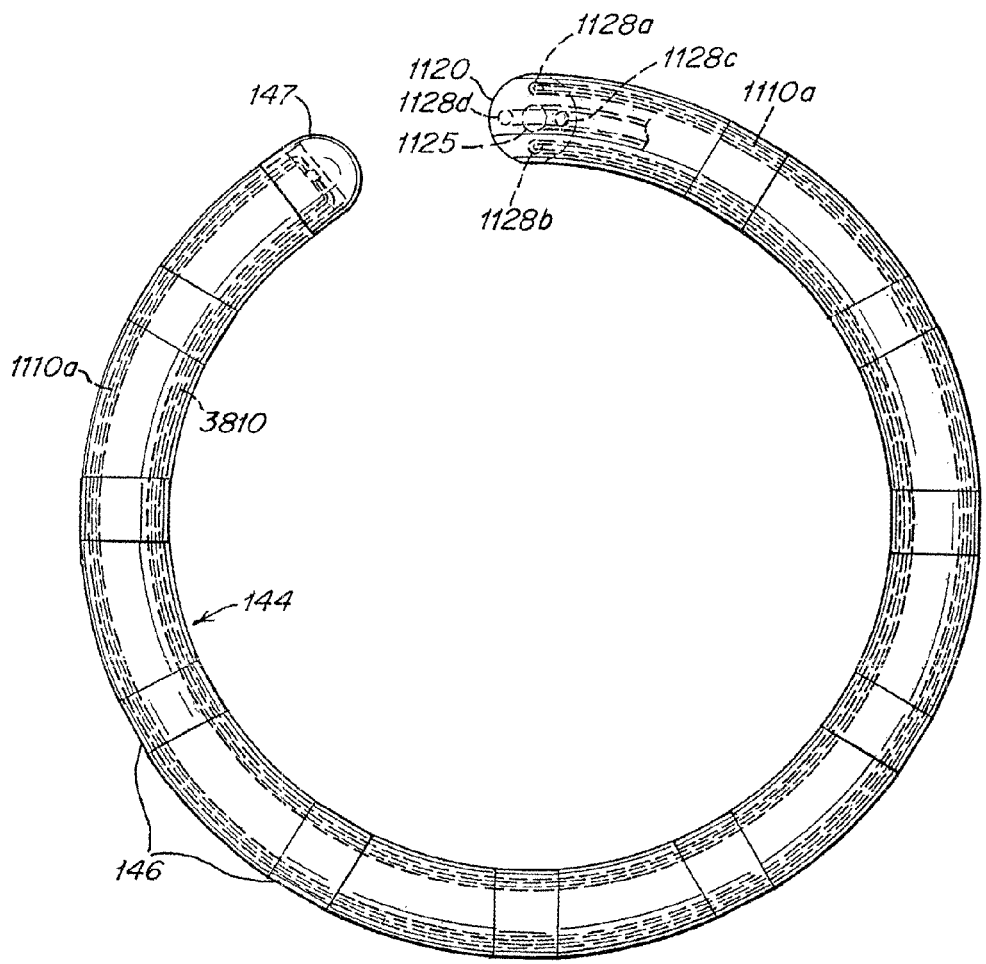
FIG. 38 is an enlarged end elevational view of the distal end tip assembly according to another embodiment of the invention in which a superelastic wire is used to bias the orientation of the tip assembly.

FIG. 38 is an enlarged elevational view of the distal end tip assembly 140 of FIG. 2 implemented in accordance with one embodiment of the invention. As shown in FIG. 38, the distal end 144 of the tip assembly 140 includes a superelastic wire 3810 that may be used with cable 1110*a* to change the radius of curvature of the tip assembly from a first radius to a second radius. As illustrated in FIG. 38, pull cable 1110*a* and superelastic wire 3810 extend along the length of the distal end 144 of the tip assembly 140 through lumens 1128*a* and 1128*b*, respectively, and are tied together and potted with an epoxy adjacent the most distal end of the tip assembly 140.

A number of variations are possible for the distal end 144 of the tip assembly 140 illustrated in FIG. 38. For example, although the superelastic wire 3810 is shown extending along the length of the distal end 144 of the tip assembly 140 through lumen 1128*b*, the superelastic wire 3810 may be disposed in other portions of the catheter 100. For example, the superelastic wire 3810 may be housed within the central lumen 1125 or another lumen, or may be embedded within the core 1120 of the tip assembly 140. Further, although the superelastic wire 3810 is shown anchored at the most distal end of the tip assembly 140 and tied together with the cable 1110*a*, this arrangement is not necessary. Superelastic wire 3810 need not be anchored since, as described above, the wire is formed from a material that exhibits a "springback effect" such that it has a tendency to return to its original position once deformed. It follows that the superelastic wire 3810 also need not be tied to the cable 1110*a*, which may instead be independently anchored at the distal end 144 of the tip assembly 140.

The superelastic wire 3810 may extend through any portion of the catheter 100 sufficient to bias the distal end 144 of the tip assembly 140 in a desired arcuate shape. For example, the wire may originate at the control handle 120 of the catheter 100, or may originate at a more distal location. For example, the superelastic wire 3810 may occupy only that portion of the catheter 100 that may form the arcuate shape (i.e., the distal end 144 of the tip assembly 140). Further, the superelastic wire 3810 may extend through another portion of the catheter 100 to bias the catheter 100 in an additional orientation. The use of superelastic wire 3810 to bias the catheter 100 in different ways at different portions of the catheter will be discussed in more detail below.

Figure 39A:
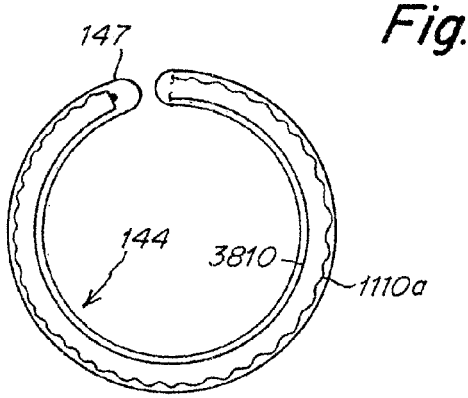
FIGS. 39A and 39B are schematic views illustrating a first configuration for controlling the distal end of the tip assembly with a superelastic wire and a pull wire.
Figure 39B:
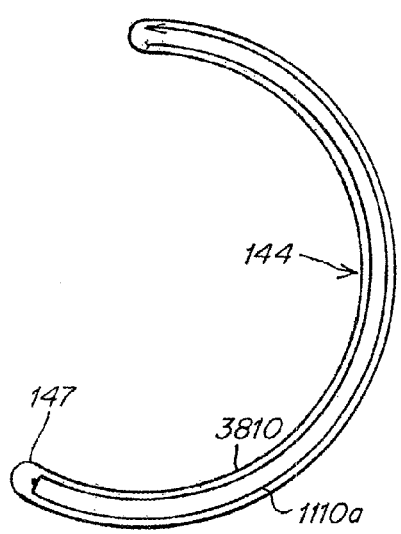

FIGS. 39A and 39B illustrate how the radius of curvature of the distal end 144 of the tip assembly 140 may be changed via manipulation of the cable 1110*a* that is attached to an actuator 122, 124 on the handle 120 (FIG. 1). It should be appreciated that, because only one pull wire is used to change the radius of curvature, only one pull wire is attached to actuator 122 or 124 in accordance with this embodiment. As shown in FIG. 39A, superelastic wire 3810 is biased to form an arcuate curve and causes the distal end 144 of the tip assembly 140 to assume such a shape when no tension is applied to pull cable 1110*a*. When tension is applied to cable 1110*a*, as shown in FIG. 39B, the radius of curvature of the distal end 144 of the tip assembly 140 increases.

If the positions of the pull cable and the superelastic wire are reversed, an opposite effect results. For example, FIGS. 41A and 41B illustrate superelastic wire 3810 disposed on the outer portion of arcuate curve of the distal end 144, thus having a greater radius of curvature than pull wire 1110*b* disposed on the inner portion of the arcuate curve. As shown in FIG. 41A, superelastic wire 3810 is biased to form an arcuate curve and causes the distal end 144 of the tip assembly 140 to assume such a shape when no tension is applied to pull cable 1110*b*. When tension is applied to cable 1110*b*, as shown in FIG. 41B, the radius of curvature of the distal end 144 of the tip assembly 140 decreases.

Figure 43A:
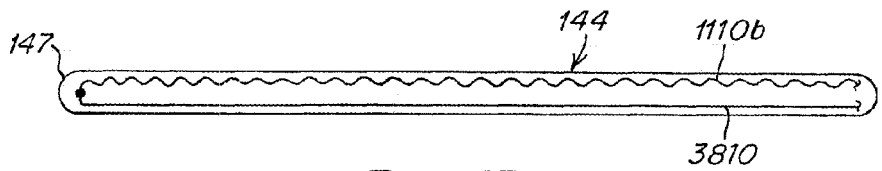
FIGS. 43A and 43B are schematic views illustrating a third configuration for controlling the distal end of the tip assembly with a superelastic wire and a pull wire.
Figure 43B:
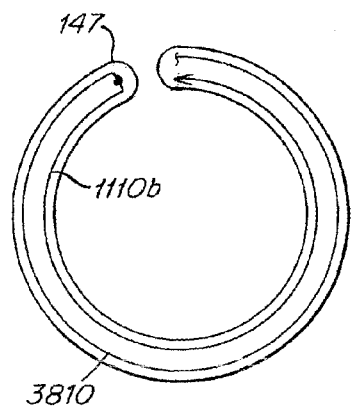

FIGS. 43A and 43B illustrate a configuration similar to that shown in FIGS. 41A and 41B. However, rather than being biased in an arcuate curve, superelastic wire 3810 is biased linearly and causes the distal end 144 of the tip assembly 140 to assume a linear orientation when no tension is applied to pull cable 1110*b* (see FIG. 43A). When tension is applied to cable 1110*b*, as shown in FIG. 43B, the radius of curvature of the distal end 144 of the tip assembly 140 decreases, causing the distal end 144 of the tip assembly 140 to assume an arcuate curve.

According to another embodiment of the invention, adhesive may be introduced into the catheter 100 (FIG. 1) and cured in a configuration such that it imparts a bias on the catheter 100 or tends to retain a portion of the catheter 100 in a particular position or shape. For example, the adhesive may be injected into a lumen of the catheter 100, e.g., by means of a syringe, and a portion of the catheter 100 may be placed in a jig, such as the jigs described in connection with FIGS. 5-10. The jig holds the catheter 100 in a desired position while the adhesive cures so that the catheter 100 with the cured adhesive is biased in a particular orientation. According to another aspect of the invention, the adhesive may be used in connection with a pull cable to provide control of the tip assembly 140 (FIG. 140). Epoxy and silicone are two exemplary adhesives that may be used in accordance with the present embodiment. Other adhesives that are compatible with the catheter material and that impart a bias or that tend to retain their shape when cured may also be used. Various configurations of the catheter 100 including an adhesive to provide a bias will be described below.

Figure 45:
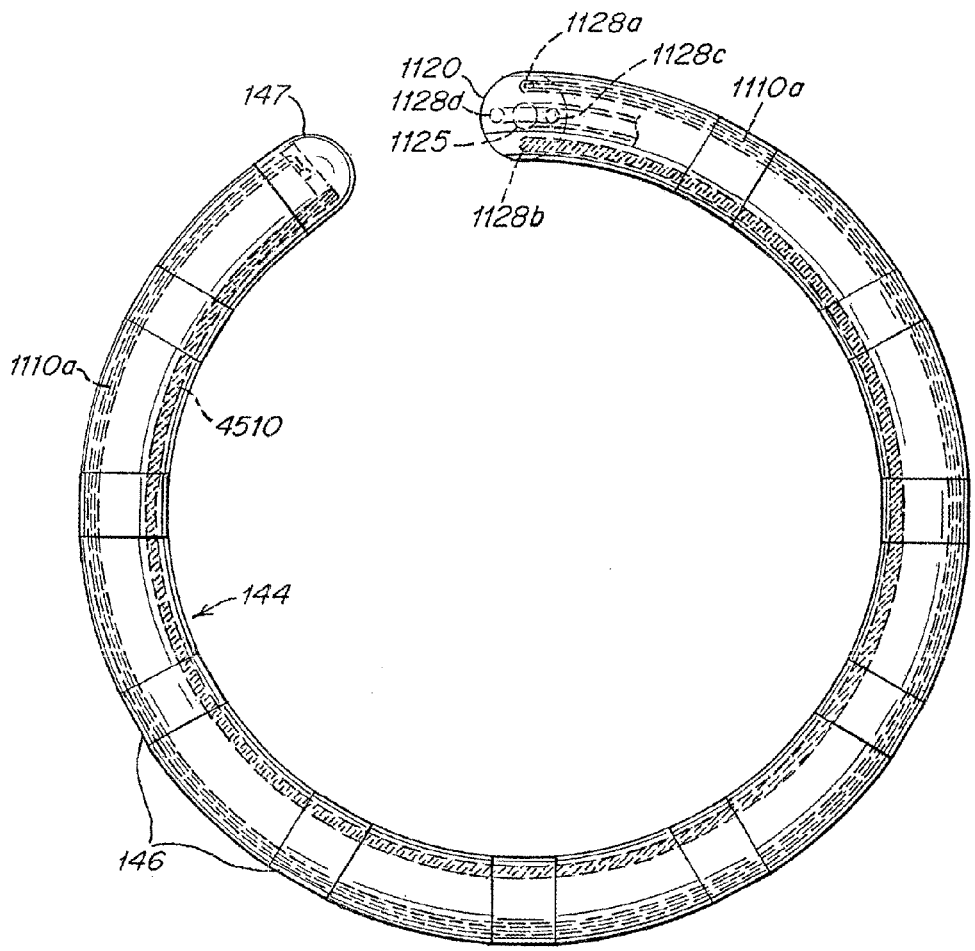
FIG. 45 is an enlarged end elevational view of the distal end tip assembly according to another embodiment of the invention in which an adhesive is used to bias the orientation of the tip assembly.

FIG. 45 is an enlarged elevational view of the distal end tip assembly 140 of FIG. 2 implemented in accordance with the present embodiment of the invention. As shown in FIG. 45, the distal end 144 of the tip assembly 140 includes adhesive 4510 within lumen 1128*b* that has been cured in an arcuate shape. When used with cable 1110*a*, the adhesive 4510 may be used to change the radius of curvature of the tip assembly from a first radius to a second radius, as will be described.

It should be appreciated that while the adhesive 4510 is shown extending along the length of the distal end 144 of the tip assembly 140 through lumen 1128*b*, the adhesive 4510 may be disposed in other portions of the catheter 100. For example, the adhesive 4510 may be disposed within the central lumen 1125 or another lumen of the tip assembly 140. Further, the adhesive 4510 may extend through any portion of the catheter 100 sufficient to bias the distal end 144 of the tip assembly 140 is a desired arcuate shape. For example, the adhesive 4510 may extend from the control handle 120 of the catheter 100, or may originate at a more distal location or may occupy only that portion of the catheter 100 that may form the arcuate shape (i.e., the distal end 144 of the tip assembly 140). In addition, the adhesive 4510 may extend through another portion of the catheter 100 and be cured to bias the catheter 100 in an additional orientation. The use of adhesive 4510 to bias the catheter 100 in different ways at different portions of the catheter will be discussed in more detail below.

Figure 46A:
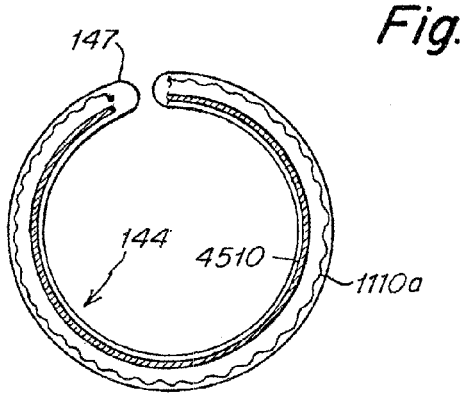
FIGS. 46A and 46B are schematic views illustrating a first configuration for controlling the distal end of the tip assembly with a cured adhesive and a pull wire.
Figure 46B:
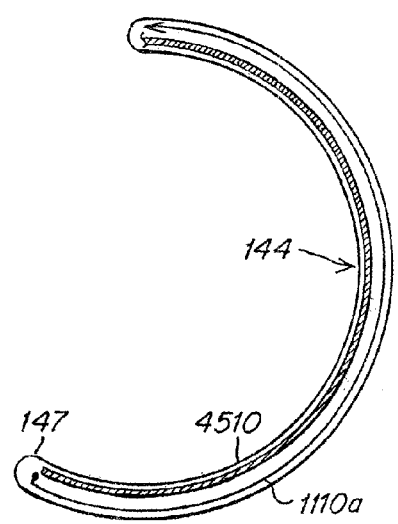

FIGS. 46A and 46B illustrate how the radius of curvature of the distal end 144 of the tip assembly 140 may be changed via manipulation of the cable 1110*a* that is attached to an actuator 122, 124 on the handle 120 (FIG. 1). It should be appreciated that, because only one pull wire is used to change the radius of curvature, only one pull wire is attached to actuator 122 or 124 in accordance with this embodiment. As shown in FIG. 46A, adhesive 4510 is biased to form an arcuate curve and causes the distal end 144 of the tip assembly 140 to assume such a shape when no tension is applied to pull cable 1110*a*. When tension is applied to cable 1110*a*, as shown in FIG. 46B, the radius of curvature of the distal end 144 of the tip assembly 140 increases.

If the positions of the pull wire and the adhesive are reversed, an opposite effect results. For example, FIGS. 48A and 48B illustrate adhesive 4510 disposed on the outer portion of arcuate curve of the distal end 144, thus having a greater radius of curvature than pull wire 1110*b* disposed on the inner portion of the arcuate curve. As shown in FIG. 48A, adhesive 4510 is biased to form an arcuate curve and causes the distal end 144 of the tip assembly 140 to assume such a shape when no tension is applied to pull cable 1110*b*. When tension is applied to cable 1110*b*, as shown in FIG. 48B, the radius of curvature of the distal end 144 of the tip assembly 140 decreases.

Figure 50A:
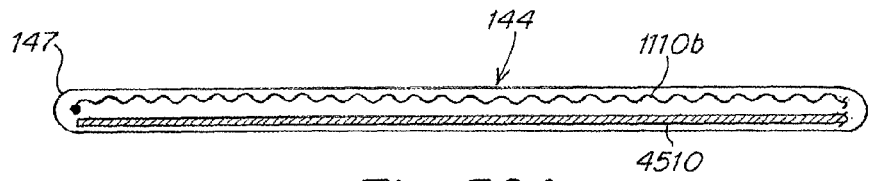
FIGS. 50A and 50B are schematic views illustrating a third configuration for controlling the distal end of the tip assembly with a cured adhesive and a pull wire.
Figure 50B:
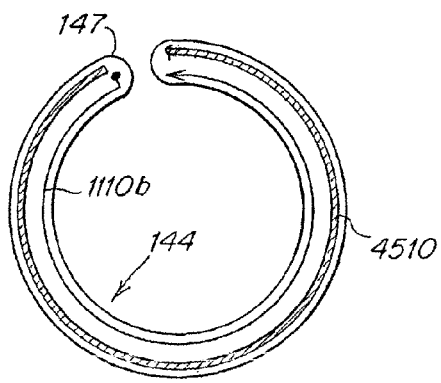

FIGS. 50A and 50B illustrate a configuration similar to that shown in FIGS. 48A and 48B. However, rather than being biased in an arcuate curve, adhesive 4510 is biased linearly and causes the distal end 144 of the tip assembly 140 to assume a linear orientation when no tension is applied to pull cable 1110*b* (see FIG. 50A). When tension is applied to cable 1110*b*, as shown in FIG. 50B, the radius of curvature of the distal end 144 of the tip assembly 140 decreases, causing the distal end 144 of the tip assembly 140 to assume an arcuate curve.

Figure 52:
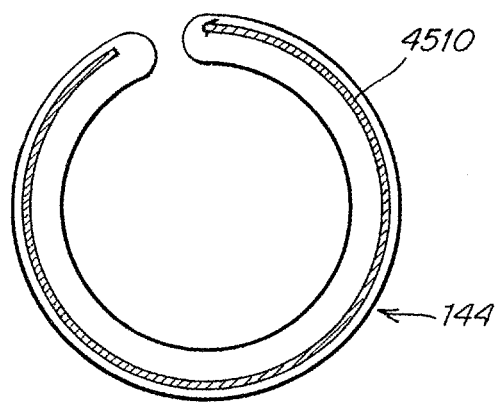
FIG. 52 is a schematic view illustrating the distal end of the tip assembly according to another embodiment of the invention in which an adhesive is used to impart a fixed bias to the orientation of the tip assembly.
Figure 53:
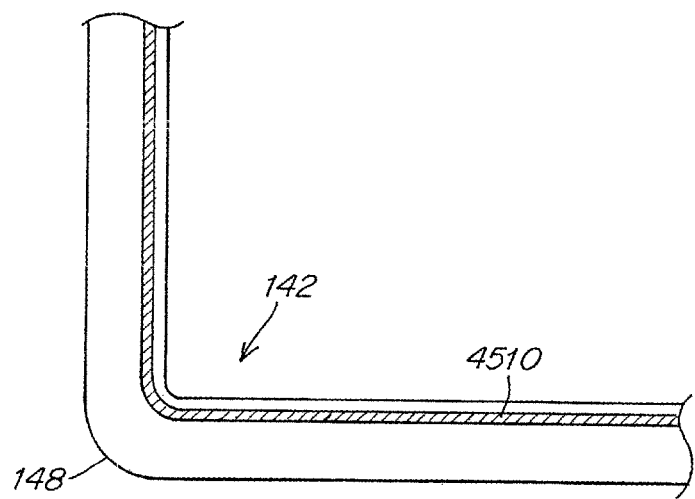
FIG. 53 is a schematic view illustrating the proximal end of the tip assembly according to the embodiment of FIG. 52.

FIGS. 52 and 53 illustrate an alternative embodiment of the invention in which the pull wire described above is omitted.

Thus, the adhesive is used to bias a portion of the catheter 100 in a fixed configuration. As shown in FIG. 52, adhesive 4510 may be included in the distal end 144 of the tip assembly 140 and cured to bias the distal end 144 in an arcuate shape. As shown in FIG. 53, the adhesive may additionally or alternatively be included in the proximal end 142 of the tip assembly 140 and cured to bias the proximal end 142 with an approximately ninety degree bend 148. As discussed above, the adhesive 4510 in FIGS. 52 and 53 may be introduced into a desired lumen of the catheter 100, e.g., via a syringe, and cured in a jig, such as those of FIGS. 5-10, to effect the bias on the catheter 100. We have found that providing an adhesive in the tip assembly 140 as illustrated in FIGS. 52 and 53 tends to prevent the curve from relaxing during storage or in use.

Figure 65A:
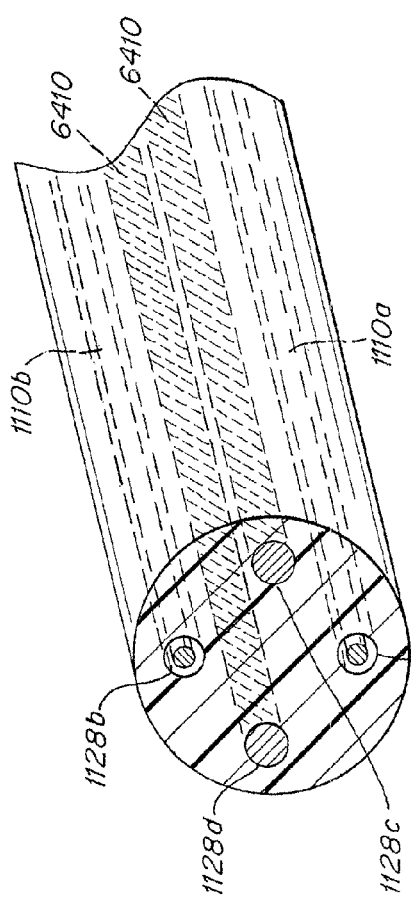
FIG. 65A is a fragmentary elecational view illustrating the distal end of the tip assembly according to another embodiment of the invention in which an adhesive is used to provide support to the tip assembly.
Figure 65B:
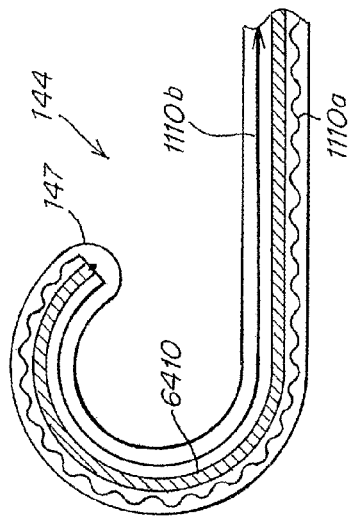
FIG. 65B is a schematic view illustrating control of the distal end of the tip assembly according to the embodiment of FIG. 65A.

FIGS. 65A and 65B illustrate another embodiment of the invention in which adhesive is used within the catheter to provide support to the arcuate curve of the distal end 144 of the tip assembly 140. To provide such support, adhesive is introduced into the catheter and cured while the catheter is retained in a particular position or shape.

The adhesive may be injected into one or more lumens of the catheter, e.g., by means of a syringe, and a portion of the catheter may be placed in a jig, such as the jigs described in connection with FIGS. 5-10. The jig holds the catheter in a desired position while the adhesive cures. As shown in FIGS. 65A and 65B, adhesive 6410 is disposed within lumens 1128*c-d*, which may also contain electrode wires or other wires. Although the adhesive 6410 is shown disposed within lumens 1128*c-d*, the adhesive 6410 may alternatively be disposed in a central lumen or another lumen not occupied by pull cables. The adhesive 6410 may be epoxy, silicone, or other material that tends to retain a catheter in a particular shape when the material in the catheter is cured while the catheter is in a particular position.

As shown in FIG. 65B, pull cables 1110*a-b* may be used to control the position of the proximal end 144 of the tip assembly 140. In the figure, tension is applied to the pull cable 1110*b* and not applied to the pull cable 1110*a*, such that an arcuate curve having a particular radius of curvature formed. The adhesive 6410, which may be cured in a curved configuration, provides support to the catheter structure such that the pull cables are able to effect the desired radius of curvature. Without the adhesive 6410, the ability of the pull cables 1110*a-b* to effect a desired radius of curvature may degrade over time.

Active Bend

As noted above, the approximately ninety degree bend in the distal end tip assembly 140 may be either fixed (e.g., permanently formed with the use of a jig, such as jigs 500, 700, and 900, described in detail with respect to FIGS. 5-10 below), or active (e.g., movable between approximately zero and approximately ninety degrees relative to the longitudinal axis of the shaft 110 of the catheter 100) through the use of an actuator 122, 124 disposed on the handle 120. FIGS. 21 and 21A illustrate an embodiment that includes such an "active bend."

As shown in FIG. 21, in one embodiment, the distal end tip assembly 140 includes a proximal section 2120, an intermediate section 2180 that may be actively bent via manipulation of a control cable (FIG. 21A) attached to an actuator (e.g., actuator 122) on the control handle 120 to be approximately perpendicular to the longitudinal axis of the shaft 110, and a distal section 2140 having a radius of curvature that can be adjusted via manipulation of a control cable attached to an actuator (e.g., actuator 124) on the handle 120. The distal section 2140 includes one or more electrodes 146, 147 disposed along a length of the distal section 2140.

As shown in FIG. 21A, which is a cross section of the proximal section 2120 of the tip assembly 140 taken along line 21A-21A in FIG. 21, the cables 1110*c* and 1110*d* that control bending of the intermediate section 2180 may be formed from a single cable that is wrapped around a reduced diameter end of the proximal section 2120 and that is recessed within the intermediate section 2128 in a manner similar to that described with respect to FIG. 12 in U.S. Pat. No. 5,383,852. In general, the cable will be wrapped about that portion of the tip assembly that is immediately prior to the point at which bending is to occur. In this embodiment, tension applied to cable 1110*c* results a bending of the distal section 2140 of the tip assembly 140 in a downward direction (as seen in FIG. 21) to orient the arcuately curved distal section 2140 in a plane that is perpendicular to the longitudinal axis of the shaft 110, and tension applied to cable 1110*d* results in the bending of the distal section 2140 of the tip assembly 140 in an upward direction (as seen in FIG. 21) to return to its position along the longitudinal axis of the shaft. Because the handle 120 may be rotated one hundred and eighty degrees, the ability to bend the distal section in an opposite direction is unnecessary, but may be provided, if desired. It should be appreciated that in other embodiments, only a single control wire may be used.

To accommodate such an active curve, the material from which the intermediate section 2180 is formed should be less stiff than the material from which the shaft 110 is formed so that bending occurs in the intermediate section 2180. Preferably, the material from which the distal section is formed is less stiff than that from which the intermediate section is formed to permit the radius of curvature of the distal section 2140 to be changed without altering the orientation of the intermediate and proximal sections 2180 and 2120, respectively.

To facilitate bending in a known and controlled manner, the intermediate section 2180 may be permanently biased to have a bend of a few degrees relative to the longitudinal axis (L) of the shaft 110. Because the intermediate section 2180 is permanently biased a few degrees away from the longitudinal axis (L) of the shaft 110, tension applied to cable 1110*c*, for example, results in bending of the intermediate section 2180 in the plane of the bend toward a ninety degree angle with the longitudinal axis (L) of the shaft 110. Tension applied to the opposing cable, for example 1110*d*, results in bending of the intermediate section 2180 in the plane of the bend back toward the longitudinal axis (L) of the shaft 110. Because the intermediate section 2180 is biased a few degrees away from the longitudinal axis (L) of the shaft 110 in a particular direction, any bending of the intermediate section 2180 occurs in the plane aligned in the same direction as that bend in a known and controlled manner. Were the intermediate section 2180 not biased in a particular direction, bending could occur in any direction.

Figure 40A:
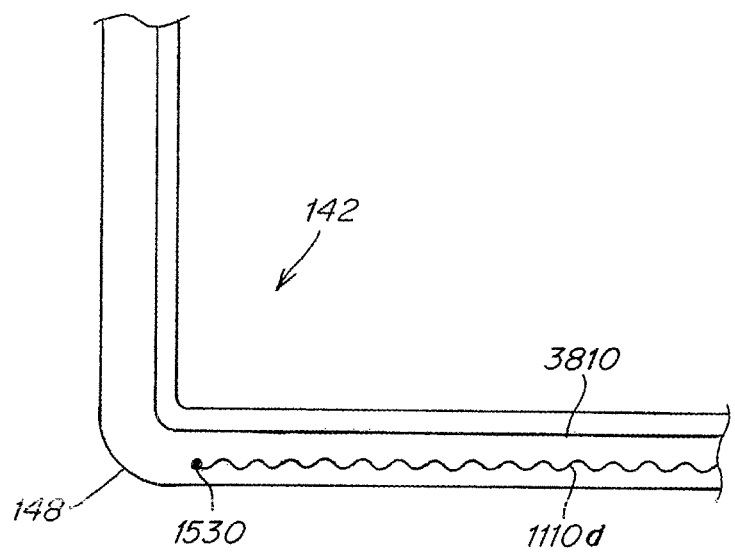
FIGS. 40A and 40B are schematic views illustrating a first configuration for controlling the proximal end of the tip assembly with a superelastic wire and a pull wire.
Figure 40B:
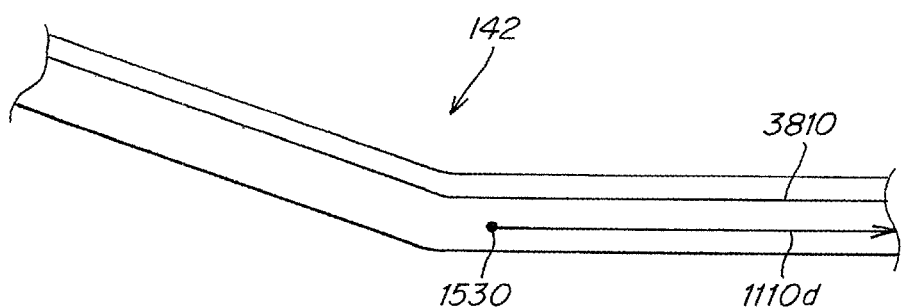

Other manners of biasing the tip assembly 142 are also possible. In one embodiment, the principles applied in FIGS. 39, 41, and 43 to effect control of the arcuate curve of the distal end 144 of the tip assembly 140 using a superelastic wire 3810 may be applied to effect control of the ninety degree bend 148 of the proximal end 142 of the tip assembly 140. FIGS. 40A and 40B illustrate how the bend angle of the proximal end 142 of the tip assembly 140 may be changed via manipulation of a cable 1110*d* that may be attached to an actuator 122, 124 on the handle 120 (FIG. 1). As shown in FIG. 40A, superelastic wire 3810 is biased to form a bend having an angle of approximately ninety degrees (in one embodiment) with respect to the longitudinal axis of the catheter 100 and causes the proximal end 142 of the tip assembly 140 to assume such a shape when no tension is applied to pull cable 1110d. When tension is applied to cable 1110d, as shown in FIG. 40B, the bend angle of the proximal end 142 of the tip assembly 140 decreases.

If the positions of the pull wire and the superelastic wire are reversed, the bend angle of the proximal end 142 of the tip assembly 140 may be increased from the bias position of the superelastic wire. For example, FIGS. 42A and 42B illustrate superelastic wire 3810 disposed on the outer portion of the proximal end 142 with respect to the bend, and a pull cable 1110c disposed on the inner portion. As shown in FIG. 41A, superelastic wire 3810 is biased to form an acute bend angle and causes the distal end 144 of the tip assembly 140 to assume such a shape when no tension is applied to pull cable 1110c. When tension is applied to cable 1110c, as shown in FIG. 42B, the angle of the bend of proximal end 142 increases to approximately ninety degrees (in one embodiment).

Figure 44A:
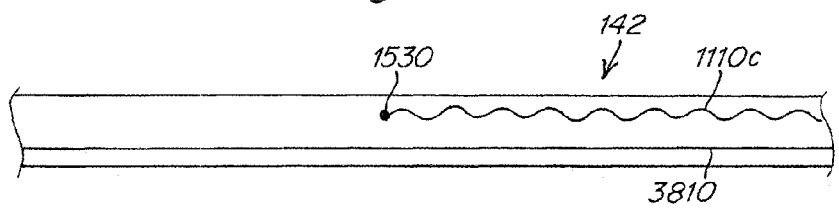
FIGS. 44A and 44B are schematic views illustrating a third configuration for controlling the proximal end of the tip assembly with a superelastic wire and a pull wire.
Figure 44B:
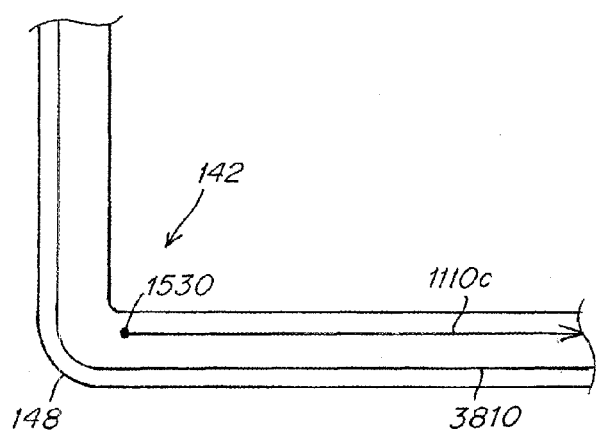

FIGS. 44A and 44B illustrate a configuration similar to that shown in FIGS. 42A and 42B. However, rather than being biased to form a bend angle, superelastic wire 3810 is biased linearly and causes the proximal end 142 of the tip assembly 140 to assume a linear orientation when no tension is applied to pull cable 1110c (see FIG. 44A). When tension is applied to cable 1110c, as shown in FIG. 44B, the angle of the bend of proximal end 142 increases to approximately ninety degrees in one embodiment. It should be appreciated that although the bend is described as increasing to approximately ninety degrees, other bend angles are also possible.

Figure 47A:
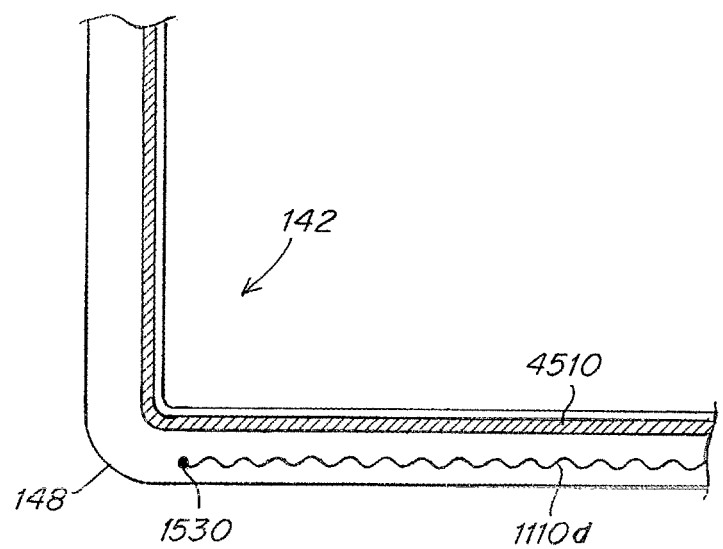
FIGS. 47A and 47B are schematic views illustrating a first configuration for controlling the proximal end of the tip assembly with a cured adhesive and a pull wire.
Figure 47B:
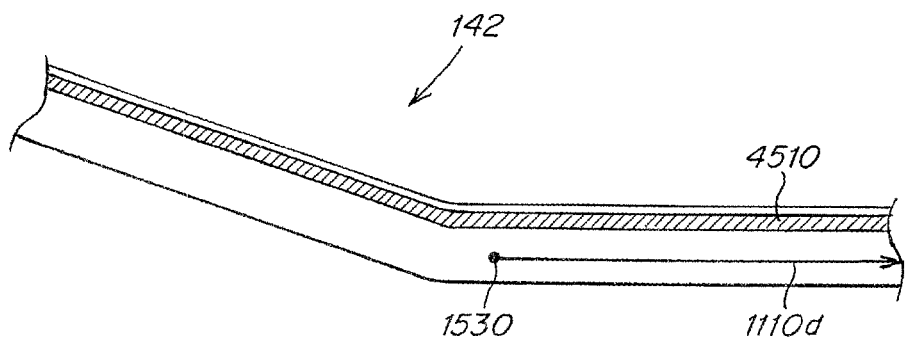

The principles applied in FIGS. 46, 48, and 50 to effect control of the arcuate curve of the distal end 144 of the tip assembly 140 using adhesive 4510 may also be applied to effect control of the ninety degree bend 148 of the proximal end 142 of the tip assembly 140. FIGS. 47A and 47B illustrate how the bend angle of the proximal end 142 of the tip assembly 140 may be changed via manipulation of a cable 1110d that may be attached to an actuator 122, 124 on the handle 120 (FIG. 1). As shown in FIG. 47A, adhesive 4510 is biased to form a bend having an angle of approximately ninety degrees with respect to the longitudinal axis of the catheter 100 and causes the proximal end 142 of the tip assembly 140 to assume such a shape when no tension is applied to pull cable 1110d. When tension is applied to cable 1110d, as shown in FIG. 47B, the bend angle of the proximal end 142 of the tip assembly 140 decreases.

If the positions of the pull wire and the adhesive are reversed, the bend angle of the proximal end 142 of the tip assembly 140 may be increased from the bias position of the adhesive. For example, FIGS. 49A and 49B illustrate adhesive 4510 disposed on the outer portion of the proximal end 142 with respect to the bend, and a pull cable 1110c disposed on the inner portion. As shown in FIG. 49A, adhesive 4510 is biased to form an acute bend angle and causes the distal end 144 of the tip assembly 140 to assume such a shape when no tension is applied to pull cable 1110c. When tension is applied to cable 1110c, as shown in FIG. 49B, the angle of the bend of proximal end 142 increases to approximately ninety degrees.

Figure 51A:
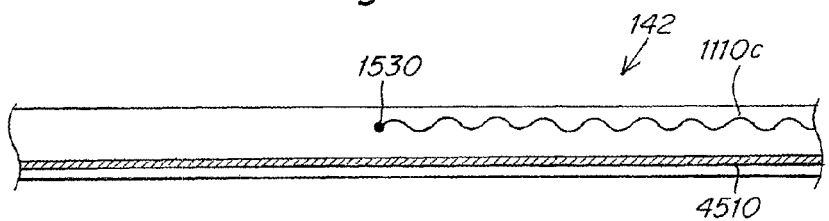
FIGS. 51A and 51B are schematic views illustrating a third configuration for controlling the proximal end of the tip assembly with a cured adhesive and a pull wire.
Figure 51B:
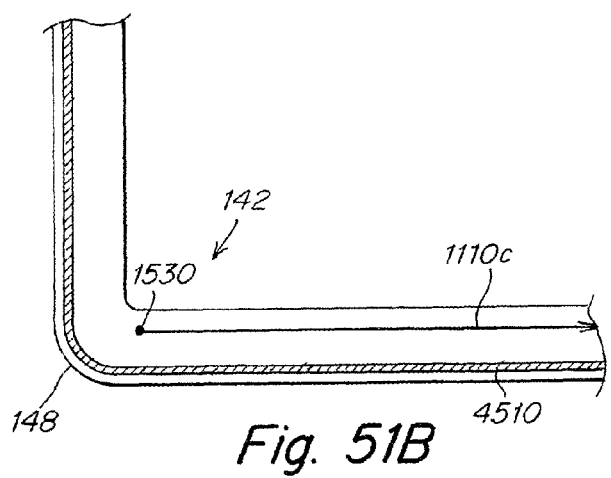

FIGS. 51A and 51B illustrate a configuration similar to that shown in FIGS. 49A and 49B. However, rather than being biased to form a bend angle, adhesive 4510 is biased linearly and causes the proximal end 142 of the tip assembly 140 to assume a linear orientation when no tension is applied to pull cable 1110c (see FIG. 51A). When tension is applied to cable 1110c, as shown in FIG. 51B, the angle of the bend of proximal end 142 increases to approximately ninety degrees.

Figure 64A:
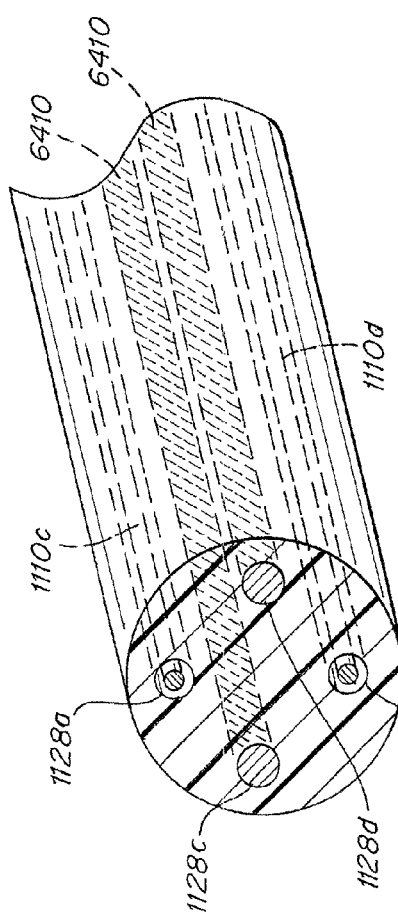
FIG. 64A is a fragmentary elevational view illustrating the proximal end of the tip assembly according to another embodiment of the invention in which an adhesive is used to provide support to the tip assembly.
Figure 64B:
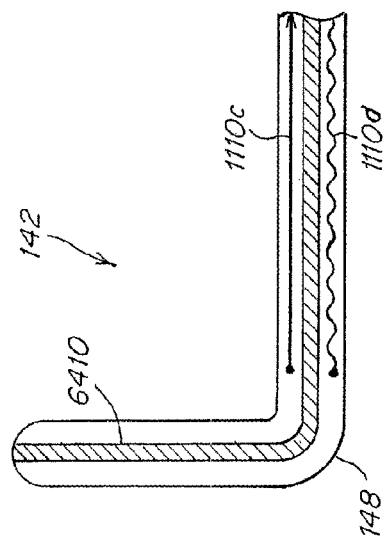
FIG. 64B is a schematic view illustrating control of the proximal end of the tip assembly according to the embodiment of FIG. 64A.

FIGS. 64A and 64B illustrate another embodiment of the invention in which adhesive is used within the catheter to provide support to the ninety degree bend 148 of the proximal end 142 of the tip assembly 140. To provide such support, adhesive is introduced into the catheter and cured while the catheter is retained in a particular position or shape. The adhesive may be injected into one or more lumens of the catheter, e.g., by means of a syringe, and a portion of the catheter may be placed in a jig, such as the jigs described in connection with FIGS. 5-10. The jig holds the catheter in a desired position while the adhesive cures. As shown in FIGS. 64A and 64B, adhesive 6410 is disposed within lumens 1128c-d, which may also contain electrode wires or other wires. Although the adhesive 6410 is shown disposed within lumens 1128c-d, the adhesive 6410 may alternatively be disposed in a central lumen or another lumen not occupied by pull cables. The adhesive 6410 may be epoxy, silicone, or other material that tends to retain a catheter in a particular shape when the material in the catheter is cured while the catheter is in a particular position.

As shown in FIG. 64B, pull cables 1110c-d may be used to control the position of the proximal end 142 of the tip assembly 140. In the figure, tension is applied to the pull cable 1110c and not applied to the pull cable 1110d, such that a bend having an angle of approximately ninety degrees 148 is formed. The adhesive 6410, which may be cured in a bent configuration, provides support to the catheter structure such that the pull cables are able to effect a desired bend angle. Without the adhesive 6410, the ability of the pull cables 1110c-d to effect a desired bend angle may degrade over time.

Superelastic Channels

FIGS. 66-72 illustrate a further embodiment of the invention according to which a superelastic channel may be used to impart a bias to a portion of the catheter having a particular configuration, such that the portion will "spring back" to the configuration after being deformed. In one example, a superelastic channel may be incorporated within a portion of a lumen of the catheter to bias the catheter in a particular configuration while allowing a catheter component (e.g., a pull cable, wire, or fluid conduit), or multiple such catheter components, to pass through the portion of the lumen. In another example, a superelastic channel may be incorporated within the catheter, but not within a lumen. For instance, the channel may form part of the exterior sheath of the catheter, or may be an interior channel that at least partially encloses many structures (e.g., lumens) in the catheter.

Figure 66:
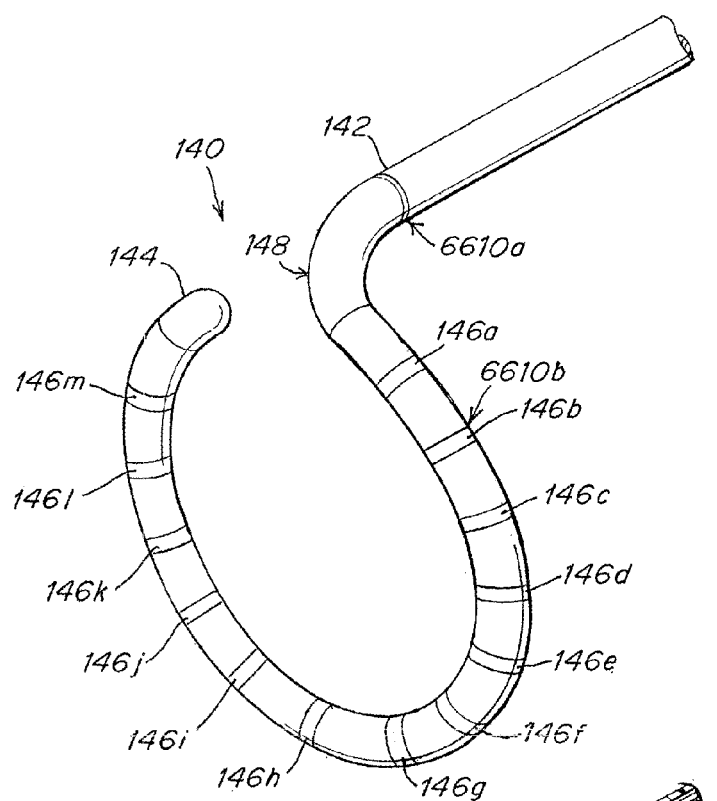
FIG. 66 is a perspective view of a distal tip assembly illustrating an exemplary location where superelastic channels may be located in the distal tip assembly.
Figure 67:
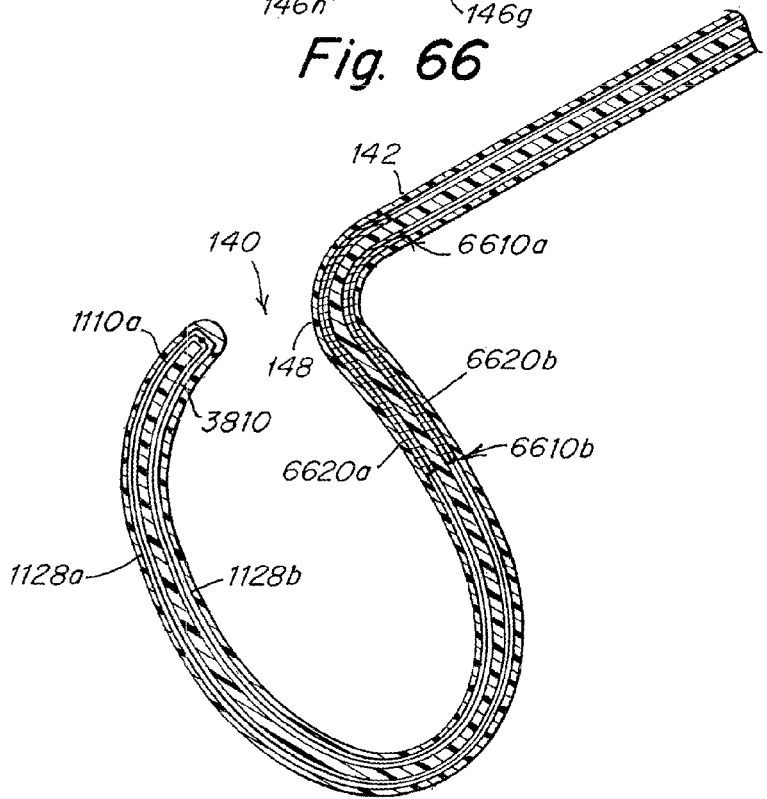
FIG. 67 illustrates a cross sectional view of the distal tip assembly shown in FIG. 66.

In one example, illustrated in FIGS. 66-67, superelastic channels 6620a-b are included in the portion of the tip assembly 140 that includes bend 148, which is described herein as being an approximately ninety degree bend, but which may have an angle that is greater or less than ninety degrees. The channels 6620a-b are included within lumens 1128a and 1128b, respectively, and extend from a location 6610a at the proximal end 142 of the tip assembly 140 to a location 6610b at electrode 146b. Thus, in one example, channels 6620a-b extend from the proximal end 142 of the tip assembly 140 to a portion of the distal end 144 of the tip assembly 140, which may be biased to form a curve. The channels 6620a-b may be held in place by the lumens 1128a-b themselves, or may be adhered to the lumens, e.g., with "epoxy between each channel and lumen near location 6610a. The channels 6620a-b bias the portion of the catheter spanning locations 6610a and 6610b to form the configuration of ninety degree bend 148 and to "spring back" to the configuration after being deformed. Thus, channels 6620a-b form a resilient bend angle in tip assembly 140. It should be appreciated, however, that channels 6620a-b may be used in connection with other biasing mechanisms (e.g., heating in a jig) and/or resiliency mechanisms (e.g., superelastic wires) to achieve the desired bias or resiliency.

Many variations on the configuration shown in FIGS. 66-67 are possible to achieve a resilient bend angle in tip assembly 140 using superelastic channels. For example, channels 6620a-b may occupy any of the lumens 1128a-d described herein, or one or more additional lumens. Further, although two channels are illustrated, a single channel or greater than two channels (e.g., three, four, five, or more) may alternatively be employed. In addition, while channels 6620 are disposed between locations 6610a and 6610b in FIGS. 66-67, this configuration is merely exemplary, and channels 6620 may span a portion of the catheter of a different size or location. Optionally, the portion of the catheter at bend 148 may be formed of a material having a lower durometer than adjacent portions of the catheter. Making the region at bend 148 softer enhances the effect of the superelastic channel by allowing a greater degree of responsiveness to the bias imparted by the superelastic channel.

Figure 68:
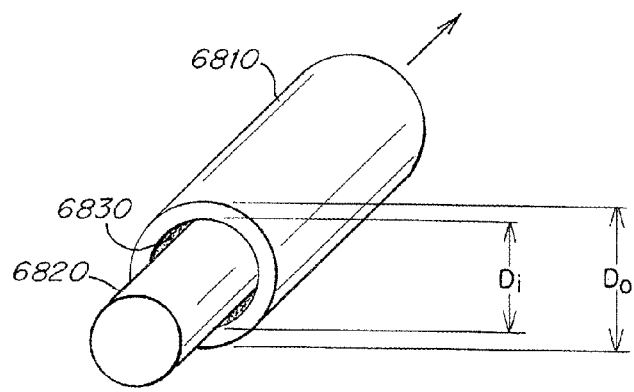
FIG. 68 is a perspective view of a portion of one exemplary implementation of a superelastic channel.
Figure 69:
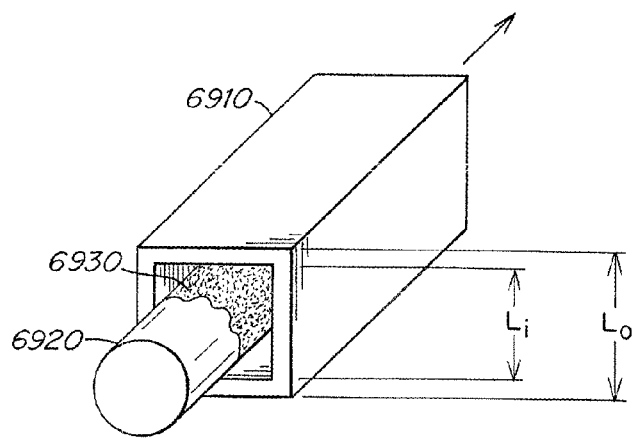
FIG. 69 is a perspective view of a portion of another exemplary implementation of a superelastic channel.

FIGS. 68-69 illustrate exemplary configurations for the superelastic channels described above. FIG. 68 illustrates a superelastic channel 6810 having a cylindrical shape with an inner surface diameter Di and an outer surface diameter Do. FIG. 69 illustrates a superelastic channel 6910 having a rectangular shape with an length Li between opposite inner surfaces and a length Lo between opposite outer surfaces. In one example, inner surface diameter Di or length Li may be approximately 0.01-0.011 inch, and outer surface diameter Do or length Lo may be approximately 0.014-0.015 inch. It should be appreciated that the superelastic channels described herein may assume a variety of shapes and are not limited to those shown in FIGS. 68-69. For example, the channels may be shaped as a spring, an oval-shaped tube, a multi-sided tube (e.g., a pentagonal or octagonal tube), or another hollow shape. Superelastic channels 6810 and 6910 may be formed of any of the exemplary superelastic materials described herein, such as Nitinol or another compound comprising nickel and titanium. In one example, superelastic channels 6810 and 6910 are formed of string-tempered stainless steel.

Pull cables 6820 or 6920 are shown disposed within superelastic channels 6810 and 6910, respectively. To facilitate movement of the pull cables within their respective channels, the pull cables and/or channels may include low-friction material, such as teflon. For example, FIG. 68 illustrates a low-friction coating 6830 adhered to the interior of superelastic channel 6810 to facilitate movement of pull cable 6820. Alternatively, channel 6810 itself may be formed of a low-friction material. FIG. 69 illustrates a low-friction coating 6930 adhered to the exterior of pull cable 6920 to facilitate movement of pull cable 6920. The coating 6930 may be included on the entirety of the pull cable 6920, or on the portion of the pull cable that contacts channel 6910 only. Alternatively, pull cable 6920 may itself may be formed of a low-friction material, either wholly or in-part.

It should be appreciated that although pull cables are shown passing through the superelastic channels illustrated in FIGS. 68-69, the invention is not limited in this respect. As discussed previously, other catheter components, such as wires or fluid conduits, may pass through the superelastic channel. Alternatively, the channel may be much larger, and may form part of the exterior sheath of the catheter, or may be an interior channel that encloses many structures (e.g., lumens) in the catheter.

Figure 70:
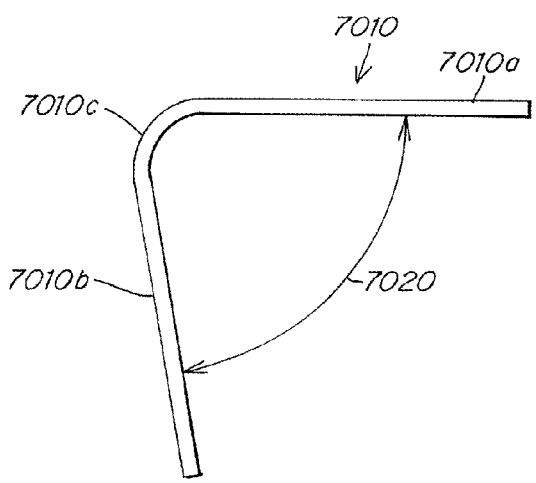
FIG. 70 is an elevational view of a superelastic channel.

FIG. 70 illustrates an exemplary shape of a superelastic channel before the channel is incorporated into the body of a catheter. Superelastic channel 7010 includes a proximal leg 7010a, a distal leg 7010b, and a bend 7010c that joins the proximal and distal legs. In one example, the bend 7010c has a radius of approximately 0.25 inch, and legs 7010a-b form an angle 7020 between 60° and 110° (e.g., approximately 80°), although other dimensions are possible. Further, while channel 7010 is illustrated as being substantially planar, distal leg 7010b may have a curvature. In one example, such curvature corresponds to the curvature of a portion of the distal end 144 of the tip assembly 140. To set the desired undeformed shape of the superelastic channel, the channel may be constrained in the desired shape and an appropriate heat treatment may be applied in a manner similar to that described in connection with the superelastic cables discussed herein.

Figure 71:
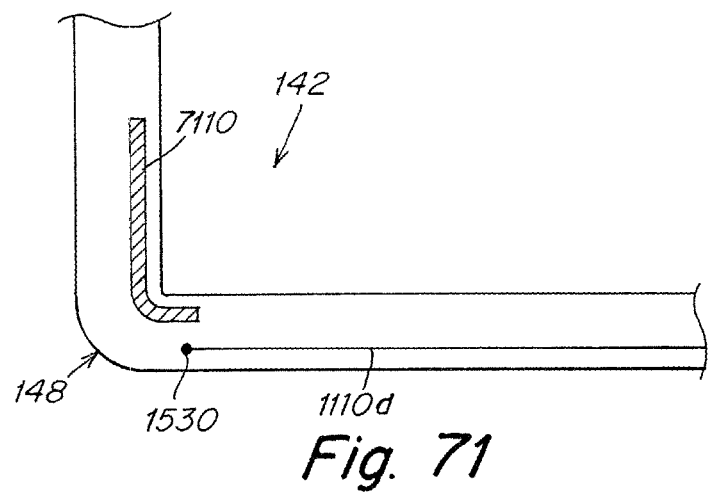
FIG. 71 is a schematic view illustrating a configuration for controlling the proximal end of a tip assembly having a superelastic channel using a pull wire.

While the description of FIGS. 66-70 contemplates the use of superelastic channels to form a "fixed bend" in the tip assembly 140, superelastic channels may also be used in connection with an active bend (i.e., a bend controlled via manipulation of an actuator). FIG. 71 illustrates a superelastic channel 7110 included in the proximal end 142 of the tip assembly 140 to form a resilient curve at bend 148, wherein a pull cable 1110d is further included to allow controlled manipulation of the bend 148. The configuration of FIG. 71 is similar to that described in connection with FIGS. 40A-B, except that a superelastic channel is used rather than a superelastic wire. Further, the superelastic channel 7110 illustrated occupies only a portion of the tip assembly 140, although alternatively the superelastic channel may extend further into or to the end of the tip assembly 140. Manipulation of the bend 148 of FIG. 71 via pull cable 1110d may occur in the same manner as described in connection with FIGS. 40A-B.

Figure 72:
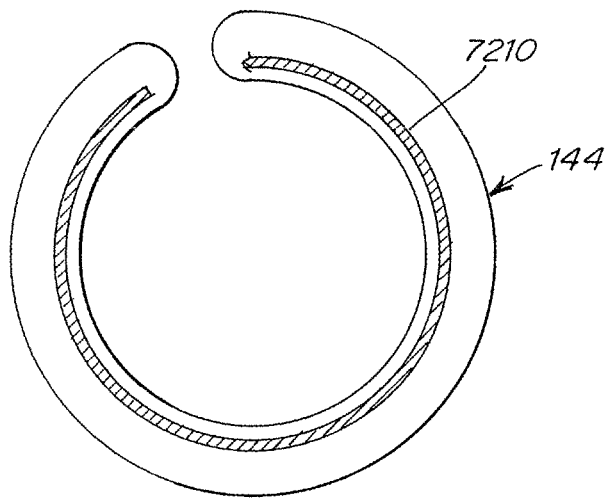
FIG. 72 is a schematic view illustrating the distal end of the tip assembly according to another embodiment of the invention in which a superelastic channel is used to impart a bias to the orientation of the tip assembly.

Although the superelastic channels described above are used to form a resilient curve at ninety degree bend 148, it should be appreciated that the invention is not limited in this respect. Superelastic channels may be included in other portions of the catheter where it is desired to impart a bias. For example, FIG. 72 illustrates a configuration wherein a superelastic channel 7210 is used to bias the distal end 144 in an arcuate curve. The superelastic channel 7210 may be incorporated within a lumen of the catheter, with a wall of the catheter, or elsewhere within the catheter. The arcuate shape may be fixed, as shown in FIG. 72, such that the arcuate curve is not manipulable via a pull cable. Alternatively, an active curve may be achieved by including a pull cable (e.g., in a lumen on the inner portion of the curve) manipulable to control the radius of the curve. Manipulation of the curve of FIG. 72 may occur in the same manner as described in connection with FIGS. 39A-B.

Electrode Configurations

As noted above, embodiments are not limited to a particular construction, type, or number of electrodes disposed along the distal end of the tip assembly. For example, embodiments may include a plurality of low-profile ring type electrodes 146 disposed along the distal end of the tip assembly 140, such as shown in FIG. 2, with or without a distal end or cap electrode 147. Alternatively, a plurality of raised profile ring type electrodes may be used, such as the electrode 1546 illustrated in FIG. 15A, with or without a distal end or cap electrode 147. Alternatively still, a combination of raised and low profile electrodes may be used.

Where multiple mapping electrodes are used, pairs of mapping electrodes 146 (FIG. 2) may be used to determine a location of lowest conductivity on the septal wall, or a preferred location to puncture the septal wall during a transeptal procedure. Each of the mapping electrodes 146 may detect a voltage signal, which is transmitted to controller 150 via cable 115 (FIG. 1). Voltage may be measured instantaneously or continuously by each of the electrodes 146. Continuous voltage measurements generate an electrogram (a voltage signal that changes with time) for each electrode. The voltage detected by each electrode may be determined with respect to a reference electrode, termed a unipolar voltage measurement, or may be determined with respect to another electrode of a pair, termed a bipolar voltage measurement. Thus, a pair of mapping electrodes may generate two unipolar electrograms, each with respect to a reference electrode located elsewhere on the catheter 100, or a single bipolar electrogram representing the voltage between each pair of electrodes. As unipolar and bipolar voltage measurement are well understood by those skilled in the art, further discussion is omitted herein.

It should be appreciated that the electrodes may be constructed from a variety of materials, including non ferromagnetic materials such as gold, platinum, and silver, or they may be constructed from a conductive epoxy. The electrodes may be individual electrodes, or may be continuous electrodes, similar in construction to a coiled spring wrapped about the distal end of the tip assembly. The electrodes may be fixed in position along the distal end of the tip assembly, or alternatively, may be movable along a length of the distal end of the tip assembly. An example of such a movable electrode is now described with respect to FIG. 18.

As shown in FIG. 18, the distal end 144 of the tip assembly 140 may include a movable electrode 1846 that is movable between a first position and a second position spaced apart along a length of the distal end 144 of the tip assembly 140. In the embodiment illustrated, the movable electrode 1846 slides along a length of the distal end 144 than spans approximately 360 degrees, and when used for ablation, may be used to form a circular lesion. The very distal end of the tip assembly may include a cap electrode 1847, or alternatively, the cap may be made from a non-conductive material and may simply serve to terminate the very distal end of the tip assembly. Where a cap electrode 1847 is used, an insulating spacer may be placed proximally of the cap electrode to prevent the movable electrode 1846 from electrically contacting the cap electrode 1847.

As shown in FIG. 19, which is a cross sectional side view of the distal end of the tip assembly in FIG. 18 taken along line 19-19, the electrode 1846 may be attached to a cylindrically-shaped plastic slider 1910 that that can slide back and forth along a length of the distal end 144 of the tip assembly. In the embodiment shown, the distal end of a metal push/pull wire 1920 is welded to an outer surface of the electrode 1846, with the proximal end of the push/pull 1920 wire being attached to an actuator 122, 124 on the handle 120. The push/pull wire 1920 may be disposed within the central lumen 1125 from the handle 120 to the intermediate section 1480 of the tip assembly 140 (FIG. 15), wherein it then passes through one of the outer lumens 1110c, 1110d of the distal section. The distal end of the push/pull wire 1920 emanates through a slit 1930 in the core 1120. It should be appreciated that in embodiments where it is desired that the push/pull wire 1920 not be electrically connected to the electrode, the push/pull wire 1920 may be attached to the plastic slider 1910, rather than to the electrode 1846. It should also be appreciated that the push/pull wire 1920 need not be made from metal, as non-conducting materials may also be used, as known to those skilled in the art.

FIG. 20 is a cross sectional end view of distal end of the tip assembly illustrated in FIG. 19, taken along line 20-20. FIG. 20 illustrates the slit 1930 in the core 1120 through which the push/pull wire 1920 protrudes, with the remaining elements having already been described. Further details of the sliding electrode described with respect to FIGS. 18-20 are provided in commonly assigned U.S. Pat. No. 6,245,066, which is hereby incorporated by reference in its entirety.

The Handle

Figure 22:
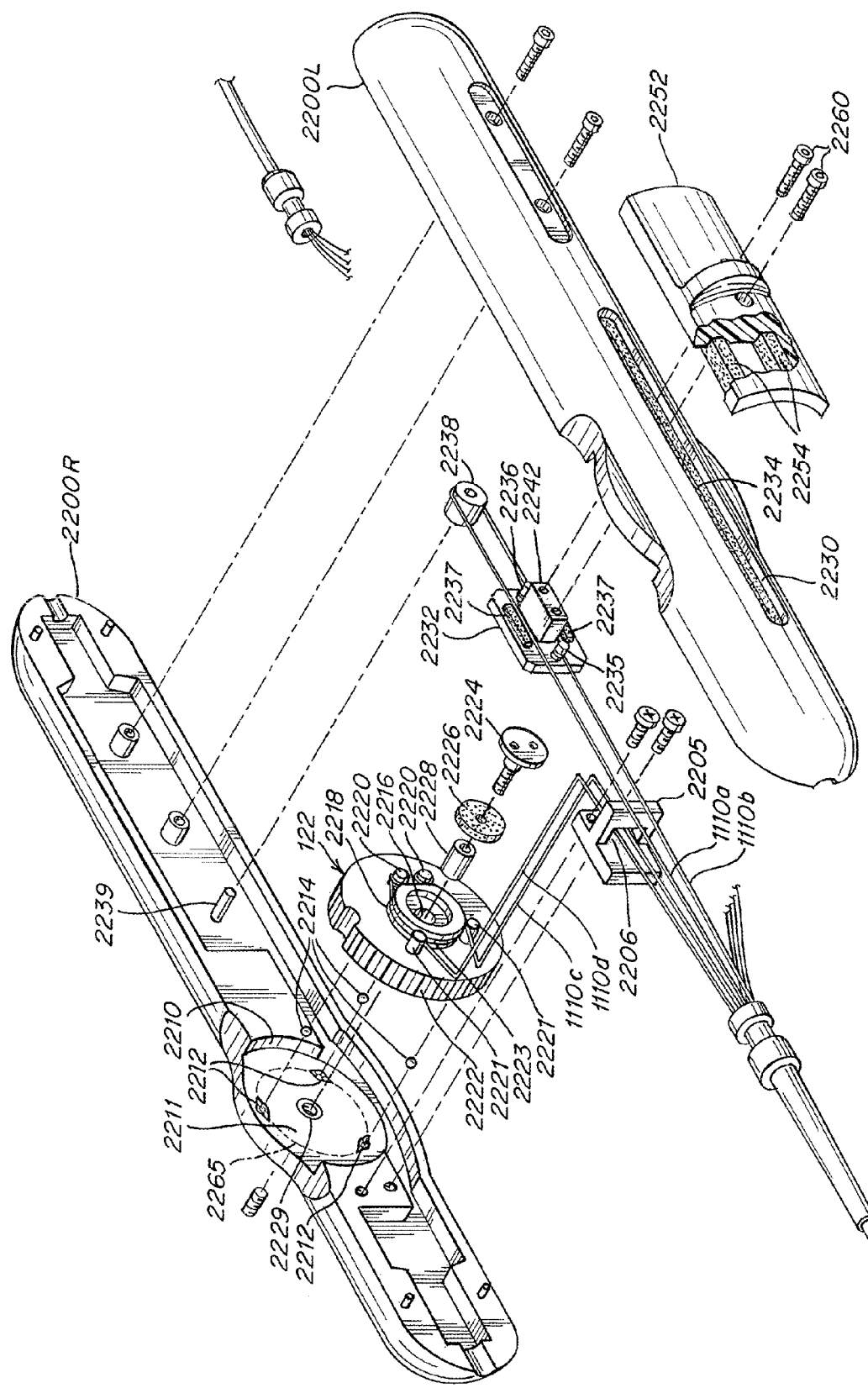
FIG. 22 is an exploded view of a handle, taken along line 22-22 in FIG. 1, that may be used with the catheter system of FIG. 1 according to another embodiment of the present invention.

A handle assembly in accordance with one embodiment of the invention, is shown in FIGS. 22-33. The handle configuration shown in these drawings uses rotational movement of the thumbwheel actuator 122 to selectively control the tension applied to the pull cables 1110c and 1110d which control the orientation of the tip assembly 140 relative to the longitudinal axis of the shaft 110, and linear movement of the slide actuator 124 to selectively control the tension applied to pull cables 1110a and 1110b that control the radius of curvature of the distal end 144 of the tip assembly 140. Referring to FIG. 22, the handle 120 comprises a housing having a left section 2200L and a right section 2200R. These two sections 2200L and 2200R are somewhat semicircular in cross section and have flat connecting surfaces which may be secured to each other along a common plane to form a complete housing for the handle 120. The outer surfaces of the handle 120 are contoured to be comfortably held by the user.

A wheel cavity 2210 is formed within the right section 2200R of the handle 120. The wheel cavity 2210 includes a planar rear surface 2211 which is generally parallel to the flat connecting surface of the handle 120. The thumb wheel actuator 122 is a generally circular disc having a central bore 2216, an integrally formed pulley 2218, and upper and lower cable anchors 2220. Upper and lower cable guides 2221 serve to retain the cables 1110c and 1110d within a guide slot or groove 2223 formed in a surface of the integrally formed pulley 2218. In the embodiment illustrated, the thumbwheel 122 rotates about a sleeve 2228 inserted in the central bore 2216. The thumbwheel 122 is held in position by a shoulder nut 2224 that mates with a threaded insert 2229 in the planar rear surface 2211 of the right section 2200R of the handle 120. To provide friction that permits the thumbwheel to maintain its position even when tension is applied to one of the cables 1110c, 1110d, a friction disk 2226 is provided between the shoulder nut 2224 and the thumbwheel 122. Tightening of the shoulder nut 2224 increases the amount of friction applied to the thumbwheel 122.

A peripheral edge surface 2222 of the thumb wheel 122 protrudes from a wheel access opening so that the thumb wheel 122 may be rotated by the thumb of the operator's hand which is used to grip the handle 120. To ensure a positive grip between the thumb wheel 122 and the user's thumb, the peripheral edge surface 2222 of the thumb wheel 122 is preferably serrated, or otherwise roughened. Different serrations on opposite halves of thumb wheel 122 enable the user to "feel" the position of the thumb wheel.

The left section 2200L supports part of the mechanism for selectively tensioning each of the two pull cables 1110a and 1110b that control the radius of curvature of the distal end 144 of the tip assembly 140. To accommodate the protruding portion of the thumb wheel 122, the left handle section 2200L includes a wheel access opening similar in shape to the wheel access opening of the right handle section 2200R. It also includes an elongated slot 2230 in its side surface.

A slider 2232 is provided with a neck portion 2242 which fits snugly within the slot 2230. The slider 2232 includes a forward cable anchor 2235 and a rear cable anchor 2236 for anchoring the pull cables 1110a and 1110b. Pull cable 1110b is directly attached to the forward cable anchor 2235 and becomes taught when the slider 2232 is moved toward the distal end of the handle 120. Pull cable 1110a is guided by a return pulley 2238 prior to being attached to the rear cable anchor 2236 and becomes taught when the slider 2232 is moved toward the proximal end of the handle 120. The return pulley 2238 is rotatably attached to a pulley axle 2239 which is supported in a bore (not shown) in the flat surface of the right handle section 2200R. The return pulley 2238 may include a groove (not shown) to guide pull cable 1110a. In the illustrated embodiment, a cable guide 2205 is attached to the right handle section 2200R to guide the cables 1110a-1110d and prevent their entanglement with one another. As shown, cables 1110a and 1110b are routed up and over the cable guide 2205, while cables 1110c and 1110d are routed through a gap 2206 in the cable guide 2205. Grooves may be formed in a top surface of the cable guide 2205 to keep cables 1110a and 1110b in position, although they could alternatively be routed through holes formed in the cable guide 2205, or by other suitable means.

A slider grip 2252 is attached to the neck portion 2242 of the slider 2232 and positioned externally of the handle 120. The slider grip 2252 is preferably ergonomically shaped to be comfortably controlled by the user. Together, the slider 2232 and the slider grip 2252 form the slide actuator 124 depicted in FIG. 1. Preload pads 2254 are positioned between the outer surface of the left handle section 2200L and the slider grip 2252 (shown in FIGS. 22 and 25). By tightening the screws 2260 that attach the slider grip 2252 to the slider 2232, friction is applied to the slider 2232 and thus, to the pull cables 1110a, 1110b. Preload pads 2237 may also be placed on a surface of the slider 2232 for a similar purpose.

A dust seal 2234 (FIGS. 22 and 26) having an elongated slit and preferably made from latex is bonded along the slot 2230 within the left handle section 2200L. The neck portion 2242 of the slider 2232 protrudes through the slit of the dust seal 2234 so that the slit only separates adjacent to the neck portion 2242. Otherwise, the slit remains "closed" and functions as an effective barrier preventing dust, hair and other contaminants from entering the handle 120. Further details of the handle 122 are described in U.S. Pat. Nos. 5,383,852, 5,462,527, and 5,611,777.

According to a further aspect of the present invention, each of the thumbwheel actuator and the slide actuator may include means for imparting a first amount of friction on at least one pull cable to which the actuator is attached when the actuator is in a first position, and for imparting a second and greater amount of friction on the at least one pull cable when the actuator is moved away from the first position. According to this aspect of the present invention, the first position may correspond to a neutral position of the actuator wherein the tip assembly is aligned with the longitudinal axis of the shaft, or a neutral position of the actuator wherein the radius of curvature of the distal end of the tip assembly is neither being actively reduced or increased, and the second position may correspond to a position of the actuator that is other than the neutral or rest position.

As should be appreciated by those skilled in the art, it is desirable that the actuators for changing the orientation of the tip assembly and for controlling the radius of curvature of the distal end of the tip assembly remain in a fixed position, once actuated. Conventionally, this has been achieved by providing a sufficient amount of friction between the actuator and another surface on the handle 122 to resist movement of the actuator unless a certain amount of force is applied to the actuator. For example, in FIG. 22, by tightening shoulder nut 2224 that holds the thumbwheel in position, a greater amount of force must be applied to the thumbwheel to rotate the thumbwheel from one rotational position to another. Similarly, and with respect to the slide actuator 124, by tightening the two screws 2260 that hold the slider grip 2252 in position against an undersurface of the handle section, a greater amount of force must be applied to the slide actuator 124 to move the slide actuator 122 from one position to another.

Although this conventional approach is straightforward, it results in the same amount of friction being applied to the actuator(s) in all positions, and not merely those positions that deviate from a neutral or rest position. Thus, in use, it can be difficult to ascertain whether the orientation of the tip assembly or the radius of curvature of the distal end of the tip assembly is in a neutral state, without visually looking at the handle. This can be problematic, as the user of the catheter would need to divert his or her attention to visually inspect the position of the actuator(s). Further, Applicants have determined that the frictional force imparted by the mechanisms that maintain the cables and actuators in a fixed position can significantly decrease over time, for example, while stacked on the shelf, oftentimes requiring that the mechanisms used to impart such friction (e.g., the shoulder nut and the screws) be tightened prior to use. It is believed that this phenomena is due to material creep associated with the various materials used to form the actuator mechanisms. This decrease in frictional force is especially apparent where the catheter has been brought to elevated temperatures during a sterilization cycle, as the materials from which the handle and the control mechanisms are formed have a tendency to yield at elevated temperatures. Although the various mechanisms may be tightened after sterilization, such tightening may contaminate the sterile nature of the catheter, and is undesirable in a clinical setting.

According to a further aspect of the present invention, each of the thumbwheel actuator and the slide actuator may include means for imparting a first amount of friction on at least one pull cable to which the actuator is attached when the actuator is in a first position, and for imparting a second and greater amount of friction on the at least one pull cable when the actuator is moved away from the first position. This difference in the frictional force can be perceived by the user to alert the user as to when the actuator is in a neutral or rest position, without visually inspecting the actuator. Further, because the frictional forces on the actuating mechanisms are reduced in a neutral or rest position, the catheter may be sterilized with the actuator(s) in a neutral or rest position, thereby reducing yielding of the actuation mechanism during sterilization.

According to one embodiment that is directed to the thumbwheel actuator, the means for imparting different amounts of friction may include a plurality of detents formed in the planar rear surface of the handle housing that cooperate with corresponding plurality of detents in a lower surface of the thumbwheel. In this embodiment, each of the plurality of detents in the lower surface of the thumbwheel receives a ball or bearing that sits partially within the respective detent. In a first neutral position, each of the balls also rest within a respective detent in the rear surface of the handle and exert a first amount of friction on the thumbwheel and the pull cables attached thereto. But, as the thumbwheel is rotated, the balls ride outside the detent in the rear surface of the handle onto the elevated surface above, thereby exerting a second and greater amount of friction on the thumbwheel and the pull cables attached thereto. According to one embodiment, this second amount of friction is sufficient to prevent the thumbwheel from returning to its neutral position. FIGS. 22, 26, 27, and 28 illustrate one implementation of a means for imparting different amounts of friction for a thumbwheel actuator 122 according to this embodiment of the present invention.

Figure 26:
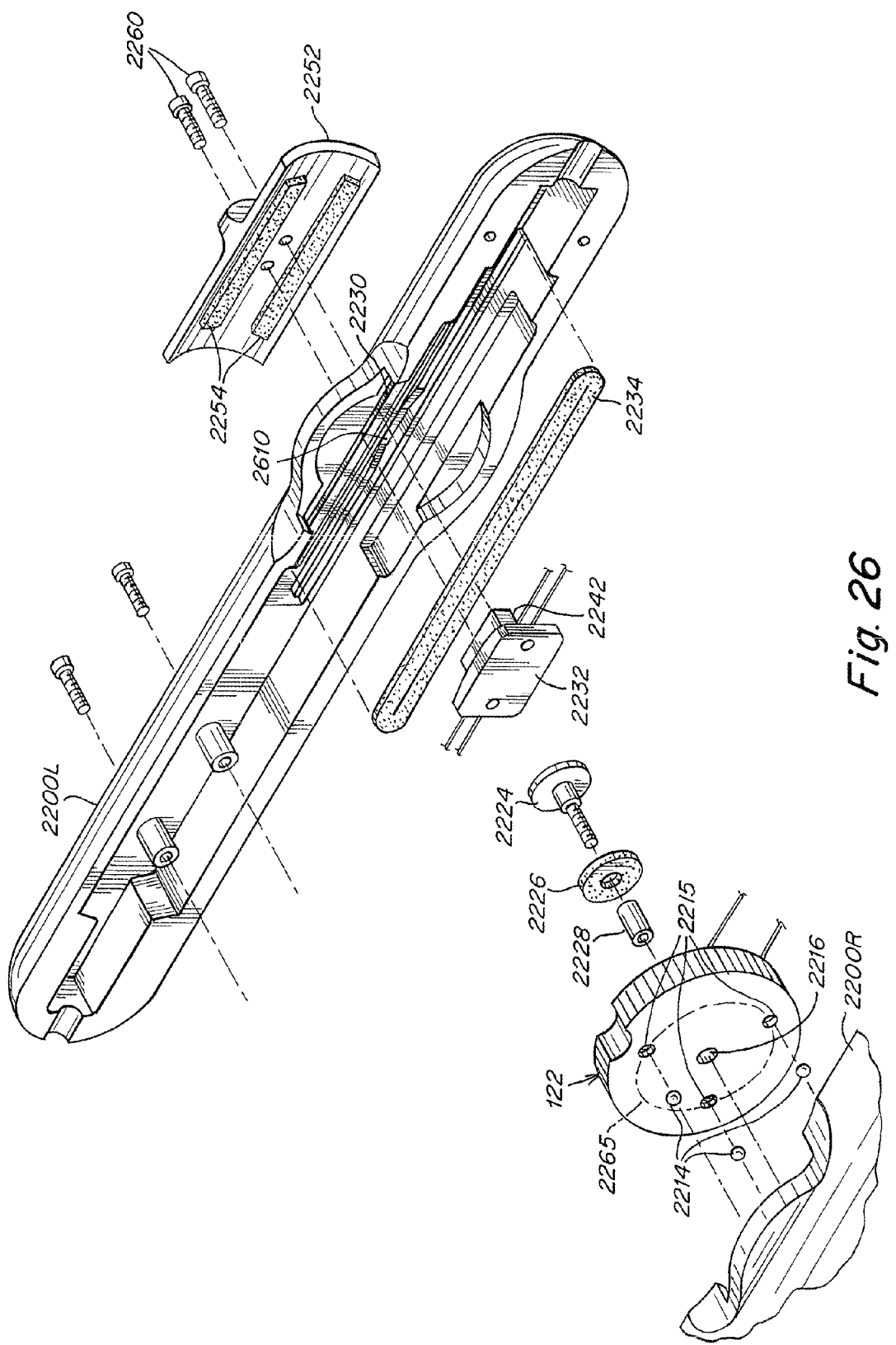
FIG. 26 is an exploded perspective view of the left section of the handle of FIG. 22.
Figure 27:
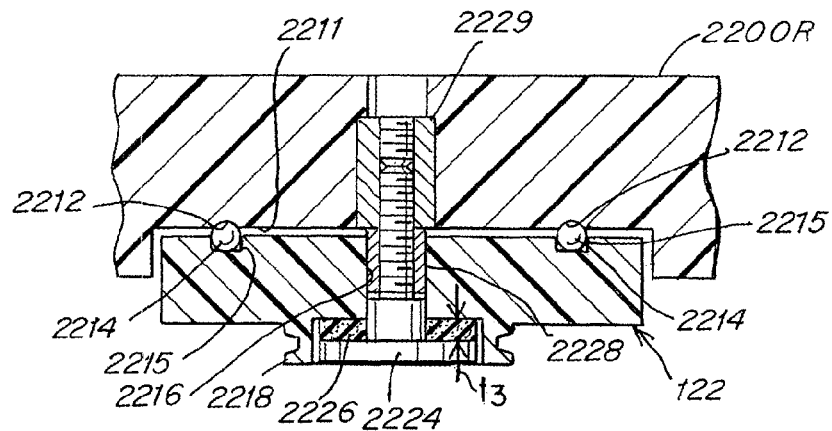
FIG. 27 is a schematic cross sectional view of a thumb-wheel actuator for the handle of FIG. 22 in a neutral or unloaded state.
Figure 28:
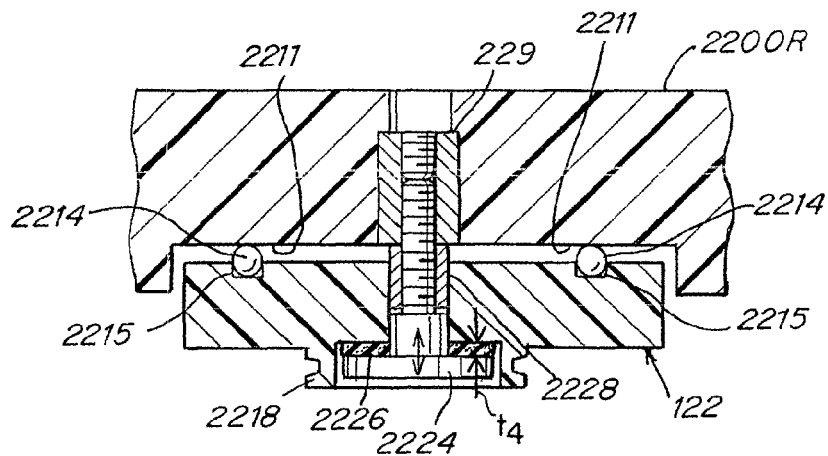
FIG. 28 is a schematic cross sectional view of the thumb-wheel actuator for the handle of FIG. 22 in a deployed or loaded state.

As shown in FIGS. 22, 26, 27, and 28, the planar rear surface 2210 of the right section 2200R includes a plurality of detents 2212 formed therein. A corresponding number of detents 2215 are provided in an undersurface of the thumbwheel 122 (FIGS. 26-28). Within each of the plurality of detents 2215 in the undersurface of the thumbwheel is a ball or bearing 2214. The balls or bearing may be made from any suitable material, such as stainless steel, or may alternatively be made from a hard plastic. The balls or bearings 2214 may be fixed in position for example, with an epoxy, or permitted to rotate within the detents 2215. It should be appreciated that the balls or bearings 2214 may alternatively be seated within the detents 2212 in the planar rear surface 2211 of the right section of the handle 2200R. In a neutral or rest position, for example, corresponding to an orientation of the tip assembly that is parallel to the longitudinal axis of the shaft, each of the plurality of balls rests within a corresponding detent 2212 in the planar rear surface 2211. Such a resting or neutral state is depicted in FIG. 27 which is a schematic cross sectional view of the thumbwheel of FIG. 22. As may be appreciated, this neutral or rest position corresponds to a position of reduced friction on the thumbwheel 122 in which the friction disk 2226 is compressed to only a small degree, and thus, to a reduced frictional force on the pull cables that are attached to the thumbwheel.

As the thumbwheel 122 is rotated from this neutral or rest position, the balls 2214 ride up and out of their respective detents 2212 and along the path 2265 indicated in FIG. 22. In this second position wherein each of the balls contacts the elevated planar rear surface 2211, a second and greater amount of friction is imparted to the thumbwheel, and thus, the pull cables attached thereto, that tends to prevent the thumbwheel from moving to another position without further rotational force applied to the thumbwheel. FIG. 28 is a schematic cross sectional view of the thumbwheel of FIG. 22 illustrating a state in which the thumbwheel is in a position other than the neutral or rest position. As can be seen in FIG. 28, each of the balls 2214 rests upon the elevated planar rear surface 2211 and the friction disk 2226 is compressed relative to that shown in FIG. 27. As shown best in FIG. 22, each of the detents 2212 in the planar rear surface 2211 may include lead in/lead out sections 2267 that are gradually tapered to the level of the planar rear surface 2211 to facilitate smooth movement of the balls 2214 out of and into the detents 2212.

Although the present invention is not limited to the number of detents 2212, 2215 incorporated into the handle and the thumbwheel, Applicants have found that three detents spaced equally about a circumference of the planar rear surface 2211 and the thumbwheel 122 distributes stress evenly about the thumbwheel 122 and permits a sufficient amount of rotation before another detent 2212 is encountered. Furthermore, although the present invention is not limited to the amount of force applied to the thumbwheel to change the position of the thumbwheel, Applicants have empirically determined that a force of approximately 4 to 8 pounds is sufficient to resist any forces on the pull cables. Moreover, this amount of force is sufficient so that the thumbwheel cannot be moved inadvertently, and does not require great strength by the user. This amount of force also accounts for any yielding during storage and/or sterilization.

Although this embodiment has been described in terms of a plurality of detents in a surface of the handle and a corresponding number of detents that hold a ball or bearing in an undersurface of the thumbwheel, the present invention is not so limited. For example, and as discussed above, the detents in the planar surface 2211 of the handle 120 may hold the balls or bearings 2214 and not the thumbwheel. Moreover, it should be appreciated that other means of imparting different frictional forces on the thumbwheel may be readily envisioned. For example, rather than detents, the rear planar surface 2211 may be contoured to include a plurality of ramps (for example, three ramps). The undersurface of the thumbwheel 122 may include a corresponding plurality of complementary shaped ramps such that when the thumbwheel 122 is in a neutral or rest position, a minimum of friction is imparted, and as the thumbwheel 122 is rotated, the heightened surface of the ramps on the undersurface of the thumbwheel 122 contacts a heightened surface of the ramps in the planar surface. As the thumbwheel 122 is rotated further, addition friction is imparted.

According to another embodiment that is directed to the slide actuator, the means for imparting different amounts of friction may include a ramp disposed on or formed within the handle 120. In this embodiment, the apex of the ramp corresponds to a neutral position of the slide actuator 122. In this neutral position, a minimum amount of friction is applied to the slider 2232 and the pull cables 1110a, 1110b attached thereto. As the slider 2232 is moved forward or backward away from the neutral position, the slider 2232 is pushed toward the thumbwheel and an interior surface of the housing to impart a great amount of friction on the slider and the pull cables attached thereto. As with the thumbwheel, this second amount of friction is sufficient to prevent the slider from returning to its neutral position.

Figure 23:
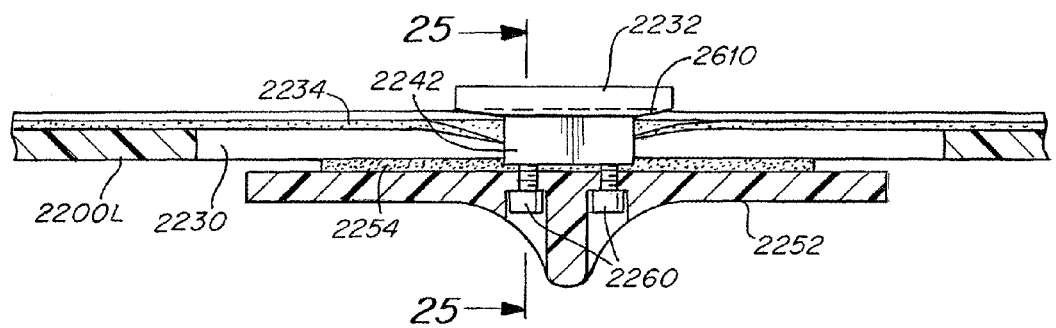
FIG. 23 is a schematic cross sectional view of a slide actuator for the handle of FIG. 22 in a neutral or unloaded state.
Figure 24:
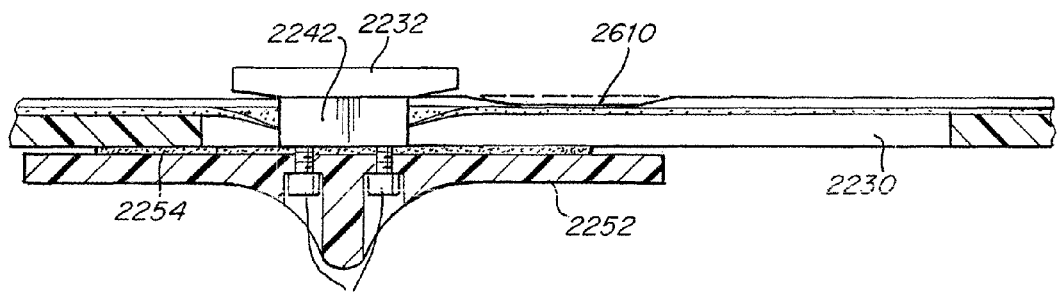
FIG. 24 is a schematic cross sectional view of a slide actuator for the handle of FIG. 22 in a deployed or loaded state.
Figure 25:
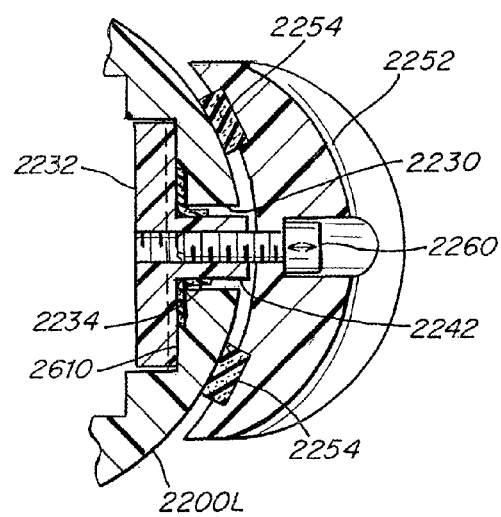
FIG. 25 is a cross sectional end view of the slide actuator of FIG. 23 taken along line 25-25 in FIG. 23.

FIGS. 23, 24, and 26 illustrate one implementation of a means for imparting different amounts of friction for a slide actuator 124. As shown in these Figures, the undersurface of the left section 2200L includes a ramp 2610. The ramp may be integrally formed within the left section 2200L of the handle 120, or alternatively, the ramp 2610 may be separate from the handle and attached thereto. As illustrated in FIG. 26 which is a schematic cross sectional view of the slide actuator 124 shown in FIGS. 1 and 22, the ramp 2610 includes a central section of decreased thickness and proximal and distal sections that increase in thickness away from the central section until flush with the undersurface of the left section. The top surface of the slider 2232 that contacts the undersurface of the left section 2200L of the handle may have a complementary shape to the ramp as shown in FIGS. 23 and 24. In the position shown in FIG. 23, the slide actuator is in a neutral or rest position corresponding to a first radius of curvature of the distal end of the tip assembly. The two screws 2260 force the slider grip 2252 and the slider 2232 closer to one another and compress the preload pads 2254 therebetween. In the neutral or rest position shown in FIGS. 23 and 25, the preload pads 2254 are compressed to only a minimal extent. However, as the slider 2232 is moved away from the neutral or resting position, the shape of the ramp 2610 (and the slider 2332) imparts an additional frictional force that tends to separate the slider 2232 from the slider grip 2252, thereby compressing the preload pads 2254 to a greater extent, as illustrated in FIG. 24. This additional frictional force resists the slide actuator 124 from changing position, absent further force on the slide actuator 124.

Although this embodiment has been described in terms of a ramp formed within or disposed on an undersurface of the handle 122, the present invention is not so limited. For example, the ramp may alternatively be formed on an outer surface of the handle and provide similar functionality. Other means for imparting different frictional forces on the slide actuator may be readily envisioned by those skilled in the art.

Although the above described embodiments for imparting a varying amount of friction on at least one pull cable have been described with respect to a catheter in which the diameter of curvature of the distal end, or the orientation of the distal end of the tip assembly, can be changed by manipulation of an actuator attached to the pull cable, the present invention is not so limited. For example, the means for imparting a varying amount of friction may also be used with a push/pull cable and a movable electrode described above. Alternatively, the means for imparting a varying amount of friction may be used to impart varying amounts of friction to a cable that is used to deploy a braided conductive member in the manner described in co-pending and commonly assigned U.S. patent application Ser. No. 09/845,022, entitled APPARATUS AND METHODS FOR MAPPING AND ABLATION IN ELECTROPHYSIOLOGY PROCEDURES, filed Apr. 27, 2001, and incorporated herein by reference. Accordingly, it should be appreciated that this embodiment may be used to impart varying amounts of friction on any cable that controls movement of one portion of the catheter with respect to another.

Figure 29A:
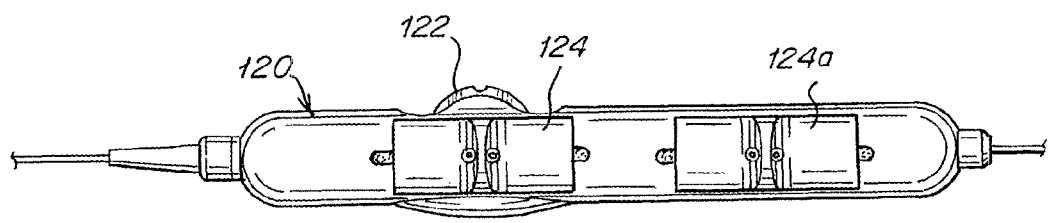
FIG. 29A is an elevational view of another handle that may be used with the catheter system of FIG. 1 according to another embodiment of the invention that includes a third actuator.

FIG. 29A illustrates another handle that may be used with embodiments of the present invention. In the embodiment depicted in FIG. 29A, the handle 120 includes three actuators 122, 124, and 124a for controlling movement of the tip assembly 140. For example, the thumbwheel actuator 122 may be used to change the orientation of the tip assembly 140 relative to the longitudinal axis of the shaft 110 of the catheter 100 in one or two different directions depending on the number of cables attached thereto. The first slide actuator 124 may be used to increase and/or decrease the radius of curvature of the distal end 144 of the tip assembly 140. The second slide actuator 124a may be used to control the orientation of the of the tip assembly 140 relative to the longitudinal axis of the shaft 110 of the catheter 100 in one or two different direction of movement that are orthogonal to the directions provided by use of the thumbwheel actuator 122. Alternatively, the second slide actuator 124A may be used to move a sliding electrode (See FIG. 18) proximally and distally along the distal end of the tip assembly. Alternatively still, the thumbwheel actuator 122 or the first slide actuator 124 may be used for changing the orientation of the tip assembly or the radius of curvature of the distal end in a first direction, and the second slide actuator 124a may be used for changing the orientation of the tip assembly or the radius of curvature in the opposite direction. Alternatively still, the first slide actuator 124 may be used for controlling an active bend (see FIG. 21), the thumbwheel actuator 122 may be used for changing the radius of curvature of the distal end of the tip assembly, and the second slide actuator 124a may be used for changing the orientation of the tip assembly in a first and/or second direction (e.g., for steering of the proximal end of the tip assembly.)

Figure 29B:
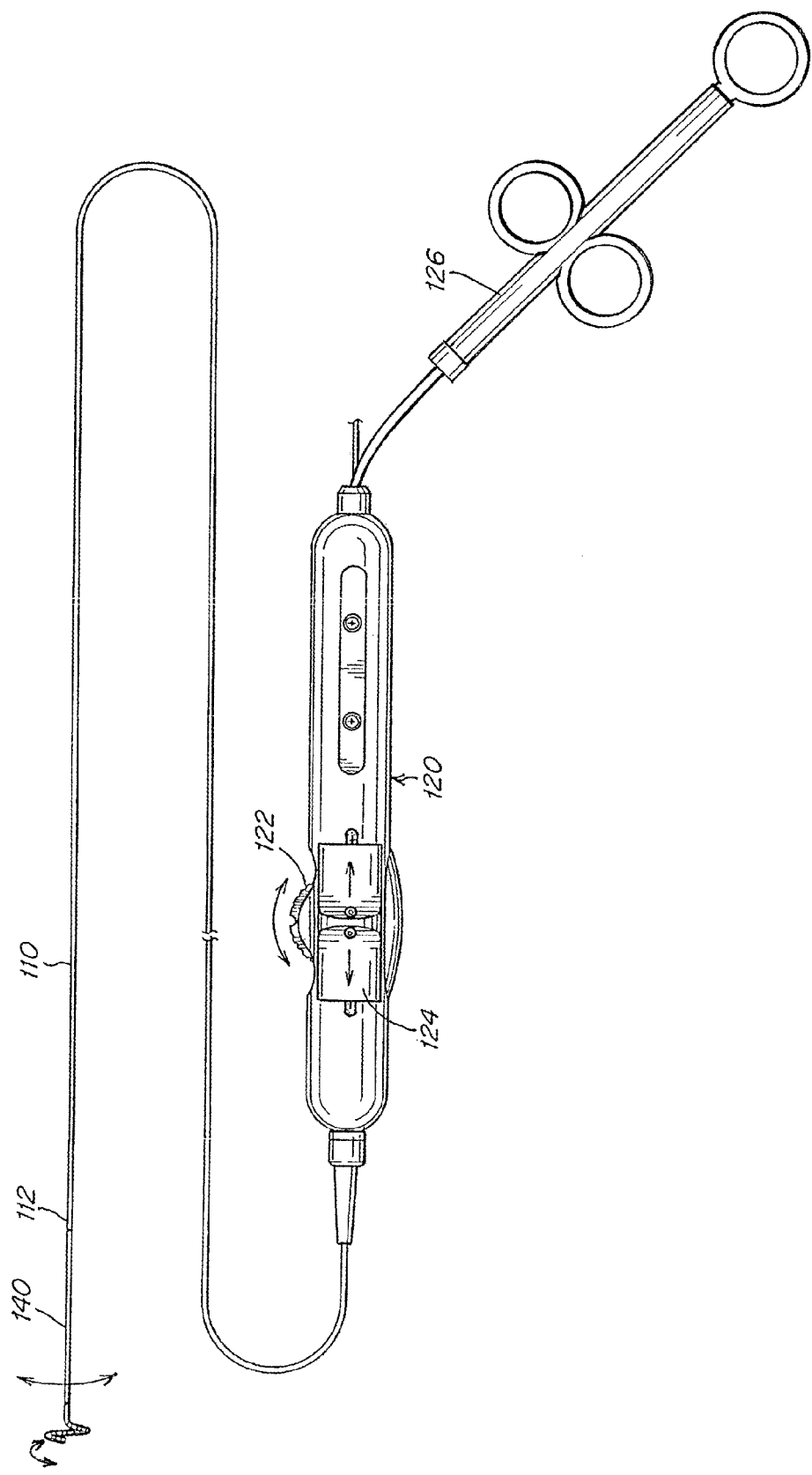
FIG. 29B is a schematic view of another handle according to another embodiment of the invention that includes a plunger-type third actuator.

FIG. 29B illustrates another handle that includes a third actuator. In the embodiment illustrated in FIG. 29B, the third actuator is a plunger-type actuator 126 that is conventionally used for a variety of different purposes in the medical industry. In the illustrated embodiment, the plunger-type actuator may be used to move a sliding electrode proximally and distally along the distal end of the tip assembly, with the thumbwheel 122 and slide 124 actuators being used for steering of the proximal end of the tip assembly and changing the radius of curvature of the distal end of the tip assembly, respectively, or vice versa. Although the use of a handle having up to three different actuators has been described, it should be appreciated that more than three different actuators may be provided. For example, a thumbwheel actuator, two slide actuators, and a plunger-type actuator may be used to control an active bend, a sliding electrode, changing the radius of curvature of the distal end, and steering of the proximal end of the tip assembly.

Figure 30:
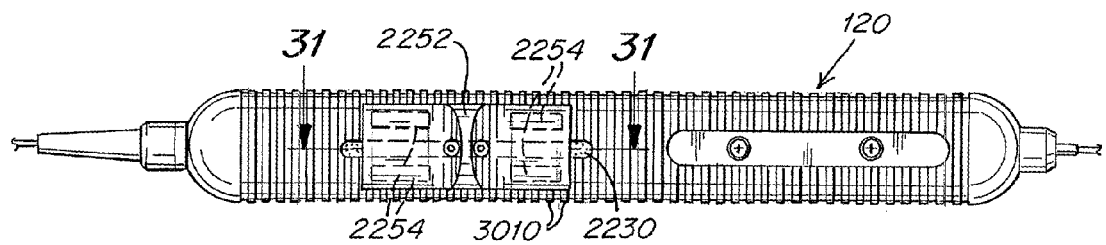
FIG. 30 is a side elevational view of a handle that may be used with the catheter system of FIG. 1 and which includes features that provide tactile feedback to a user when using one of the actuators.
Figure 31:
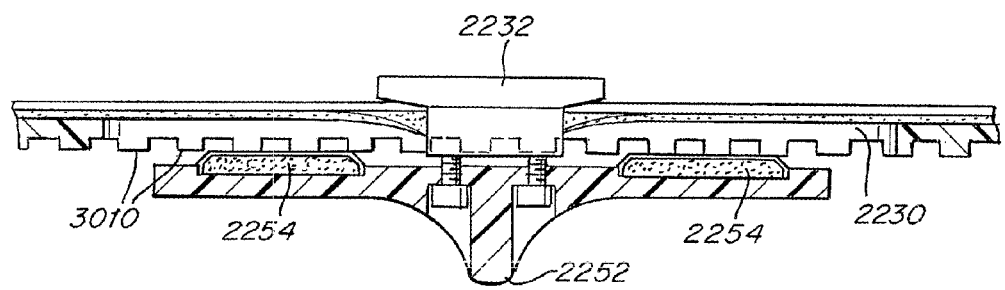
FIG. 31 is a schematic cross sectional view of one implementation for providing tactile feedback to a user that is adapted for use with the slide actuator of FIG. 30.
Figure 32:
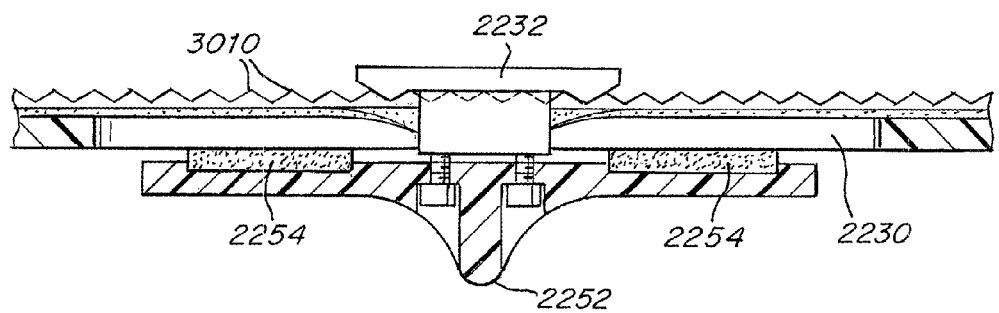
FIG. 32 is a schematic cross sectional view of another implementation for providing tactile feedback to a user that is also adapted for use with the slide actuator of FIG. 30.

FIGS. 30-32 illustrate a control handle for a catheter according to another embodiment of the present invention. As illustrated in FIG. 31, a surface of the handle 120 may include a plurality of ribs or detents 3010 to provide tactile feedback to a user. For example, as the slider grip 2252 is moved proximally and distally on the handle, this movement can be felt by the user. Such feedback permits the user to understand that the radius of curvature of the distal end of the tip assembly, or the orientation of the tip assembly has been changed, without requiring the user to visually perceive the movement of the slider grip 2252. In the embodiment illustrated in FIG. 31, the plurality of ribs are formed integrally with the handle 120 and disposed on an outer surface thereof. To prevent the preload pads 2254 from catching on the ribs or detents 3010, a hard thin layer of material such as plastic may be applied to the surface of the preload pads that contact the outer surface of the handle 120. In the embodiment shown, the leading and trailing edges of the pads 2254 are also curved away from the outer surface of the handle 120 to avoid rough movement.

FIG. 32 illustrates an alternative embodiment of the handle 120 that includes a plurality of ribs or detents 3010 that are formed integrally with the handle 120 and disposed on an inner surface of the handle 120. As the preload pads 2252 do not directly contact the ribs or detents 3010, a hard layer such as that described above with respect to FIG. 31 is not necessary. With each of the embodiments described above, it should be appreciated that the ribs or detents 3010 should be large enough to provide tactile feedback to the user, but not so large as to be disturbing to the user, or to result in rough and abrupt movement of the slide actuator 124 when moved from one position to another. Applicants have empirically determined that a protrusion of the ribs or detents 3010 approximately 1 mm above, or below the surface of the handle meets these objectives. Although the use of ribs or detents has been described with respect to providing feedback to a user on movement of the distal end of the catheter, the present invention is not so limited. For example, the ribs or detents may be used to provide feedback relating to movement of a movable electrode, or a braided conductive mesh. Accordingly, the use of tactile features for providing feedback to a user may be used wherever it is useful to provide feedback to a user on the movement of one portion of the catheter with respect to another.

According to another embodiment of the present invention, a handle for use with a catheter having an elongated shaft and a tip assembly is provided. According to this embodiment, the handle may include graphical indicia indicative of a radius of curvature of a distal end of the tip assembly. This embodiment is now described with respect to FIG. 33.

Figure 33:
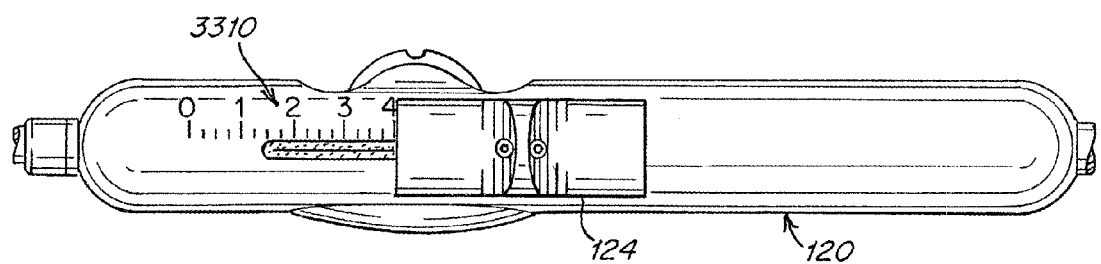
FIG. 33 is a side elevational view of an handle that includes graphical indicia indicative of a radius of curvature of the distal end tip assembly according to another embodiment of the present invention.

As shown in FIG. 33, the handle 120 of the catheter 100 can include graphical indicia 3310 that identifies the radius of curvature of the distal end of the tip assembly. In the embodiment shown, the graphical indicia 3310 are disposed on the handle 120 adjacent to the slide actuator 124, which in this embodiment controls the radius of curvature of the distal end of the tip assembly. As illustrated, the graphical indicia 3310 identify the diameter of curvature in centimeters, with a position of two centimeters corresponding to a neutral position of the slide actuator. Movement of the slide actuator 124 distally on the handle 120 increases the radius of curvature of the distal end of the tip assembly, and movement of the slider 124 proximally on the handle 120 decreases the radius of curvature. Although not illustrated in FIG. 33, the graphical indicia 3310 may also identify the number of circles formed by the distal end of the tip assembly. For example, a first numeric indicator can precede each of the illustrated numeric indicators to identify the number of circles formed by the distal end of the tip assembly. For example, an indicator of 2.1 can indicate two complete circles of the distal end of the tip assembly with a diameter of 1 cm, with an indicator of 1.2 indicating one complete circle of the distal end of the tip assembly with a diameter of 2 cm. Alternatively, the number of circles formed by the distal end of the tip assembly may be placed on the other side of the slide actuator 124. Other representations of both the diameter of curvature and the number of circles formed by the distal end of the tip assembly may be readily envisioned. It should be appreciated that the graphical indicia permit a user to roughly determine the diameter of an endocardial or epicardial site without recourse to other instrumentation, other than the catheter itself.

Although the provision of graphical indicia has been described with respect to the slide actuator 124, it should be appreciated that a similar provision may be made for the thumbwheel actuator 122. In general, although the provision of graphical indicia may associated with the thumbwheel 122 may not be very useful when related to the orientation of the tip assembly, the operation of the thumbwheel 122 and the slide actuator 124 may be reversed, such that the thumbwheel 122 is used to control the radius of curvature of the distal end of the tip assembly, and the slide actuator 124 is used to control the orientation of the tip assembly. Where the thumbwheel 122 is used to control the radius of curvature of the distal end of the tip assembly, graphical indicia 3010 may be provided on the thumbwheel at different rotational positions (e.g., at zero degrees, at thirty degrees, as sixty degrees, etc. to serve a similar purpose.

Although the provision of graphical indicia has been described with respect to providing feedback to a user on the radius of curvature of the distal end of the catheter, it should be appreciated that other uses may be readily envisioned. For example, the use of graphical indicia may be used to identify the state of deployment of a braided mesh that is disposed at the distal end of the catheter, or to identify the location of a movable electrode that is disposed on the distal end of the catheter.

Temperature Sensing and Localization

Temperature sensing refers to a number of techniques whereby the temperature in the vicinity surrounding distal end 144 of the tip assembly 140 may be measured. Measuring temperature is important, particularly during ablation procedures, so as to avoid overheating or charring tissue. The catheter can provide for measuring the temperature of the distal end 144 of the tip assembly 140 and the mapping electrodes disposed thereon at the same time. The temperature of the distal end 144 can then be used to provide feedback for control of ablation energy generator 170 and the temperature of the mapping electrodes can be monitored to be certain that the tissue that is being ablated is in fact being destroyed or rendered non-electrically conductive.

Figure 34:
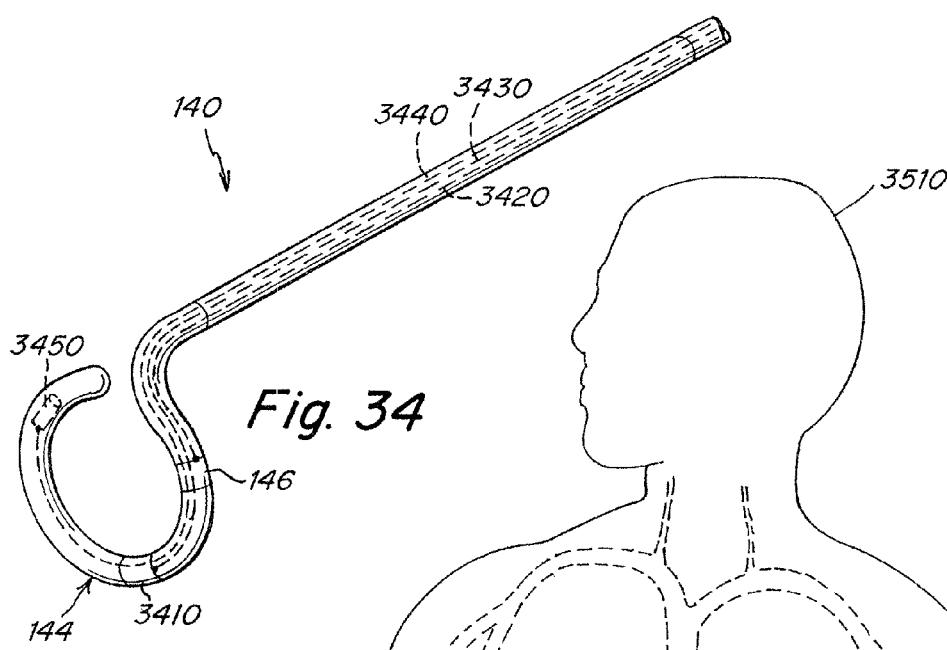
FIG. 34 is a side elevational view of a distal end tip assembly according to another embodiment that includes a localization sensor and a temperature sensor.

In a further embodiment of the invention, one or more of the plurality of ring or band-type electrodes 146 may be replaced with a ring or band-shaped temperature sensor. Reference is now made to FIG. 34, which illustrates a ring-shaped ablation electrode 146 and a ring-shaped temperature sensor 3410. Temperature sensor 3410 may be a thermocouple, thermistor, or any other device for sensing temperature. The temperature sensor 3410 detects the heat of the tissue during ablation by ring or band-shaped ablation electrode 146. Temperature sensing is important during ablation because overheated tissue may explode or char, releasing debris into the bloodstream. Ablation electrode 146 is connected to connector 130 (FIG. 1) via wire 3420, which in turn connects to ablation energy generator 170; ring-shaped temperature sensor 3410 is connected to connector 130 via wire 3430, which in turn connects to controller 150. Ring-shaped electrode 146 can serve as both a reference electrode and an ablation electrode, and may be switched between applications by the controller 150 or by a human operator.

A temperature sensor or sensors, such as, but not limited to one or more thermocouples may be attached to the catheter 100 for temperature sensing during ablation procedures. The temperature sensor may be in contact with the heart tissue or, alternately, may not be in contact with the heart tissue. In other embodiments, temperature sensors may be disposed within one or more of the mapping electrodes 146, 147, for example in a hole drilled within the electrode. One skilled in the art will appreciate that more than one temperature sensor may be used in any particular configuration of catheter 100.

Localization refers to a number of techniques whereby the location of catheter 100 in a patient can be determined. Apparatus and methods for localization can be incorporated into catheter 100.

Referring again to FIG. 34, the distal end 144 of the tip assembly 140 may include an electromagnetic sensor 3450 that may be used for localization. Electromagnetic sensor 3450, may be fixed within the tip assembly 140 of the catheter 100 using any suitable mechanism, such as glue or solder. The electromagnetic sensor 3450 generates signals indicative of the location of the electromagnetic sensor. A wire 3440 electrically connects the electromagnetic sensor 3450 to the controller 150, allowing the generated signals to be transmitted to the controller 150 for processing.

In addition to the electromagnetic sensor 3450 fixed in the distal end of the tip assembly 140, a second electromagnetic sensor (not shown) may be provided that is fixed relative to the patient. The second electromagnetic sensor is attached, for example, to the patient's body, and serves as a reference sensor. A magnetic field is also provided, which is exposed to the electromagnetic sensors. Coils within each electromagnetic sensor generate electrical currents when exposed to the magnetic field. The electrical current generated by the coils of each sensor corresponds to a position of each sensor within the magnetic field. Signals generated by the reference electromagnetic sensor and electromagnetic sensor 3450 fixed to the catheter are analyzed by the controller 150 to ascertain a precise location of electromagnetic sensor 3450.

Further, the signals can be used to generate a contour map of the heart. The map may be generated by contacting the distal end 144 of the tip assembly 140 with the heart tissue at a number of locations along the heart wall. At each location, the electric signals generated by the electromagnetic sensors are transmitted to the controller 150, or to another processor, to determine and record a location of the distal end of the tip assembly. The contour map is generated by compiling the location information for each point of contact. This map may be correlated with heart signal data, measured by one or more electrodes on the distal end of the tip assembly, for each location to generate a map of both the shape and electrical activity of the heart. Signals generated by the electromagnetic sensors may also be analyzed to determine a displacement of the distal end of the tip assembly caused by heartbeat. Further details of performing localization using electromagnetic sensors is provided in U.S. Pat. No. 5,694,945, which is hereby incorporated by reference in its entirety.

As an alternative to the use of electromagnetic sensors other conventional techniques, such as ultrasound or magnetic resonance imaging (MRI) can also be used for localization of tip assembly. Details of performing localization using ultrasound are provided in U.S. Pat. Nos. 6,212,027 and 5,820,568, which are hereby incorporated by reference in their entirety. Moreover, an impedance-based sensor can also be incorporated into the tip assembly. In an impedance-based system, several, such as three, high frequency signals are generated along different axes. The catheter electrodes may be used to sense these frequencies, and with appropriate filtering, the strength of the signal and thus the position of the catheter can be determined. Details of an impedance based system are provided in U.S. Pat. No. 5,983,126, which is hereby incorporated by reference in its entirety.

One skilled in the art will appreciate that the construction of catheter 100 may be optimized to make use of the various localization techniques.

Figure 54:
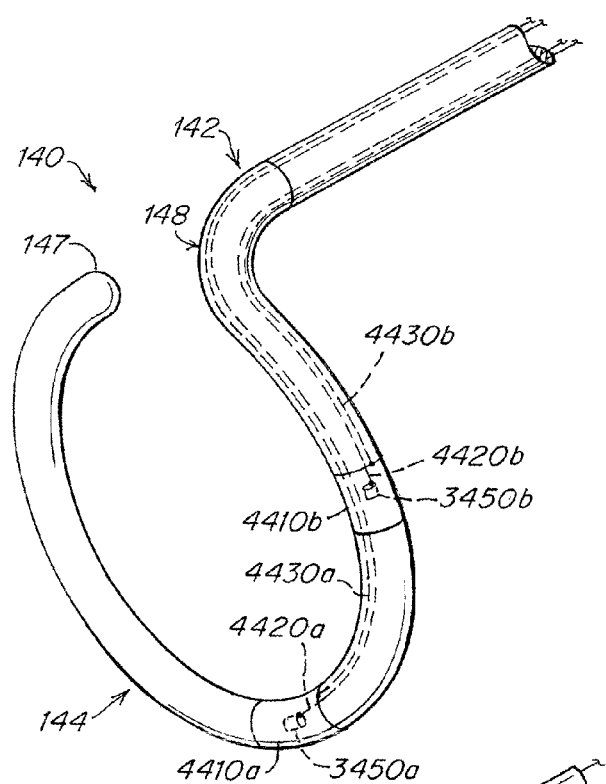
FIG. 54 is a side elevational view of a tip assembly including multiple localization sensors in accordance with another embodiment of the present invention.

According to another embodiment of the invention, multiple electromagnetic sensors may be included in the tip assembly 140 of the catheter 100. FIG. 54 illustrates first and second electromagnetic sensors 3450a and 3450b disposed within the distal end 144 of the tip assembly 140 including electrodes 4410a and 4410b. Wires 4420a and 4420b electrically connect the electromagnetic sensors 3450a and 3450b to the controller 150 of FIG. 1, and wires 4430a and 4430b electrically connect the electrodes 4410a and 4410b to the controller 150. In the example shown, the first and second electromagnetic sensors 3450a and 3450b are located beneath electrodes 4410a and 4410b, respectively. Thus, the first and second location electromagnetic 3450a and 3450b may be used in indicate a location of the first and second electrodes 4410a and 4410b. It should be appreciated that the electromagnetic sensors may alternatively be disposed adjacent corresponding electrodes, or in another proximal location. Further, there need not be any correspondence between the electromagnetic sensors and particular electrodes as the sensors may be placed in any desired location on the tip assembly 140.

Figure 55:
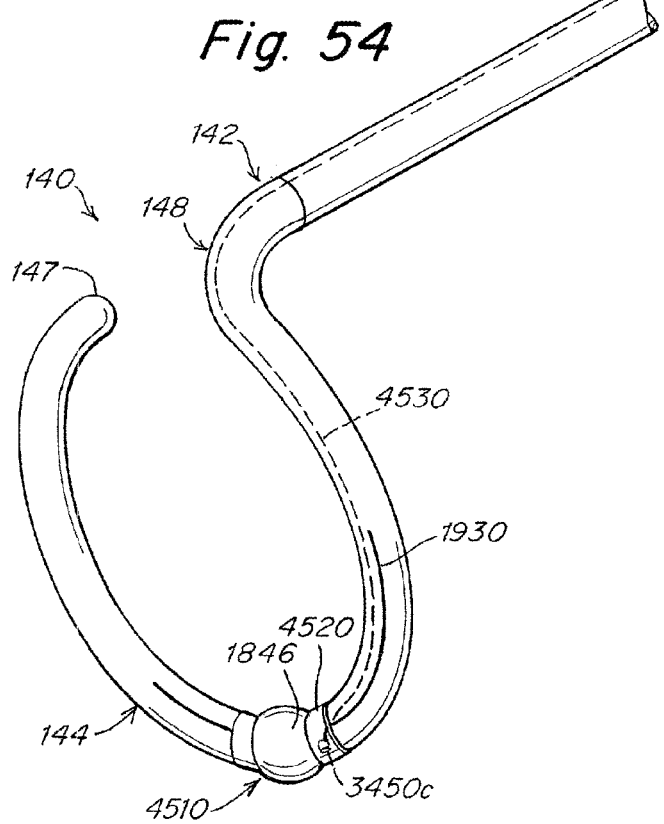
FIG. 55 is a side elevational view of a tip assembly including a movable electrode assembly with a localization sensor in accordance with another embodiment of the present invention.

According to a further embodiment of the invention, an electromagnetic sensor may be included in or near a movable electrode, such as the movable electrode 1846 described in connection with FIGS. 18 and 19. FIG. 55 illustrates a movable electrode assembly 4510 including movable electrode 1846, a slider 4520, and an electromagnetic sensor 3450c. Slider 4520 may be similar to the cylindrically-shaped plastic slider 1910 described in connection with FIG. 19. As shown, the slider 4520 may accommodate the electromagnetic sensor 3450c within the slider 4520 itself, although the sensor may alternatively be included on the surface of the slider. Alternatively still, the electromagnetic sensor 3450c may be included within the movable electrode 1846. The movable electrode assembly 4510 operates as described previously, and is movable along the slit 1930. Wire 4530, which may pass through slit 1930, electrically connects the electromagnetic sensor 3450c to the controller 150 of FIG. 1. The wire 4530 may be insulated, and may be coupled to the push/pull wire 1920 shown in FIG. 19.

It should be appreciated that the electromagnetic sensor 3450c may be used with one or more additional sensors such as electromagnetic sensors 3450a and 3450b described in connection with FIG. 44. It should also be appreciated that the electromagnetic sensors 3450a-c may be implemented as described for the electromagnetic sensor 3450, or alternative localization techniques may be used in place of the electromagnetic sensors 3450a-c, such as the ultrasound, MRI, and impedance-based sensor localization techniques described in connection with electromagnetic sensor 3450.

Fluid Delivery

As the catheter 100 described herein may be used in connection with medical imaging and/or fluoroscopy, it may be desirable to deliver a contrast agent (e.g., a bolus of x-ray contrast agent or radio-opaque dye) to the cardiovascular system during an electrophysiology procedure. Further, it may be desirable to administer drugs such as antithrombogenic agents directly to the cardiovascular system during a catheter procedure. FIGS. 56 and 58 illustrate one embodiment of a structure to deliver fluids, such as drugs and contrast agents, that may be incorporated into embodiments of the catheter 100 described herein. As shown, the tip assembly 140 includes a first and second fluid delivery lumens 4640 and 4610. The first fluid delivery lumen 4640 is disposed within the central lumen 1125 of the catheter 100, while the second fluid delivery lumen 4610 is embedded within the core 1120 of the catheter 100. The second fluid delivery lumen 4610 may be any of the coaxial lumens 1128a-d described previously, or may be an additional lumen. The first and second fluid delivery lumens 4640 and 4610 may have respective dimensions chosen to provide, either individually or in combination, an adequate flow of fluid therethrough. For example, in one implementation, the combined cross-sectional area of the fluid delivery lumens may be chosen to be equivalent to a cylindrical lumen having a diameter between approximately 0.025 inch and approximately 0.039 inch. Opening 4650 on the distal tip 147 of the catheter 100 and opening 4620 on the circumferential surface of the catheter 100 are respectively provided for the first and second fluid delivery lumens. Opening 4620 includes an angled surface 4630 to direct the direction of fluid exit from the catheter 100.

FIGS. 57 and 59 illustrate another embodiment of a structure to deliver fluids. As shown, an external fluid delivery lumen 4710 may be coupled to the external surface of the catheter 100. The lumen 4710 may be sized and shaped to provide a desired fluid flow, without exceeding desired dimensions for catheter size. In the embodiment of FIGS. 47 and 49, the lumen 4710 is disposed on side of the catheter 100. Alternatively, lumen 4710 may surround the periphery of the catheter 100 such that it is coaxial therewith. One or more external lumens, such as lumen 4710, may be provided to deliver fluids, and may be combined with one or more internal fluid delivery lumens, such as those discussed in connection with FIGS. 46 and 48. Each lumen may deliver fluid independently, or may be joined with one or more other lumens at the proximal end of the catheter 100. The joining of lumens enables a single injection of fluid (e.g., via syringe) to provide fluid to a plurality of lumens.

FIGS. 62A-B illustrate a further embodiment of a structure to deliver fluids. In FIG. 62A, a fluid injection manifold 6210 is shown coupled to the catheter 100 to allow a syringe or other fluid injection device (e.g., a power injector) to introduce fluid into the one or more fluid delivery lumens 6220, which transport fluid along the catheter 100. The one or more fluid delivery lumens 6220 may be joined at a proximal opening 6260 in the fluid injection manifold before diverging into separate lumens. The fluid delivery lumen 6220 shown may transport fluids, such as the drugs or contrast agents described above, from the fluid injection manifold 6210 to a distal opening 6250, where fluid may exit the catheter 100. In the embodiment of FIGS. 62A-B, the distal opening 6250 is disposed on a proximal portion 6230 of the catheter 100 having a larger diameter than a distal portion 6240 of the catheter and is perpendicular to the longitudinal axis of catheter 100.

It should be appreciated that a number of variations are possible for the fluid delivery structures described above, and that other manners of fluid delivery are possible. For example, a sheath or introducer, via which the catheter 100 may be inserted into the body, may include fluid delivery means. FIG. 63 illustrates a sheath 2120 having the shaft 110 of a catheter 100 disposed therein. The sheath 2120 includes at least one fluid delivery lumen 6330 to transport fluids, such as the drugs or contrast agents described above, from a fluid injection manifold 6310 to a distal opening 6350. The fluid injection manifold 6310 is provided with a proximal opening 6360 to allow a syringe or other fluid injection device (e.g., a power injector) to introduce fluid into the one or more fluid delivery lumens 6330, which may be joined at the proximal opening 6360. Fluid may exit the sheath 2120 through one or more distal openings 6350 disposed at the distal end of the sheath.

Figure 60:
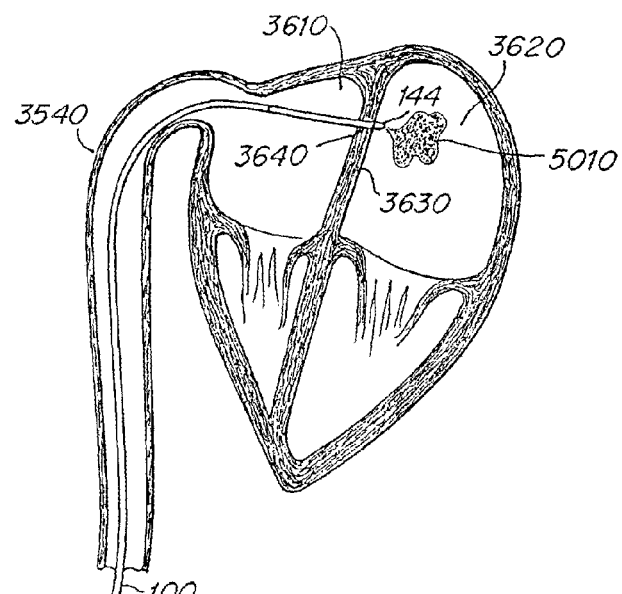
FIG. 60 illustrates the delivery of fluid into the heart via the distal tip of the catheter in accordance with an embodiment of the invention.
Figure 61:
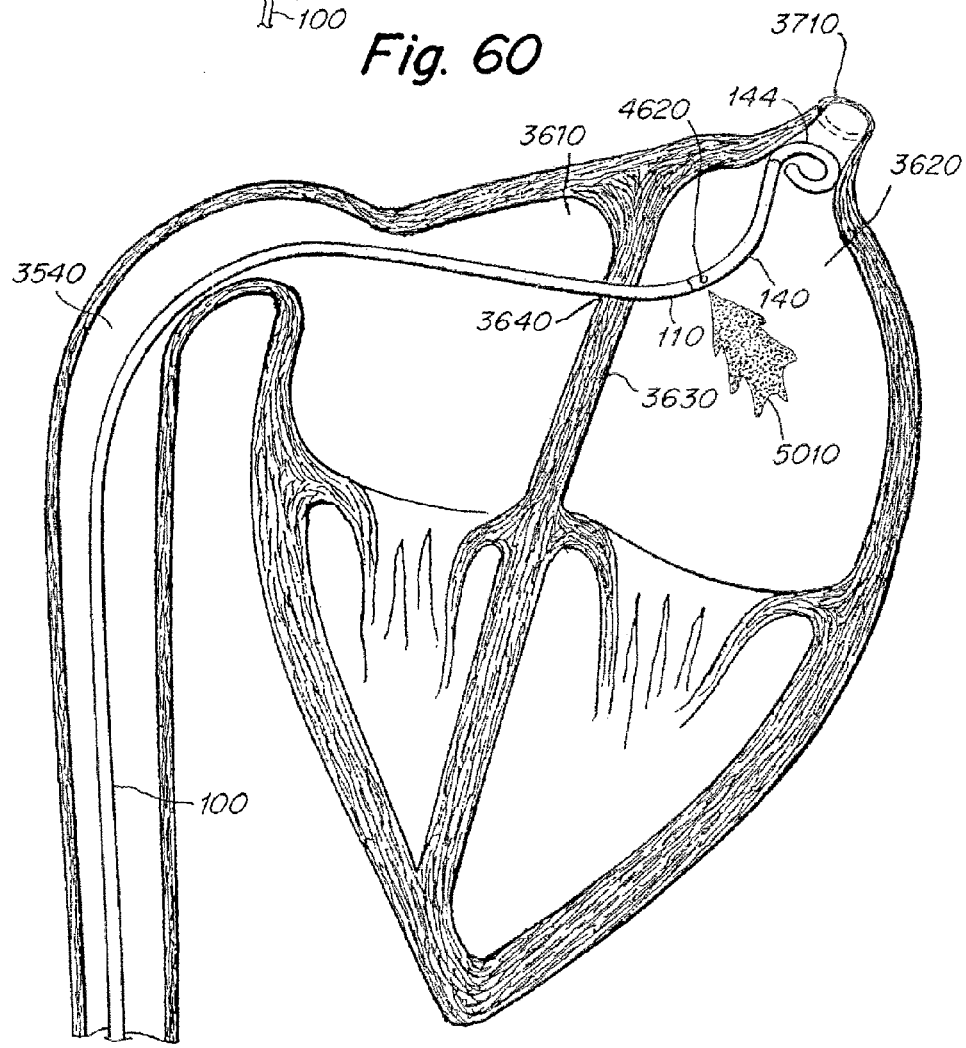
FIG. 61 illustrates the delivery of fluid into the heart via the proximal end of the tip assembly of the catheter in accordance with another embodiment of the invention.

FIGS. 60 and 61 illustrate the delivery of fluid from the catheter 100 into the heart. In FIG. 60, the catheter 100 is shown traversing the septal wall of the heart from the right atrium 3610 into the left atrium 3620. Fluid 5010 is ejected from the tip of the distal end 144 of the catheter 100 into the left atrium 3620. As discussed above, fluid 5010 may be a drug or a contrast agent. In FIG. 61, fluid 5010 is ejected from an opening 4620 in the proximal end of the tip assembly 140 into the left atrium 3620. Although the fluid 5010 is shown being injected into the left atrium 3620 in both FIGS. 60 and 61, it should be appreciated that the fluid 5010 may alternatively be injected into the pulmonary vein 3710, into another blood vessel, or into the right atrium 3610 or ventricles.

Methods for Making the Tip Assembly

FIGS. 5-10 illustrate a number of different jigs that may be used to form a tip assembly having a fixed bend of approximately ninety degrees followed by an arcuately curved distal end. Each of these jigs may be used with a finished catheter (i.e., a catheter which is already fully assembled, and including a handle 120 and electrodes 146, 147 disposed on the distal end of the tip assembly 140), a partially finished tip assembly (i.e., a tip assembly 140 that includes electrodes 146, 147, that is not yet attached to shaft 110 and the handle 120 (FIG. 1)), or an unfinished tip assembly 140 (i.e., a tip assembly 140 without any electrodes 146, 147).

Figure 5:
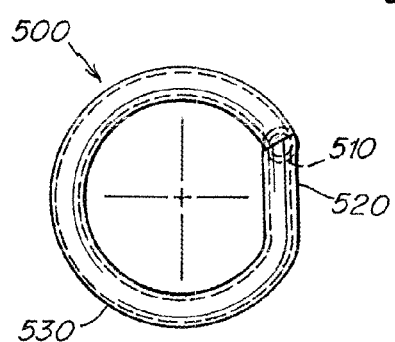
FIG. 5 illustrates a first jig that may be used to impart a fixed shape to the distal end tip assembly according to one embodiment of the present invention.
Figure 6:
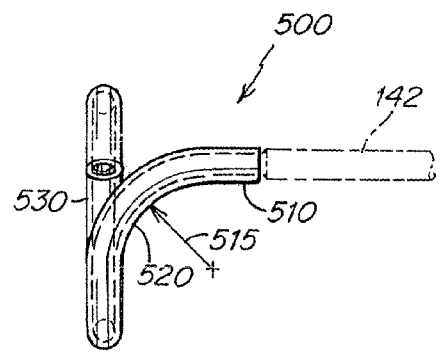
FIG. 6 illustrates a side elevational view of the jig of FIG. 5.

FIGS. 5 and 6 illustrate a first jig 500 that is formed from a hollow tube. In one embodiment, the hollow tube is formed from hypodermic stainless steel tubing, although other materials, such as a high temperature plastics such as TEFLON, DELRIN, etc., may alternatively be used. The material from which the jig 500 is formed should be thermally stable, such that its shape does not change when subjected to temperature in the range of 200-400 degrees Fahrenheit. In one embodiment, the tube used to form the jig 500 has an outer diameter of approximately 0.83 inches and an inner diameter of approximately 0.72 inches to accommodate a tip assembly 140 that is approximately 6 French in diameter, although these dimensions may be varied to accommodate different diameter tip assemblies. For example, to accommodate a tip assembly that is 10 French in diameter, a larger diameter tube would be used. As shown in FIG. 5, the distal end of the jig 500 is formed in a circle having an inner diameter of approximately 0.44 inches and an outer diameter of approximately 0.61 inches. Although the present invention is not limited to any particular dimensions, these dimensions may be used to form a tip assembly 140 in which the diameter of curvature of the distal end 144 in a resting state is approximately 20 mm. Further, and as described in more detail below, these dimensions are selected to account for a certain amount of rebounding (approximately fifteen to twenty percent) in the tip assembly 140 after removal from the jig. Although embodiments are not limited to a tip assembly having a diameter of curvature of approximately 20 mm in a resting state, this size advantageously permits the catheter to be used for mapping and/or ablation procedures within a blood vessel, such as a pulmonary vein. It should be appreciated that for other endocardial or epicardial sites, other dimensions may be used.

As shown in FIG. 6, the jig 500 has a first straight region 510, followed by a curved region 520 having an approximately ninety degree bend relative to the straight region 510, and terminates in an arcuately shaped curved region 530 defining approximately a circle (i.e., spanning approximately 360 degrees). In one embodiment, the straight region 510 is approximately 0.125 inches in length, and the curved region 520 has an inner radius 515 of approximately 0.2 inches. It should be appreciated that other dimensions may be used to impart a different shape to the tip assembly, and to accommodate tip assemblies having a different outer diameters (e.g., a 10 French diameter tip assembly).

According to one embodiment of the present invention, the tip assembly 140 is inserted into the straight region 510 of the jig 500 and the distal end 144 of the tip assembly 140 is advanced until the very distal end of the tip assembly 140 is adjacent the distal end of the jig 500. The jig 500 and the tip assembly 140 are then heated at a predetermined temperature for a predetermined time to permanently shape the tip assembly 140. Applicants have found that heating the jig 500 and the tip assembly 140 at a temperature of approximately 200 to 400 degrees Fahrenheit for approximately thirty minutes to an hour is sufficient to permanently shape the tip assembly 140 to the desired shape. It should be appreciated that the lower the temperature, the greater amount of time is needed to permanently shape the tip assembly 140, and that the time and temperature to which the tip assembly 140 and the jig 500 are heated may vary dependent upon the materials used to form the tip assembly 140 and the jig 500. It should further be appreciated that because catheters may be sterilized prior to use or after use, the temperature to which the tip assembly 140 and the jig 500 is heated should be approximately 20 degrees Fahrenheit above the temperature at which the catheter is sterilized. This helps to prevent the tip assembly 140 from returning to its original shape during sterilization. During sterilization, a retainer may be used to hold the tip assembly 140 in the desired shape.

After heating the tip assembly 140 and the jig 500 for the predetermined time at the predetermined temperature, the tip assembly 140 and the jig 500 are allowed to cool, and the tip assembly 140 is removed from the jig 500. After removal, Applicants have found the arcuately curved distal end 144 of the tip assembly 140 tends to rebound by approximately fifteen to twenty percent, but that further rebounding at temperatures similar to those of human body temperature does not occur. Further, by modifying the materials from which the tip assembly 140 is formed, and by controlling the temperature and the time at which the tip assembly 140 is shaped, rebounding to less than three percent is expected. It should be appreciated that because a certain amount of rebounding is to be expected, the dimensions of the jig 500 should be sized to accommodate the expected amount of rebounding.

The jig of FIGS. 5 and 6 may be used to impart a desired shape to the tip assembly 140 of a finished catheter or to a partially finished tip assembly. For example, in the described embodiment, the length of the straight region 510 is relatively short to permit the tip assembly 140 of a finished catheter to be inserted into the jig 500 without damaging the electrodes 146, 147. This can be advantageous in a manufacturing setting, as finished catheters can be shaped as desired after construction and testing, and prior to shipment to an end user. This may allow fewer distinct catheters to be stocked by the manufacturer of the catheter. Alternatively, in a hospital setting, the ability to shape a finished catheter can allow fewer catheters to be stocked at the hospital, with each of the catheters being capable of being shaped as desired, prior to use.

For use with partially finished tip assemblies, the length of the straight region 510 may be lengthened, with any excess material being cut to length as desired. Moreover, with partially finished tip assemblies, the distal end of the jig 500 may form more than one complete circle, or may form a helical shape.

Although the jig 500 depicted in FIGS. 5 and 6 was used to receive a tip assembly, it should be appreciated that a solid wire of a similar shape may alternatively be used. For example, the hollow stock from which the tip assembly is formed may be fed onto a solid wire having the desired shape, and then heated at an elevated temperature to produce the desired shape. The formed stock can then be removed from the wire, cut to the desired length, and finished in a conventional manner.

Figure 7:
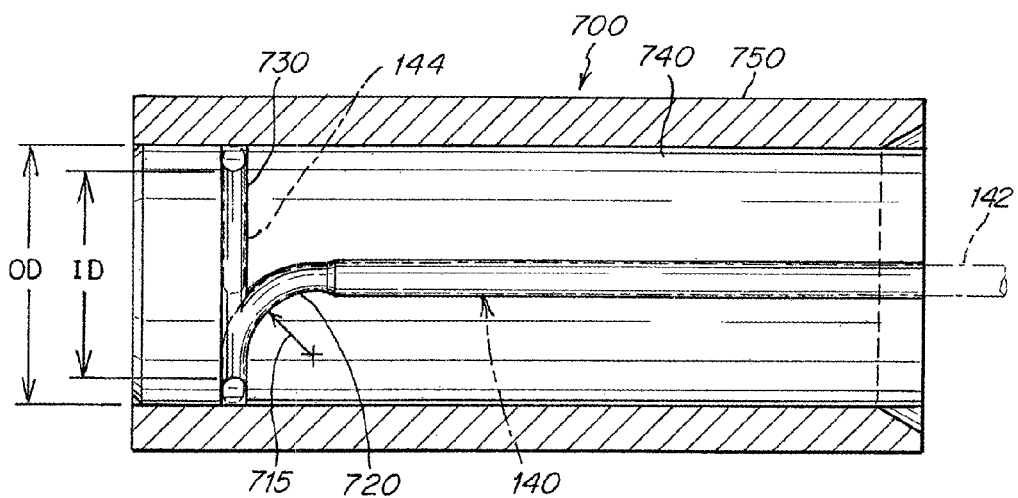
FIG. 7 is a cross sectional side view of a second jig that may be used to impart a fixed shape to the distal end tip assembly according to another embodiment of the present invention.

FIGS. 7 and 8 illustrate a second jig that may also be used to form a tip assembly having the desired shape. In particular, the jig of FIGS. 7 and 8 may be used to permanently shape the distal end of a catheter so that it includes an approximately ninety degree bend followed by an arcuately curved section. According to this embodiment, the jig 700 includes a cylindrical mandrel 740 and a cylindrical retainer 750. The cylindrical mandrel 740 and the cylindrical retainer 750 may be formed from any suitable high temperature materials, such as stainless steel, aluminum, anodized aluminum, or high temperature plastics. In one embodiment, the mandrel 740 has an outer diameter of approximately 0.75 inches and is approximately 2.5 inches long, and the retainer 750 has an inner diameter that is slightly greater than the outer diameter of the mandrel 740, so that the mandrel 740 can be fit within. Although the present invention is not limited to these dimensions, the above-identified dimensions may be used to shape the distal end tip assembly of a catheter so that it is uniquely suited for use inside a blood vessel, such as a pulmonary vein, and to accommodate an anticipated amount of rebounding after removal of the distal end tip assembly from the jig. It should be appreciated that for applications relating to other endocardial sites, other dimensions may be suitably employed.

As shown in FIGS. 7 and 8, the mandrel 740 has a passageway to receive a tip assembly 140 that includes a first straight region 710, a curved region 720 having an approximately ninety degree bend relative to the straight region 710, and an arcuately shaped curved region 730 defining a circle. The passageway may be formed in a conventional manner, for example with a milling machine. In one embodiment, the straight region 710 is approximately 1.9 inches in length, and the curved region 720 has an inner radius 715 of approximately 0.2 inches; the depth of the passageway is approximately 0.068 inches and the width is approximately the same. The described dimensions are selected to shape a tip assembly that is well suited for use within a blood vessel such as a pulmonary vein, although it should be appreciated that other dimensions may be suitably employed for use with different anatomical structures and for different applications. Again, the dimensions of the mandrel 740 and the retainer 750 should be selected to accommodate the expected amount of rebounding. In the embodiment shown, the arcuately shaped curved region 730 is spaced apart from the end of the mandrel 740 to facilitate insertion of the mandrel 740 into the retainer 750.

According to one embodiment of the present invention, a tip assembly 140 is placed into the passageway, and the mandrel 740 and the tip assembly 140 are inserted into the retainer 750. The retainer 750 acts to hold the tip assembly 140 in place within the passageway of the mandrel 740. The jig 700 and the tip assembly 140 are then heated at a predetermined temperature for a predetermined time to permanently shape the tip assembly 140 in a manner similar to that described above with respect to the first jig 500. Because of the larger thermal mass of the jig 700 relative to the jig 500, Applicants have found that a longer time may be needed to shape the tip assembly 140 than with the first jig 500, for example, about 20 additional minutes. To lessen the amount of time required to shape the tip assembly 140, the mandrel 740 may be hollowed out, for example. After heating the tip assembly 140 and the jig 700 for the predetermined time at the predetermined temperature, the tip assembly 140 and the jig 700 are allowed to cool, and then the tip assembly 140 is removed from the jig 700.

As with the jig of FIGS. 5 and 6, the jig 700 may be used to impart a desired shape to the tip assembly 140 of a finished catheter or to a partially finished tip assembly. Indeed, because the tip assembly 140 is placed within the passageway rather than being threaded through it, the jig 700 is particularly well suited for use with a finished tip assembly, as damage to the finished tip assembly resulting from contact with the jig can be avoided.

FIGS. 9 and 10 illustrate another jig that may be used to form a tip assembly 140 having an approximately ninety degree bend followed by an arcuately curved distal end. According to this embodiment, the jig 900 includes a disk-shaped mandrel 940 and a circular cover 950. The disk-shaped mandrel 940 and the circular cover 950 may again be formed from any suitable high temperature materials, such as stainless steel, aluminum, anodized aluminum, or high temperature plastics. The cover 950 is removably attached to the mandrel 940 by a fastener 960, such as a threaded screw, that is passed through an aperture 980 in the cover 950. The mandrel 940 may include a threaded aperture to receive the fastener 960. Attached to the mandrel 940 is a tubular extension 970 that may be made from any suitable material, and which is attached, for example, with a high temperature epoxy or by welding to the mandrel. The tubular extension 970 may be used to support the proximal end 142 of the tip assembly 140 without substantially increasing the thermal mass of the jig 900.

As shown in FIGS. 9 and 10, the mandrel 940 has a passageway to receive a tip assembly 140 that includes a first straight region 910, a curved region 920 having an approximately ninety degree bend relative to the straight region 910, and an arcuately shaped curved region 930 defining a circle. The arcuately shaped curved region 930 may be formed by milling an annular groove in a top surface of the mandrel 940, while the straight region 910 may be formed by drilling a through hole through a section of arcuately shaped curved region 930, for example. A ninety degree bend is formed at the intersection of the annular groove and the through hole. In one embodiment, the arcuately shaped curved region 930 has an outer diameter of approximately 0.5 inches and the annular groove has a width of approximately 0.07 inches. The above-described dimensions are selected to shape the tip assembly so that it is well suited for use within a blood vessel such as a pulmonary vein, although it should be appreciated that other dimensions may be suitably employed for use with different anatomical structures and for different applications. The depth of the groove should be sufficiently greater than the outer diameter of the tip assembly 140 so that the bend in the tip assembly 140 takes place over a length of the tip assembly 140. For example, in one embodiment, the depth of the groove is approximately twice the width of the groove to avoid an immediate ninety degree bend in the tip assembly 140. Such an immediate bend could interfere with operation of the control cables that are used to adjust the radius of curvature of the distal end 144 of the tip assembly 140. Again, the dimensions of the mandrel 940 should be selected to accommodate the expected amount of rebounding, and the desired dimensions and shape of the tip assembly 140.

According to one embodiment of the present invention, a tip assembly 140 is threaded through the tubular extension 970 and the straight region 910 of the mandrel 940, and the distal end 144 of the tip assembly 140 is placed into the annular groove in the mandrel 940. The cover 950 is then fastened to the mandrel 940. The cover 950 acts to hold the tip assembly 140 in place within the passageway of the mandrel 940. The jig 900 and the tip assembly 140 are then heated at a predetermined temperature for a predetermined time to permanently shape the tip assembly 140 in a manner similar to that described above with respect to the first and second jigs. After heating the tip assembly 140 and the jig 900 for the predetermined time at the predetermined temperature, the tip assembly 140 and the jig 900 are allowed to cool, and then the tip assembly 140 is removed from the jig 900.

As with the previously described jigs 500 and 700, the jig 900 may be used to impart a desired shape to the tip assembly 140 of a finished catheter or to a partially finished tip assembly. Because the distal end of the tip assembly is inserted straight ahead into the mandrel 940, rather than along a curved path, the jig 900 is also particularly well suited for use with a finished tip assembly, as damage to the finished tip assembly resulting from contact with the jig can be avoided.

Although the jigs 500, 700, and 900 of FIGS. 5-10 have been illustrated and described as being useful in forming a tip assembly having a fixed bend of approximately ninety degrees followed by an arcuately curved distal end, it should be appreciated that each of these jigs may also be used or modified for use with a tip assembly including an active bend, such as described above with respect to FIG. 19. For example, for creating a permanent bias of a few degrees relative to the straight regions 510, 710, and 910, the approximately ninety degree bend may have a larger radius that may be varied according to the intended use of the tip assembly. As noted above with respect to FIG. 19, by permanently biasing the intermediate section 2180 (FIG. 19) away from the straight regions 510, 710, and 910, bending takes place in a known and controlled manner. Moreover, it should be appreciated that rather than terminating in a curved region 530, 730, 930 that spans approximately 360 degrees in a single plane (e.g., a circle), the curved region 530, 730, and 930 may be formed in a helical shape.

Methods of Use

As discussed above, the catheter system of the invention may be used in mapping and/or ablation applications. In one embodiment of the invention, the mapping or ablation is performed in the heart of a patient. In the mapping application, multiple signals may be received from the heart tissue via multiple electrodes on the catheter. Each electrode may measure a continuous signal (i.e., electrogram) from the heart tissue. The continuous signal may represent the voltage of the heart tissue in contact with the electrode, with respect to a reference voltage, as it changes with time. The reference voltage may be obtained using a dedicated reference electrode or another measurement electrode. The quality of the signal received by each electrode improves as both the size of the electrode and the isolation of the electrode increases.

Preferably, multiple electrodes are employed, such that multiple electrograms may be obtained simultaneously. This allows for multiple data points, which can result in a more precise mapping of the heart signal and a shorter required measurement time. A shorter measurement time advantageously reduces the x-ray exposure to patients and physicians during fluoroscopy, when employed during the catheter procedure.

The mapping function of the catheter can be used for a number of different applications. For example, in one application, the catheter may be used to measure the conductivity at various points of the septal wall, which separates the left and right sides of the heart, to determine a preferred sight for puncture of the septal wall. In another application, the conductivity of the heart tissue may be measured between adjacent electrodes in contact with the heart tissue to determine the continuity of a lesion formed by ablation. In still another application, the catheter may used to identify electrical signals within the heart that are characteristic of a number of heart conditions. For example, the focus site of an arrhythmia (e.g., atrial fibrillation, AV nodal tachycardia or tachycardia resulting from Wolff-Parkinson-White syndrome).

Figure 35:
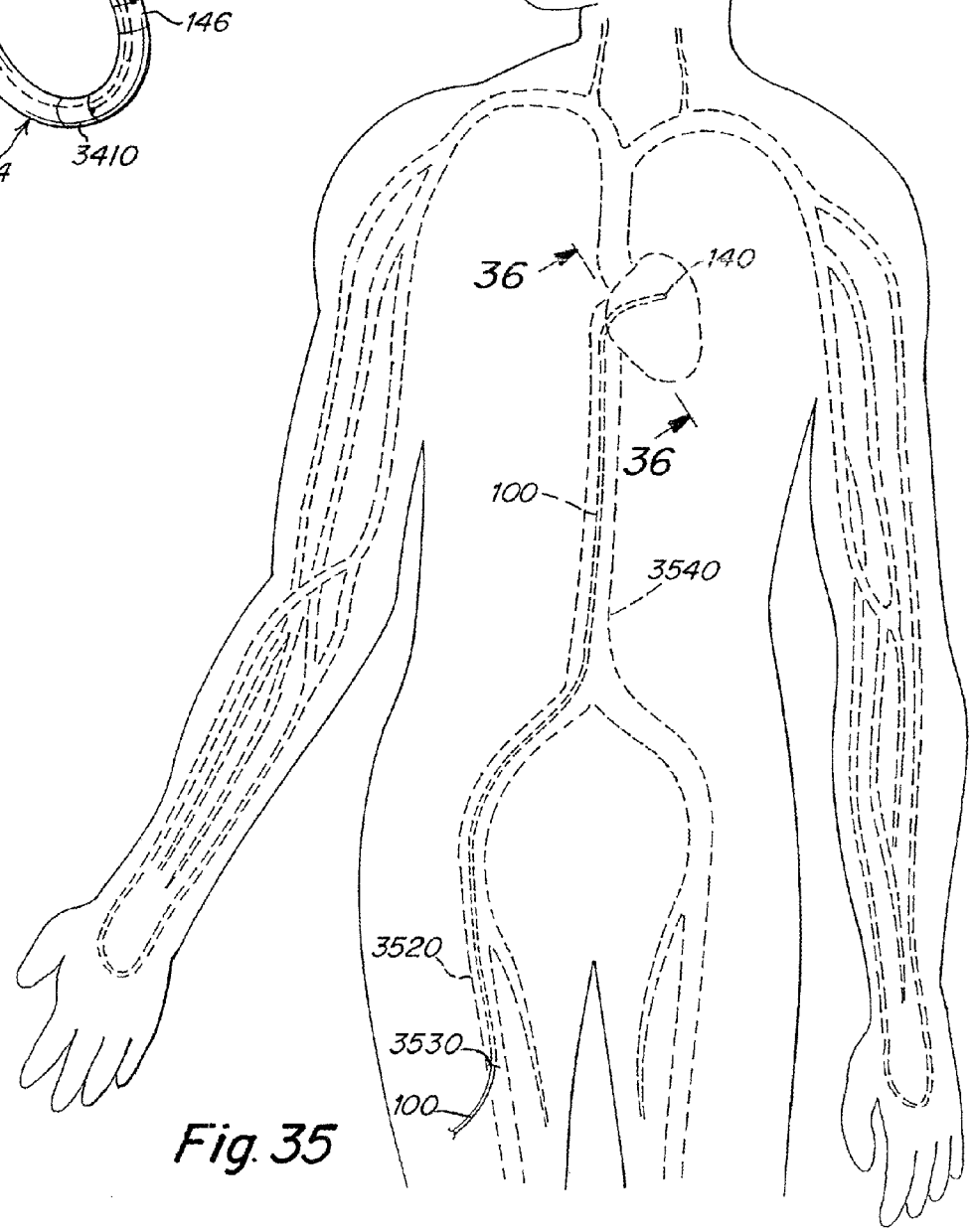
FIG. 35 illustrates the insertion of a catheter into a body of a patient.

Reference is now made to FIG. 35, which illustrates a method of insertion of the catheter 100 into a patient 3510 in accordance with an embodiment of the present invention. The catheter 100 is inserted into the patient via a blood vessel, e.g., subclavian vein, jugular vein, or femoral vein. In FIG. 35, the catheter 100 is shown entering a femoral vein 3520 via an incision 3530 in the thigh of the patient 3510. The catheter 100 may be introduced into the vein using a sheath/dilator (not shown). The sheath/dilator may be anchored at the incision site, for example by stitching the sheath/dilator to the patient's skin at the area of incision 3530. From the incision site 3530 in the femoral vein 3520, the catheter 100 may be advanced independently, or through a sheath/dilator, up the inferior vena cava 3540 into the right atrium of the heart.

Figure 36:
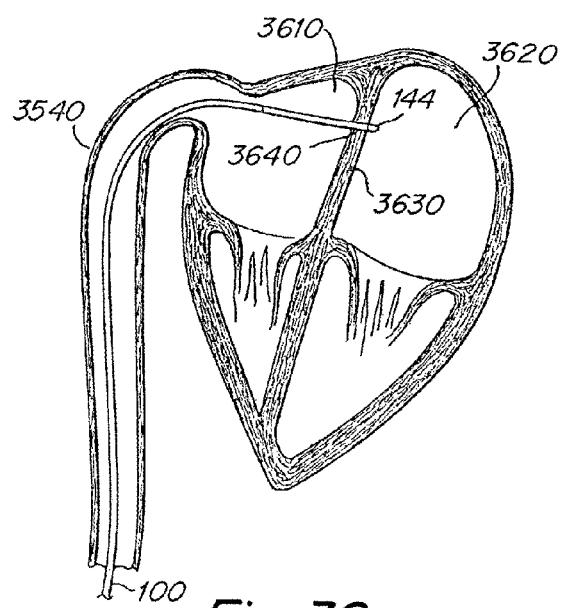
FIG. 36 illustrates the insertion of the catheter into a heart.

Reference is now made to FIG. 36, which illustrates a diagram of a cross-sectional view of the heart taken along line 36-36 in FIG. 35. The catheter 100 is shown entering the right atrium 3610 via the inferior vena cava 3540. For passage of the catheter 100 into the left atrium, 3620 the distal end of the catheter 100 may be passed trans-septally through the septal wall 3630. In one method, a puncture 3640 in the septal wall 3630 is made at the foramen ovale, an area of the septal wall having a decreased thickness and decreased conductivity relative to other areas of the septal wall. As described previously, electrodes on the distal end of the catheter 100 may be used to locate the foramen ovale, or another preferred site to puncture the septal wall 3630. As shown in FIG. 36, the distal end of the tip assembly 140 of the catheter 100 traverses the septal wall 3630 from the right atrium 3610 and enters the left atrium 3620. The distal end of the catheter 100 may be used for mapping and/or ablation procedures in the left atrium 3620 or may be maneuvered into the pulmonary vein(s) for mapping and/or ablation. It should be appreciated that the catheter may also be used to perform mapping and/or ablation in the right heart, in the ventricles, or in any other area of the heart or blood vessels of the circulatory system, and that the catheter 1 need not pass through the septal wall to enter these areas.

Figure 37:
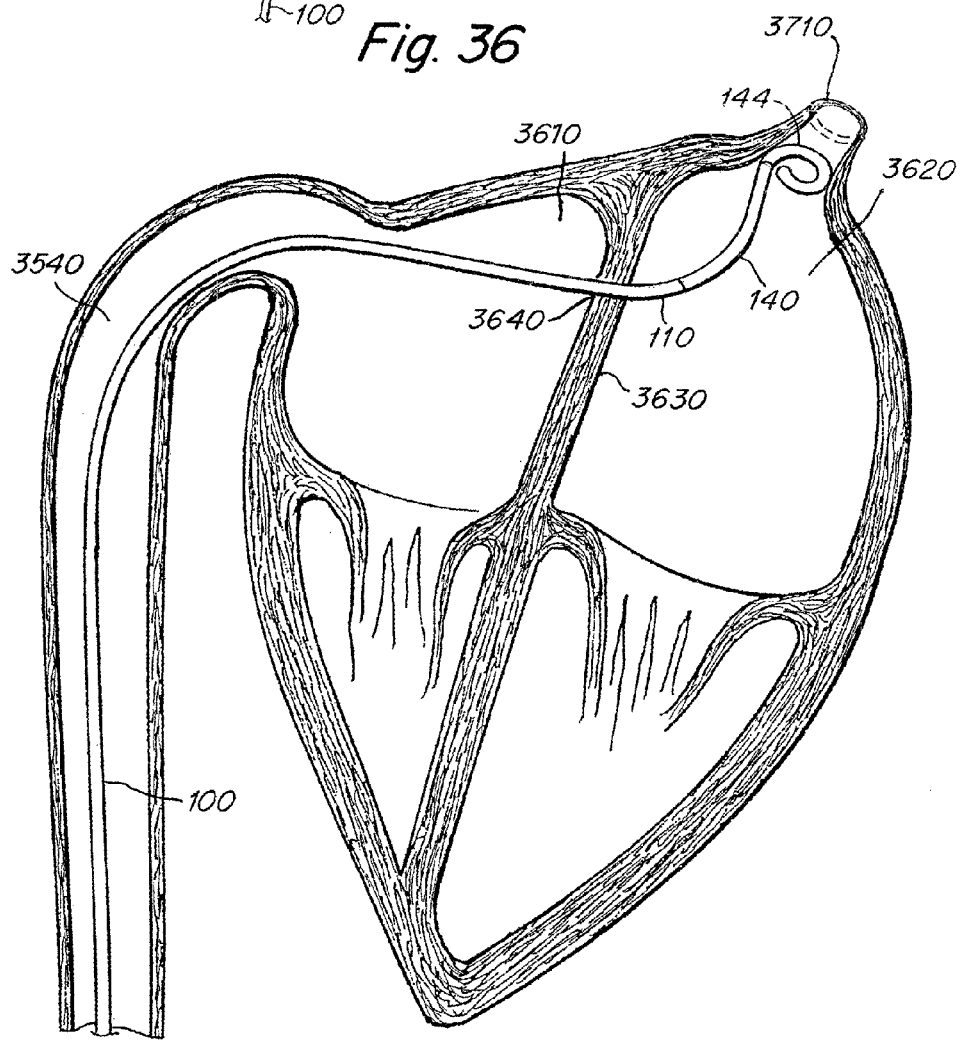
FIG. 37 illustrates the insertion of the distal end of the catheter into the ostium of a pulmonary vein in the heart.

Referring now to FIG. 37, which is an expanded view of FIG. 36, in one embodiment of the present invention, once inside the left atrium 3620, the distal end of the catheter 100 may be advanced towards the ostium of one of the pulmonary veins 3710. In this embodiment, the radius of curvature of the distal end 144 of the tip assembly 140 is remotely adjusted to snugly fit against the annular walls of the pulmonary vein 3710 by manipulation of the actuator 122, 124 (FIG. 1) that controls the radius of curvature of the distal end 144 of the tip assembly 140. In this position, the graphical indicia 3310 (FIG. 33) on the handle 120 may be used to give the user an indication of the diameter of the ostium of the pulmonary vein at this location. Mapping may be performed, as can ablation.

Because of the approximately ninety degree bend in the tip assembly 140, pressure applied to the handle 120 is translated via the shaft to force the arcuately curved distal end 144 of the tip assembly 140 tightly against the ostium of the pulmonary vein 3710. In this position, the user may also apply pressure to the actuator (e.g., the slide actuator 124) that controls the radius of curvature of the distal end 144 of the tip assembly 140 to also apply an outwardly radial pressure that further forces the distal end 144 of the tip assembly 140 tight against the ostium of the pulmonary vein 3710. Mapping may then be performed to locate a focal trigger or triggers of atrial fibrillation. It should be appreciated that the ability to force the distal end 144 of the tip assembly 140 tightly against the inner circumferential surface of a blood vessel, such as the ostium of a pulmonary vein, enhances the ability to accurately locate a focal trigger or triggers of atrial fibrillation.

Should ablation be determined to be an effective solution, ablation energy may then be provided by the ablation energy generator 170 (FIG. 1) to create a circular lesion around the circumference of the ostium of the pulmonary vein 3710. By controlling which electrodes (disposed on the distal end of the tip assembly, but not shown) are used to provide such ablation energy, a full circumferential lesion or a partial circumferential lesion may be created. Further, by monitoring of the temperature of at the site (for example, by using one or more temperature sensors disposed along the distal end 144 of the tip assembly 140), care may be exercised to ensure that charring is prevented and that the appropriate temperatures necessary for ablation are achieved. After ablation, the mapping electrodes may then be used to verify that the electrical conductivity of the tissue has been destroyed.

One advantage of using a catheter according to the invention in the described method is that only a single catheter is necessary to (1) determine the location of the foramen ovale for passage through the septal wall, (2) perform any desired mapping procedures, and (3) perform any desired ablation procedures. This avoids the need for changing catheters during procedures as between, for example, mapping and ablation procedures. It may also reduce the number of removal and reinsertion operations needed during a patient's electrophysiology study and treatment procedure. Further, because the radius of curvature of the distal end of the tip assembly may be remotely altered within the endocardial site, the catheter may be used on any sized patient from an infant or small animal to an adult or large animal, as "one size fits all." Moreover, should the size of a blood vessel or other anatomical structure be different than that which was anticipated, it is not necessary to remove the catheter and insert another more appropriately sized catheter. As noted above, this ability to be used with any sized patient can also reduce the need for a manufacturer or a care provider to stock a number of differently sized catheters.

The various configurations of the catheter illustrated in the figures are exemplary. One skilled in the art will appreciate that the number, size, orientation, and configuration of the mapping electrodes and the ablation electrodes, as well as various diameters and lengths of the catheter can be provided depending upon the particular application.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

The invention claimed is:

1. A catheter comprising:
a handle having a distal end and a proximal end, the handle including an actuator;
a flexible shaft having a proximal end and a distal end and a longitudinal axis that extends along a length of the flexible shaft, the proximal end of the flexible shaft being attached to the distal end of the handle;
a tip assembly having a proximal end and a distal end, the proximal end of the tip assembly being attached to the distal end of the flexible shaft, and the tip assembly including a wire formed of a superelastic material and shaped to bias the tip assembly in a first orientation including a curved shape spanning at least approximately three hundred and sixty degrees;
a cable, attached to the actuator and the distal end of the tip assembly, that extends through the flexible shaft, the cable being adapted to increase a radius of curvature of the curved shape in response to movement of the actuator;
at least one lumen in the flexible shaft to conduct fluid along the length of the flexible shaft;
at least one opening in the flexible shaft adapted to release fluid conducted by the at least one lumen; and
a movable electrode that is movable by a push-pull wire between a first position and a second position position on the tip assembly, the first position being spaced apart from the second position by at least three hundred and sixty degrees along the curved shape such that the movable electrode is movable to form a circular lesion;
wherein the cable and the wire extend along an entire length of the distal end of the tip assembly to a point adjacent a most distal end of the tip assembly.

2. The catheter of claim 1, wherein the wire has a radius of curvature smaller than or equal to a radius of curvature of the cable when the tip assembly is in the first orientation.

3. The catheter of claim 1, wherein the first orientation further includes a bend, proximal to the curved shape, the bend having a bias angle of ninety degrees relative to the longitudinal axis of the flexible shaft.

4. The catheter of claim 3, further comprising a second cable adapted to change an angle of the bend to an angle smaller than the bias angle in response to movement of a second actuator, wherein the second cable is disposed in an outer portion of the tip assembly with respect to the angle of the bend.

5. The catheter of claim 1, wherein:
the first orientation includes a bend, proximal to the curved shape, the bend having a bias angle relative to the longitudinal axis of the flexible shaft; and
the catheter further comprises a second cable adapted to change an angle of the bend to an angle of ninety degrees relative to the longitudinal axis of the flexible shaft in response to movement of a second actuator.

6. The catheter of claim 1, wherein the wire is formed of a nickel titanium compound.

7. The catheter of claim 6, wherein the wire is formed of Nitinol.

8. The catheter of claim 1, wherein the proximal end of the tip assembly includes a bend of approximately ninety degrees relative to the longitudinal axis of the flexible shaft, and wherein at least a portion of the curved shape of the distal end of the tip assembly is oriented in a plane that is approximately perpendicular to the longitudinal axis of the flexible shaft.

9. The catheter of claim 1, wherein the at least one opening is disposed proximal to the bend.

10. The catheter of claim 1, wherein the at least one opening is in the tip assembly.

11. The catheter of claim 1, wherein the at least one lumen comprises a lumen disposed along a central longitudinal axis of the shaft.

12. The catheter of claim 1, wherein the at least one lumen includes a lumen disposed along an axis that is offset from a central longitudinal axis of the shaft.

13. The catheter of claim 1, further comprising a second cable anchored proximal to the tip assembly and adapted to steer the tip assembly in a plane perpendicular to the longitudinal axis of the shaft.

14. The catheter of claim 1, further comprising a cap electrode coupled to the distal end of the tip assembly.

* * * * *